US005886148A

United States Patent [19]
Segre et al.

[11] Patent Number: 5,886,148
[45] Date of Patent: Mar. 23, 1999

[54] PARATHYROID HORMONE RECEPTOR

[75] Inventors: Gino V. Segre, Wayland; Henry M. Kronenberg, Belmont; Abdul-Badi Abou-Samra, Plainville; Harald Juppner, Boston; John T. Potts, Jr., West Newton; Ernestina Schipani, Boston, all of Mass.

[73] Assignee: The General Hospital Corporation, Boston, Mass.

[21] Appl. No.: 468,249

[22] Filed: Jun. 6, 1995

Related U.S. Application Data

[62] Division of Ser. No. 864,465, Apr. 6, 1992, Pat. No. 5,261,686, which is a continuation of Ser. No. 681,702, Apr. 5, 1991, abandoned.

[51] Int. Cl.$^6$ ............................ C07K 14/00; A61K 38/00
[52] U.S. Cl. .......................... 530/350; 435/7.1; 435/65.1; 435/252.3; 435/320.1; 435/325; 530/300; 514/2
[58] Field of Search ................................. 435/7.1, 65.1, 435/252.3, 320.1, 325; 530/360, 350; 514/2

[56] References Cited

U.S. PATENT DOCUMENTS

| | | | |
|---|---|---|---|
| 4,736,866 | 4/1988 | Leder et al. | 800/1 |
| 4,740,463 | 4/1988 | Weinberg et al. | 435/172.3 |
| 5,494,806 | 2/1996 | Segre et al. | 435/65.1 |

OTHER PUBLICATIONS

Masn et al. (Nature) 1987 329:836–838.
Koriuchin et al. (1991) J. Biol. Chem 266:4700–4705.
Quinn et al. (1990) J. Biol. Chem 265: 22342–22347.
Abou–Samra et al., Endocrinology 125:2215–2217, 1989.
Abou–Samra et al., Endocrinology 129:2547–2554, 1991.
Abou–Samra et al., Endocrinology 125:2594–2599, 1989.
Abou–Samra et al., Endocrinology 124:1107–1113, 1989.
Abou–Samra et al., J. of Biological Chemistry 265:58–62, 1990.
Abou–Samra et al., Proc. Natl. Acad. Sci. USA 89:2732–2736, 1992.
Bonventre et al., J. of Biological Chemistry 265:4934–4938, 1990.
Chan et al., Molecular Endocrinology 4:638–646, 1990.
Horiuchi et al., J. of Biological Chemistry 266:4700–4705, 1991.
Hruska et al., J. Clin. Invest. 79:230–239, 1987.
Ishihara et al., The EMBO Journal 10:1635–1641, 1991.
Juppner et al., J. of Biological Chemistry 263:8557–8560, 1988.
Juppner et al., Science 254:1024–1026, 1991.
Juppner et al., Biochemistry 29:6941–6946, 1990.
Juppner et al., Peptides 11:1139–1142, 1990.
Lin et al., Science 254:1022–1024, 1991.
Orloff et al., J. of Biological Chemistry 264:6097–6103, 1989.
Rosenblatt et al., Endocrinology 107:545:550, 1980.
Rosenblatt et al., Proceedings of the Sixth American Peptide Symposium, Ed. by E. Groos and M. Meienhofer, pp. 1025–1028, 1979.
Segre et al., J. of Biological Chemistry 254:6980–6986, 1979.
Segre et al., Endocrinology 116:1024–1029, 1985.
Shigeno et al., Analytical Biochemistry 179:268–273, 1989.
Shigeno et al., J. of Biological Chemistry 263:3864–3871, 1988.
Shigeno et al., J. of Biological Chemistry 263:3872–3878, 1988.
Yamamoto et al., J. Clin. Invest. 71:404–407, 1983.
Yamamoto et al., J. Bone and Mineral Research 3:707–712, 1988.
Yamamoto et al., J. Bone and Mineral Research 3:289–295, 1988.
Yamamoto et al., Endocrinology 122:1208–1217, 1988.
Luben et al., Abstracts of Papers Presented at the Twenty--seventh Annual Meeting of The American Society for Cell Biology, 72 St. Louis, MO, 1987.
Luben et al., Twelfth Annual Meeting of the American Society for Bone and Mineral Research presented Abstract#272, Aug. 29, 1990.
Chuang et al., American Society for Bone and Mineral Research Abstract #282, Jun. 1987.
Karpf et al., American Society for Bone and Mineral Research Abstract #218, Jun. 1988.
Caulfield et al., American Society for Bone and Mineral Research Abstract #317, Jun. 1988.
Luben et al., American Society for Bone and Mineral Research Abstract #319, Jun. 1988.
Masu et al., Nature 329:836–838, 1987.
Sims et al., Science 241:585–589, 1988.
Gearing et al., EMBO J. 8:3667–3676, 1989.
Lim et al., J. Biol. Chem. 263:11493–11497, 1988.
Lee et al., J. Bacteriol. 166:385–391, 1986.
Lin et al., Science 254:1022–1024, 1991.
Sambrook et al., *Molecular Cloning* 2nd ed., Cold Spring Harbor (NY); ch. 11 (selected pages).

*Primary Examiner*—Stephen Walsh
*Assistant Examiner*—Kenneth A. Sorensen
*Attorney, Agent, or Firm*—Fitch & Richardson P.C.

[57] ABSTRACT

DNA encoding a parathyroid hormone receptor; production and isolation of recombinant and synthetic parathyroid hormone receptor polypeptides and fragments; antibodies to parathyroid hormone receptors and receptor fragments; methods for screening candidate compounds for antagonistic or agonistic effects on parathyroid hormone receptor action; and diagnostic and therapeutic methods of these compounds are disclosed.

12 Claims, 36 Drawing Sheets

```
TGGGCACAGC CACCCTGTTG GTAGTCCAGG GGCCAGCCCA CTGAGCTGG                                                    60
GTGGCCCCGT TGGACTCGGC CCTAGGGAAC GGGGGCG ATG GGA GCG CCC CGG ATC                                        115
                                        Met Gly Ala Pro Arg Ile
                                          1                   5

TCG CAC AGC CTT GCC TTG CTC CTC TGC TCC GTG CTC TGC TCC AGC GTC                                         163
Ser His Ser Leu Ala Leu Leu Leu Cys Ser Val Leu Cys Ser Ser Val
         10                      15                      20

TAC GCA CTG GAT GCC GAT GAT ATA ACG AAG GAG CAG ATC                                                     211
Tyr Ala Leu Val Asp Ala Asp Asp Ile Thr Lys Glu Gln Ile
             25                      30                  35

ATT CTT CGC AAT GCC CAG GCC CAG TGT GAG CAG CGC CTG AAA GAG                                             259
Ile Leu Arg Asn Ala Gln Ala Gln Cys Glu Gln Arg Leu Lys Glu
         40                      45                  50

GTC CTC AGG GTC CCT GAA CTT GCT GAA TCT GCC AAA GAC TGG ATG TCA                                         307
Val Leu Arg Val Pro Glu Leu Ala Glu Ser Ala Lys Asp Trp Met Ser
         55                      60                      65                  70

AGG TCT GCA AAG ACA AAG AAG GAG AAA CCT GCA GAA GTT TCT TAT CCC                                         355
Arg Ser Ala Lys Thr Lys Lys Glu Lys Pro Ala Glu Val Ser Tyr Pro
             75                      80                      85

CAG GCA GAG GAG GAG CTA CCT GAG TGG GAC AAC ATT GTG TGC CTG GAT                                         403
Gln Ala Glu Glu Glu Leu Pro Glu Trp Asp Asn Ile Val Ser Arg Leu Gln Asp
         90                      95                      100

GGC TTC TGC CTA CCT GAG TGG GAC AAC ATT GTG TGC CCT GCT GGA                                             451
Gly Phe Cys Leu Pro Glu Trp Asp Asn Ile Val Cys Trp Pro Ala Gly
         105                     110                     115
```

FIG. 1a

```
GTG CCC GGC AAG GTG GTG GCC GTG CCC TGC CCC GAC TAC TTC TAC GAC        499
Val Pro Gly Lys Val Val Ala Val Pro Cys Pro Asp Tyr Phe Tyr Asp
        120                 125                 130

TTC AAC CAC AAA GGC CGA GCC TAT CGG CGC TGT GAC AGC AAT GGC AGC        547
Phe Asn His Lys Gly Arg Ala Tyr Arg Arg Cys Asp Ser Asn Gly Ser
        135                 140                 145                 150

TGG GAG CTG GTG CCT GGG AAC CGG ACA TGG GCG AAT TAC AGC GAA            595
Trp Glu Leu Val Pro Gly Asn Arg Thr Trp Ala Asn Tyr Ser Glu
        155                 160                 165

TGT GTC AAG TTT CTG ACC AAC GAG ACC CGG GAA GTC TTT GAT                643
Cys Val Lys Phe Leu Thr Asn Glu Thr Arg Glu Val Phe Asp
        170                 175                 180

CGC CTC GGA ATG ATC TAC ACT GTG GGC TAC TCC ATC TCT GGC TCC            691
Arg Leu Gly Met Ile Tyr Thr Val Gly Tyr Ser Ile Ser Gly Ser
        185                 190                 195

CTC ACT GTG GCT GTG CTG ATT CTG GGT TAC TTT AGG AGG TTA CAT TGC        739
Leu Thr Val Ala Val Leu Ile Leu Gly Tyr Phe Arg Arg Leu His Cys
        200                 205                 210

ACC CGA AAC TAC ATT CAC ATG CAT CTC TTC GTG TCC TTT ATG CTC CGG        787
Thr Arg Asn Tyr Ile His Met His Leu Phe Val Ser Phe Met Leu Arg
        215                 220                 225                 230

GCT GTA AGC ATC TTC ATC AAG GAT GCT GTG CTC TAC TCG GGG GTT TCC        835
Ala Val Ser Ile Phe Ile Lys Asp Ala Val Leu Tyr Ser Gly Val Ser
        235                 240                 245
```

FIG. 1b

```
ACA GAT GAA ATC GAG CGC ATC ACC GAG GAG CTG AGG GCC TTC ACA       883
Thr Asp Glu Ile Glu Arg Ile Thr Glu Glu Leu Arg Ala Phe Thr
            250                 255                 260

GAG CCT CCC GCT GAC AAG GCG GGT TTT GTG TGC GGC AGA GTG GCG       931
Glu Pro Pro Ala Asp Lys Ala Gly Phe Val Cys Gly Arg Val Ala
        265                 270                 275

GTA ACC GTC TTC CTT TAC CTG ACC ACC AAC TAC TAC TGG ATC CTG       979
Val Thr Val Phe Leu Tyr Leu Thr Thr Asn Tyr Tyr Trp Ile Leu
            280                 285                 290

GTG GAA GGC CTC TAC CTT CAC AGC CTC ATC TTC ATG GCT TTT TCT      1027
Val Glu Gly Leu Tyr Leu His Ser Leu Ile Phe Met Ala Phe Ser
        295                 300                 305         310

GAG AAA AAG TAT CTC TGG GGT TTC ACA TTA TTT GGC TGG GGC CTC CCT  1075
Glu Lys Lys Tyr Leu Trp Gly Phe Thr Leu Phe Gly Trp Gly Leu Pro
            315                 320                 325

GCC GTG TTT GTC GCT GTG TGG GTG ACC GTG AGG GCT ACA CTG GCC AAC  1123
Ala Val Phe Val Ala Val Trp Val Thr Val Arg Ala Thr Leu Ala Asn
        330                 335                 340

ACT GAG TGC TGG GAC CTG AGT TCG GGG AAT AAG AAA TGG ATC ATA CAG  1171
Thr Glu Cys Trp Asp Leu Ser Ser Gly Asn Lys Lys Trp Ile Ile Gln
            345                 350                 355

GTG CCC ATC CTG GCA GCT ATT GTG GTG AAC TTT CTT TTT ATC AAT      1219
Val Pro Ile Leu Ala Ala Ile Val Val Asn Phe Leu Phe Ile Asn
        360                 365                 370
```

FIG. 1C

```
ATA ATC AGA GTC CTG GCT ACT AAA CTC CGG GAG ACC AAT GCA GGG AGA    1267
Ile Ile Arg Val Leu Ala Thr Lys Leu Arg Glu Thr Asn Ala Gly Arg
375             380                 385                 390

TGT GAC ACG AGG CAA CAG TAT AGA AAG CTG CTG AAG TCC ACG CTA GTC    1315
Cys Asp Thr Arg Gln Gln Tyr Arg Lys Leu Leu Lys Ser Thr Leu Val
        395                 400                 405

CTC ATG CCG CTA TTT GGG GTG CAC TAC ATC GTC TTC ATG GCC ACG CCG    1363
Leu Met Pro Leu Phe Gly Val His Tyr Ile Val Phe Met Ala Thr Pro
410                 415                 420

TAC ACA GAA GTA TCA GGG ATT CTT TGG CAA GTC CAA ATG CAC TAT GAA    1411
Tyr Thr Glu Val Ser Gly Ile Leu Trp Gln Val Gln Met His Tyr Glu
425                 430                 435

ATG CTC TTC AAT TCA TTC CAG GGA TTT TTC GTT GCC ATT ATA TAC TGT    1459
Met Leu Phe Asn Ser Phe Gln Gly Phe Phe Val Ala Ile Ile Tyr Cys
        440                 445                 450

TTC TGC AAT GGA GAG GTA CAA GCA GAG ATC AAG CGG AAG TCA TGG AGC CGA    1507
Phe Cys Asn Gly Glu Val Gln Ala Glu Ile Lys Lys Arg Lys Ser Trp Ser Arg
455                 460                 465                 470

TGG ACC CTG GCC TTG GAC TTC AAG CGG AAG GCC CGG AGT GGC AGC AGT    1555
Trp Thr Leu Ala Leu Asp Phe Lys Arg Lys Ala Arg Ser Gly Ser Ser
        475                 480                 485

ACC TAC AGC TAT GGC CCC ATG GTG TCA CAT ACA AGT GTC ACC AAT GTG    1603
Thr Tyr Ser Tyr Gly Pro Met Val Ser His Thr Ser Val Thr Asn Val
490                 495                 500
```

FIG. 1d

```
GGA CCT CGA GGG GGC TGG CCT TGT CCC TCA GCC CTC GAC TAGCTCCCTGG    1652
Gly Pro Arg Gly Gly Trp Pro Cys Pro Ser Ala Leu Asp
505                 510                 515

GGCTGGAGCC AGTGCCAATG GCCATCACCA GTTGCCTGGC TATGTGAAGC ATGGTTCCAT  1712
TTCTGAGAAC TCATTGCCTT CATCTGGCCC AGAGCCTGGC ACCAAAGATG ACGGGTATCT  1772
CAATGGCTCT GGACTTTATG AGCCAATGGT TGGGGAACAG CCCCCTCCAC TCCTGGAGGA  1832
GGAGAGAGAG ACAGTCATGT GACCCATATC                                   1862
```

FIG. 1e

```
TGGGCACAGC CACCCTGTTG GTAGTCCAGG GGCCAGCCCA CTGAGCTGGC ATATCAGCTG                                          60

GTGGCCCCGT TGGACTCGGC CCTAGGGAAC GGGGCG ATG GGA GCG CCC CGG ATC                                          115
                                        Met Gly Ala Pro Arg Ile
                                         1               5

TCG CAC AGC CTT GCC TTG CTC CTC TGC TCC GTG CTC AGC TCC GTC                                              163
Ser His Ser Leu Ala Leu Leu Leu Cys Ser Val Leu Ser Ser Val
              10                  15                  20

TAC GCA CTG GTG GAT GAT GCC GAT GTC ATA ACG AAG GAG GAG CAG ATC                                          211
Tyr Ala Leu Val Asp Asp Ala Asp Val Ile Thr Lys Glu Glu Gln Ile
              25                  30                  35

ATT CTT CTG CGC AAT GCC CAG GCC CAG TGT GAG CAG CGC CTG AAA GAG                                          259
Ile Leu Leu Arg Asn Ala Gln Ala Gln Cys Glu Gln Arg Leu Lys Glu
              40                  45                  50

GTC CTC AGG GTC CCT GAA CTT GCT CTA GAA TCT GCC AAA GAC TGG ATG TCA                                      307
Val Leu Arg Val Pro Glu Leu Ala Leu Glu Ser Ala Lys Asp Trp Met Ser
      55                  60                  65                  70

AGG TCT GCA AAG ACA AAG GAG AAA CCT GAG GTT TCT GCA GAA AAG CTT TAT CCC                                  355
Arg Ser Ala Lys Thr Lys Glu Lys Pro Glu Val Ser Ala Glu Lys Leu Tyr Pro
      75                  80                  85

CAG GCA GAG GAG TCC AGG GAA GTT GAC AGG AGC CGG CTG AGG CTG CAG GAT                                      403
Gln Ala Glu Glu Ser Arg Glu Val Asp Arg Ser Arg Leu Arg Leu Gln Asp
      90                  95                 100

GGC TTC TGC CTA CCT GAG TGG GAC AAC ATT GTG TGC TGG CCT GCT GGA                                          451
Gly Phe Cys Leu Pro Glu Trp Asp Asn Ile Val Cys Trp Pro Ala Gly
     105                 110                 115

GTG CCC GGC AAG GTG GTG GTG GCC CCC TGC CCC GAC TAC TTC TAC GAC                                          499
Val Pro Gly Lys Val Val Val Ala Pro Cys Pro Asp Tyr Phe Tyr Asp
             120                 125                 130

FIG. 2a
```

```
TTC AAC CAC AAA GGC CGA GCC TAT CGG CGC TGT GAC AGC AAT GGC AGC    547
Phe Asn His Lys Gly Arg Ala Tyr Arg Arg Cys Asp Ser Asn Gly Ser
135                 140                 145                 150

TGG GAG CTG GTG CCT GGG AAC AAC CGG ACA TGG GCG AAT TAC AGC GAA    595
Trp Glu Leu Val Pro Gly Asn Asn Arg Thr Trp Ala Asn Tyr Ser Glu
            155                 160                 165

TGT GTC AAG TTT CTG ACC AAC GAG ACC CGG GAA GTC GGA GAA TTT GAT    643
Cys Val Lys Phe Leu Thr Asn Glu Thr Arg Glu Val Arg Glu Phe Asp
        170                 175                 180

CGC CTC GGA ATG ATC TAC ACT GTG GGC TAC TCC ATC TCT CTG GGC TCC    691
Arg Leu Gly Met Ile Tyr Thr Val Gly Tyr Ser Ile Ser Leu Gly Ser
    185                 190                 195

CTC ACT GTG GCT GTG CTG ATT CTC GGT TAC TTT AGG AGG TTA CAT TGC    739
Leu Thr Val Ala Val Leu Ile Leu Gly Tyr Phe Arg Arg Leu His Cys
200                 205                 210

ACC CGA AAC TAC ATT CAC ATG CAT CTC TTC GTG TCC TTT ATG CTC CGG    787
Thr Arg Asn Tyr Ile His Met His Leu Phe Val Ser Phe Met Leu Arg
215                 220                 225                 230

GCT GTA AGC ATC TTC ATC AAG GAT GCT GTG CTC TAC TCG GGG GTT TCC    835
Ala Val Ser Ile Phe Ile Lys Asp Ala Val Leu Tyr Ser Gly Val Ser
        235                 240                 245
```

FIG. 2b

```
ACA GAT GAA ATC GAG CGC ATC ACC GAG GAG CTG AGG GCC TTC ACA      883
Thr Asp Glu Ile Glu Arg Ile Thr Glu Glu Leu Arg Ala Phe Thr
        250                     255                 260

GAG CCT CCC GCT GAC AAG GCG GGT TTT GTG GGC TGC AGA GTG GCG      931
Glu Pro Pro Ala Asp Lys Ala Gly Phe Val Gly Cys Arg Val Ala
    265                     270                 275

GTA ACC GTC TTC CTT TAC TTC CTG ACC AAC TAC TAC TGG ATC CTG      979
Val Thr Val Phe Leu Tyr Phe Leu Thr Asn Tyr Tyr Trp Ile Leu
        280                     285                 290

GTG GAA GGC CTC TAC CTT CAC AGC CTC ATC TTC ATG GCT TTC TCT     1027
Val Glu Gly Leu Tyr Leu His Ser Leu Ile Phe Met Ala Phe Ser
    295                     300                 305         310

GAG AAA TAT CTC TGG GGT TTC ACA TTA TTT GGC CTC GGC CTC CCT     1075
Glu Lys Tyr Leu Trp Gly Phe Thr Leu Phe Gly Leu Gly Leu Pro
        315                     320                 325

GCC GTG TTT GTC GCT GTG TGG GTG ACC GTG AGG GCT ACA CTG GCC AAC 1123
Ala Val Phe Val Ala Val Trp Val Thr Val Arg Ala Thr Leu Ala Asn
    330                     335                 340

ACT GAG TGC TGG GAC CTG AGT TCG GGG AAT AAG AAA TGG ATC ATA CAG 1171
Thr Glu Cys Trp Asp Leu Ser Ser Gly Asn Lys Lys Trp Ile Ile Gln
        345                     350                 355

GTG CCC ATC CTG GCA GCT ATT GTG GTG AAC TTT CTT TTT ATC AAT     1219
Val Pro Ile Leu Ala Ala Ile Val Val Asn Phe Leu Phe Ile Asn
    360                     365                 370

ATA ATC AGA GTC CTG ACT AAA CTC CGG GAG ACC AAT GCA GGG AGA     1267
Ile Ile Arg Val Leu Thr Lys Leu Arg Glu Thr Asn Ala Gly Arg
        375                     380                 385         390
```

FIG. 2c

```
TGT GAC ACG AGG CAA CAG TAT AGA AAG CTG CTG AAG TCC ACG CTA GTC    1315
Cys Asp Thr Arg Gln Gln Tyr Arg Lys Leu Leu Lys Ser Thr Leu Val
         395                 400                 405

CTC ATG CCG CTA TTT GGG GTG CAC TAC ATC GTC TTC ATG GCC ACG CCG    1363
Leu Met Pro Leu Phe Gly Val His Tyr Ile Val Phe Met Ala Thr Pro
         410                 415                 420

TAC ACA GAA GTA TCA GGG ATT CTT TGG CAA GTC CAA ATG CAC TAT GAA    1411
Tyr Thr Glu Val Ser Gly Ile Leu Trp Gln Val Gln Met His Tyr Glu
         425                 430                 435

ATG CTC TTC AAT TCA TTC CAG GGA TTT TTC GTT GCC ATT ATA TAC TGT    1459
Met Leu Phe Asn Ser Phe Gln Gly Phe Phe Val Ala Ile Ile Tyr Cys
         440                 445                 450

TTC TGC AAT GGA GAG GTA CAA GCA GAG ATC AAG TCA TGG AGC CGA        1507
Phe Cys Asn Gly Glu Val Gln Ala Glu Ile Lys Lys Ser Trp Ser Arg
         455                 460                 465         470

TGG ACC CTG GCC TTG GAC TTC AAG CGG AAG GCC CGG AGT GGC AGC AGT    1555
Trp Thr Leu Ala Leu Asp Phe Lys Arg Lys Ala Arg Ser Gly Ser Ser
         475                 480                 485

ACC TAC AGC TAT GGC CCC ATG GTG TCA CAT ACA AGT GTC ACC AAT GTG    1603
Thr Tyr Ser Tyr Gly Pro Met Val Ser His Thr Ser Val Thr Asn Val
         490                 495                 500
```

FIG. 2d

```
GGA CCT CGA GGG GGG CTG GCC TTG TCC CTC AGC CCT CGA CTA GCT CCT    1651
Gly Pro Arg Gly Gly Leu Ala Leu Ser Leu Ser Pro Arg Leu Ala Pro
        505                 510                 515

GGG GCT GGA GCC AGT GCC AAT GGC CAT CAC CAG TTG CCT GGC TAT GTG    1699
Gly Ala Gly Ala Ser Ala Asn Gly His His Gln Leu Pro Gly Tyr Val
        520                 525                 530

AAG CAT GGT TCC ATT TCT GAG AAC TCA TTG CCT TCA TCT GGC CCA GAG    1747
Lys His Gly Ser Ile Ser Glu Asn Ser Leu Pro Ser Ser Gly Pro Glu
535                 540                 545                 550

CCT GGC ACC AAA GAT GAC GGG TAT CTC AAT GGC TCT GGA CTT TAT GAG    1795
Pro Gly Thr Lys Asp Asp Gly Tyr Leu Asn Gly Ser Gly Leu Tyr Glu
        555                 560                 565

CCA ATG GTT GGG GAA CAG CCC CCT CCA CTC CTG GAG GAG GAG AGA GAG    1843
Pro Met Val Gly Glu Gln Pro Pro Pro Leu Leu Glu Glu Glu Arg Glu
        570                 575                 580

ACA GTC ATG TGACCCATAT C                                           1863
Thr Val Met
        585
```

FIG. 2e

```
GGCGGGGGCC GCGGCGGGCGA GCTCGGAGGC CGGCGGGCGGC TGCCCCGAGG GACGCGGCCC         60

TAGGCGGTGG CG ATG GGG GCC GCC CGG ATC GCA CCC AGC CTG GCG CTC              108
              Met Gly Ala Ala Arg Ile Ala Pro Ser Leu Ala Leu
                1                   5                       10

CTA CTC TGC TGC CCA GTG CTC AGC TCC GCA TAT GCG CTG GTG GAT GCG           156
Leu Leu Cys Cys Pro Val Leu Ser Ser Ala Tyr Ala Leu Val Asp Ala
             15                   20                   25

GAC GAT GTC TTT ACC AAA GAG GAA CAG ATT TTC CTG CTG CAC CGT GCC           204
Asp Asp Val Phe Thr Lys Glu Glu Gln Ile Phe Leu Leu His Arg Ala
     30                   35                   40

CAG GCG CAA TGT GAC AAG CTG CTC AAG GAA GTT CTG CAC ACA GCA GCC           252
Gln Ala Gln Cys Asp Lys Leu Leu Lys Glu Val Leu His Thr Ala Ala
 45                   50                   55                   60

AAC ATA ATG GAG TCA GAC AAG GCA TCG ACA CCA TCT ACG TCA GGG               300
Asn Ile Met Glu Ser Asp Lys Ala Ser Thr Pro Ala Ser Thr Ser Gly
             65                   70                   75

AAG CGC AGG AAA GAG AAG CCC ACC GGC AGC AGG CGC AGA GGG TTC TAC CCT GAG TCT AAA   348
Lys Pro Arg Lys Glu Lys Ala Pro Thr Gly Ser Arg Arg Arg Gly Phe Tyr Pro Glu Ser Lys
         80                   85                   90

GAG AAC AAG GAC GTG CCC ACC GGC CCC ACC GGC AGC AGG CGT CCC TGT           396
Glu Asn Lys Asp Val Pro Thr Gly Ser Arg Arg Arg Gly Arg Pro Cys
     95                  100                  105

CTG CCC GAG TGG GAC AAC ATC GTT TGC TGG CCA TTA GGG GCA CCA GGT           444
Leu Pro Glu Trp Asp Asn Ile Val Cys Trp Pro Leu Gly Ala Pro Gly
110                  115                  120

GAA GTG GCA GTA CCT TGT CCC GAT TAT ATT TAT GAC TTC AAT CAC               492
Glu Val Ala Val Pro Cys Pro Asp Tyr Ile Tyr Asp Phe Asn His
125                  130                  135                  140
```

FIG. 3a

```
AAA GGC CAT GCC TAC AGA CGC TGT GAC CGC AAT GGC AGC TGG GAG GTG    540
Lys Gly His Ala Tyr Arg Arg Cys Asp Arg Asn Gly Ser Trp Glu Val
            145                 150                 155

GTT CCA GGG CAC AAC CGG ACG TGG GCC AAC TAC AGC GAG TGC CTC AAG    588
Val Pro Gly His Asn Arg Thr Trp Ala Asn Tyr Ser Glu Cys Leu Lys
        160                 165                 170

TTC ATG ACC AAT GAG ACG CGG GAA CGG GAG GTA TTT GAC CGC CTA GGC    636
Phe Met Thr Asn Glu Thr Arg Glu Arg Glu Val Phe Asp Arg Leu Gly
    175                 180                 185

ATG ATC TAC ACC GTG GGA TAC TAT TTT AGG CGG CTG GCC CTC ATC CTG    684
Met Ile Tyr Thr Val Gly Tyr Tyr Phe Arg Arg Leu Ala Leu Ile Leu
190                 195                 200

GCT GTG CTC ATC CTG GCC TAT TTT AGG CGG CTG CAC TGC ACG CGC AAC    732
Ala Val Leu Ile Leu Ala Tyr Phe Arg Arg Leu His Cys Thr Arg Asn
205                 210                 215                 220

TAC ATC CAC ATG CAC ATG TTC CTG TCG TTT ATG CTG CGC GCC GCG AGC    780
Tyr Ile His Met His Met Phe Leu Ser Phe Met Leu Arg Ala Ala Ser
            225                 230                 235

ATC TTC GTG AAG GAC GCT GTG CTC TAC TCT GGC TTC ACG CTG GAT GAG    828
Ile Phe Val Lys Asp Ala Val Leu Tyr Ser Gly Phe Thr Leu Asp Glu
        240                 245                 250
```

FIG. 3b

```
GCC GAG CGC ACA GAG GAA GAG TTG CAC ATC ATC GCG CAG GTG CCA    876
Ala Glu Arg Thr Glu Glu Glu Leu His Ile Ile Ala Gln Val Pro
        255                 260                 265

CCT CCG CCG GCC GCT GCC GTA GGC TAC GCT GGC TGC CGC GTG GCG    924
Pro Pro Pro Ala Ala Ala Val Gly Tyr Ala Gly Cys Arg Val Ala
270                 275                 280

GTG ACC TTC CTC TAC TTC CTG GCT ACC AAC TAC TAC TGG ATT CTG    972
Val Thr Phe Leu Tyr Phe Leu Ala Thr Asn Tyr Tyr Trp Ile Leu
285                 290                 295                 300

GTG GAG GGG CTG TAC TTG CAC AGC CTC ATC TTC ATG GCC TTT TCA   1020
Val Glu Gly Leu Tyr Leu His Ser Leu Ile Phe Met Ala Phe Ser
        305                 310                 315

GAG AAG TAC CTG TGG GGC TTC ACC ATC TTT GGC TGG GGT CTA CCG   1068
Glu Lys Tyr Leu Trp Gly Phe Thr Ile Phe Gly Trp Gly Leu Pro
320                 325                 330

GCT GTC TTC GTG GCT GTG TGG GTC AGA GCA ACC TTG GCC AAC       1116
Ala Val Phe Val Ala Val Trp Val Arg Ala Thr Leu Ala Asn
335                 340                 345

ACT GGG TGC TGG GAT CTG AGC TCC GGG CAC AAG AAG TGG ATC ATC CAG   1164
Thr Gly Cys Trp Asp Leu Ser Ser Gly His Lys Lys Trp Ile Ile Gln
        350                 355                 360

GTG CCC ATC CTG GCA TCT GTT GTG CTC AAC TTC ATC CTT TTT ATC AAC   1212
Val Pro Ile Leu Ala Ser Val Val Leu Asn Phe Ile Leu Phe Ile Asn
365                 370                 375                 380

ATC ATC CGG GTG CTT GCC ACT AAG CTT CGG GAG ACC AAT GCG GGC CGG   1260
Ile Ile Arg Val Leu Ala Thr Lys Leu Arg Glu Thr Asn Ala Gly Arg
        385                 390                 395
```

FIG. 3c

```
TGT GAC ACC AGG CAG CAG TAC CGG AAG CTG CTC AGG TCC ACG TTG GTG  1308
Cys Asp Thr Arg Gln Gln Tyr Arg Lys Leu Leu Arg Ser Thr Leu Val
            400                 405                 410

CTC GTG CCG CTC TTT GGT GTC CAC TAC ACC GTC TTC ATG GCC TTG CCG  1356
Leu Val Pro Leu Phe Gly Val His Tyr Thr Val Phe Met Ala Leu Pro
            415                 420                 425

TAC ACC GAG GTC TCA GGG ACA TTG TGG CAG ATC CAG ATG CAT TAT GAG  1404
Tyr Thr Glu Val Ser Gly Thr Leu Trp Gln Ile Gln Met His Tyr Glu
            430                 435                 440

ATG CTC TTC AAC TCC TTC CAG GGA TTT TTT GTT GCC ATC ATA TAC TGT  1452
Met Leu Phe Asn Ser Phe Gln Gly Phe Phe Val Ala Ile Ile Tyr Cys
            445                 450                 455     460

TTC TGC AAT GGT GAG GTG CAG GCA GAG ATT AGG AAG TCA TGG AGC CGC  1500
Phe Cys Asn Gly Glu Val Gln Ala Glu Ile Arg Lys Ser Trp Ser Arg
            465                 470                 475

TGG ACA CTG GCG TTG GAC TTC AAG CGC AAA GCA CGA AGT GGG AGT AGC  1548
Trp Thr Leu Ala Leu Asp Phe Lys Arg Lys Ala Arg Ser Gly Ser Ser
            480                 485                 490

AGC TAC AGC TAT GGC CCA ATG GTG TCT CAC ACG AGT GTG ACC AAT GTG  1596
Ser Tyr Ser Tyr Gly Pro Met Val Ser His Thr Ser Val Thr Asn Val
            495                 500                 505
```

FIG. 3d

```
GGC CCC CGT GCA GGA CTC CTC AGC CTC CCC CGC CCC CGC CTG CCT CCT   1644
Gly Pro Arg Ala Gly Leu Leu Ser Leu Pro Arg Pro Arg Leu Pro Pro
510                 515                 520

GCC ACT ACC AAT GGC CAC TCC CAG CTG CCT GGC CAT GCC AAG CCA GGG   1692
Ala Thr Thr Asn Gly His Ser Gln Leu Pro Gly His Ala Lys Pro Gly
525                 530                 535                 540

GCT CCA GCC ACT GAG ACT GAA ACC CTA CCA GTC ACT ATG GCG GTT CCC   1740
Ala Pro Ala Thr Glu Thr Glu Thr Leu Pro Val Thr Met Ala Val Pro
            545                 550                 555

AAG GAC GAT GGA TTC CTT AAC GGC TCC TGC TCA GGC CTG GAT GAG GAG   1788
Lys Asp Asp Gly Phe Leu Asn Gly Ser Cys Ser Gly Leu Asp Glu Glu
                560                 565                 570

GCC TCC GGG TCT GCG CGG CCG CCT CCA TTG TTG CAG GAA GGA TGG GAA   1836
Ala Ser Gly Ser Ala Arg Pro Pro Pro Leu Leu Gln Glu Gly Trp Glu
575                 580                 585

ACA GTC ATG TGACTGGGCA CTAGGGGGCT AGACTGCTGG CCTGGGCACA           1885
Thr Val Met
590

TGGACAGATG GACCAAGAAG CCAGTGTTTG GCTGGTTGTC TATTCGGGAT CTGGACCAGG  1945
AAGATAACAA AAGGAAAATG GAAGTGGACG AAGCAGAGAA AGGAAGAGAG GTTTTGCAGG  2005
AATTAAATAT GTTCCCTCAG TTGGATGATG AGGACACAAG GAAGGC                2051
```

FIG. 3e

Rb.Pep x Ok.Pep

```
  1 MGAARIAPSLALLLCCPVLSSAYALVDADDVFTKEEQIFLLHRAQAQCDK  50
    |||:||..||||||||.||||.||||||||||:|||||:||:.||||:..
  1 MGAPRISHSLALLLCCSVLSSVYALVDADDVITKEEQIILLRNAQAQCEQ  50

51 LLKEVLHTAANIMESDKGWTPASTSGKPRKEKASGKFYPESKENKDVPTG 100
    |||||: .::: ||.|:|   | |:|.:|||:..:|||:..|..::|..
 51 RLKEVLR.VPELAESAKDW..MSRSAKTKKEKPAEKLYPQAEESREVSDR  97

101 SRRRGRPCLPEWDNIVCWPLGAPGEVVAVPCPDYIYDFNHKGHAYRRCDR 150
    || ..:  |||||||||||| |.||.|||||||||:|||||||:|||||.
 98 SRLQDGFCLPEWDNIVCWPAGVPGKVVAVPCPDYFYDFNHKGRAYRRCDS 147

151 NGSWEVVPGHNRTWANYSECLKFMTNETREREVFDRLGMIYTVGYSMSLA 200
    |||||:|||:|||||||||||:||:||||||||||||||||||||||:||:
148 NGSWELVPGNNRTWANYSECVKFLTNETREREVFDRLGMIYTVGYSISLG 197

201 SLTVAVLILAYFRRLHCTRNYIHMHMFLSFMLRAASIFVKDAVLYSGFTL 250
    ||||||||:|||||||||||||||||:|:||||||.|||:|||||||||..
198 SLTVAVLILGYFRRLHCTRNYIHMHLFVSFMLRAVSIFIKDAVLYSGVST 247

251 DEAERLTEEELHIIAQVPPPPAAAAVGYAGCRVAVTFFLYFLATNYYWIL 300
    || ||:|||||: :.:   ||:|. .|:.||||||.|||||.|||||||
248 DEIERITEEELRAFTE...PPPADKAGFVGCRVAVTVFLYFLTTNYYWIL 294

301 VEGLYLHSLIFMAFFSEKKYLWGFTIFGWGLPAVFVAVWVGVRATLANTG 350
    ||||||||||||||||||||||||||:|||||||||||||||.|||||||:
295 VEGLYLHSLIFMAFFSEKKYLWGFTLFGWGLPAVFVAVWVTVRATLANTE 344

351 CWDLSSGHKKWIIQVPILASVVLNFILFINIIRVLATKLRETNAGRCDTR 400
    |||||||:||||||||||..:|:||||||||||||||||||||||||||
345 CWDLSSGNKKWIIQVPILAAIVVNFILFINIIRVLATKLRETNAGRCDTR 394

401 QQYRKLLRSTLVLVPLFGVHYTVFMALPYTEVSGTLWQIQMHYEMLFNSF 450
    ||||||:|||||:|||||||.|||| ||||||||.|||:||||||||||
395 QQYRKLLKSTLVLMPLFGVHYIVFMATPYTEVSGILWQVQMHYEMLFNSF 444

451 QGFFVAIIYCFCNGEVQAEIRKSWSRWTLALDFKRKARSGSSSYSYGPMV 500
    |||||||||||||||||||:|||||||||||||||||||||||.|||||||
445 QGFFVAIIYCFCNGEVQAEIKKSWSRWTLALDFKRKARSGSSTYSYGPMV 494

501 SHTSVTNVGPRAGLSLPLSPRLPP...ATTNGHSQLPGHAKPGAPATETE 547
    |||||||||||:||.|.|||||:|   |..|||  ||||...|.|  ...:.
495 SHTSVTNVGPRGGLALSLSPRLAPGAGASANGHHQLPGYVKHGSISENSL 544

548 TLPVTMAVPKDDGFLNGSCSGLDEEASGSARPPPLLQEGWETVM 591
    . ... :..||||:||| ||| |. |  | ..|||||:::|||
545 PSSGPEPGTKDDGYLNG..SGLYEPMVG.EQPPPLLEEERETVM 585
```

| Gap Weight: | 3.000 | Average Match: | 0.540 |
|---|---|---|---|
| Length Weight: | 0.100 | Average Mismatch: | -0.396 |
| Quality: | 712.2 | Length: | 594 |
| Ratio: | 1.215 | Gaps: | 6 |
| Percent Similarity: | 87.113 | Percent Identity: | 77.835 |

FIG. 4

```
R15   MGAARIAPSL ALLLCCPVLS SAYALVDADD VFTKEEQIFL LHRAQAQCDK  50
Oko   MGAPRISHSL ALLLCCSVLS SVYALVDADD VITKEEQIIL LRNAQAQCEQ  50
Okh   MGAPRISHSL ALLLCCSVLS SVYALVDADD VITKEEQIIL LRNAQAQCEQ  50
                 ---------- A ----------

R15   LLKEVLHTAA NIMESDKGWT PASTSGKPRK EKASGKFYPE SKENKDVPTC  100
Oko   RLKEVLR.VP ELAESAKDW. .MSRSAKTKK EKPAEKLYPQ AEESREVSDR   97
Okh   RLKEVLR.VP ELAESAKDW. .MSRSAKTKK EKPAEKLYPQ AEESREVSDR   97

*          *           *          *
R15   SRRRGRPCLP EWDNIVCWPL GAPGEVVAVP CPDYIYDFNH KGHAYRRCDR  150
Oko   SRLQDGFCLP EWDINVCWPA GVPGKVVAVP CPDYFYDFNH KGRAYRRCDS  147
Okh   SRLQDGFCLP EWDNIVCWPA GVPGKVVAVP CPDYFYDFNH KGRAYRRCDS  147
                 --------- B ----------

N          N  N   *       N
R15   NGSWEVVPGH NRTWANYSEC LKFMTNETRE REVFDRLGMI YTVGYSMSLA  200
Oko   NGSWELVPGN NRTWANYSEC VKFLTNETRE REVFDRLGMI YTVGYSISLG  197
Okh   NGSWELVPGN NRTWANYSEC VKFLTNETRE REVFDRLGMI YTVGYSISLG  197
                                                  ----------

R15   SLTVAVLILA YFRRLHCTRN YIHMHMFLSF MLRAASIFVK DAVLYSGFTL  250
Oko   SLTVAVLILG YFRRLHCTRN HIHMHLFVSF MLRAVSIFIK DAVLYSGVST  247
Okh   SLTVAVLILG YFRRLHCTRN YIHMHLFVSF MLRAVSIFIK DAVLYSGVST  247
      -- C --------                    ---------- D ----------

*
R15   DEAERLTEEE LHIIAQVPPP PAAAAVGYAG CRVAVTFFLY FLATNYYWIL  300
Oko   DEIERITEEE LRAFTE...P PPADKAGFVG CRVAVTVFLY FLTTNYYWIL  294
Okh   DEIERITEEE LRAFLT...P PPADKAGFVG CRVAVTVFLY FLTTNYYWIL  294
                                      --------- E --------    ---

R15   VEGLYLHSLI FMAFFSEKKY LWGFTLFGWG LPAVFVAVWV GVRATLANTG  350
Oko   VEGLYLHSLI FMAFFSEKKY LWGFTLFGWG LPAVFVAVWV TVRATLANTE  344
Okh   VEGLYLHSLI FMAFFSEKKY LWGFTLFGWG LPAVFVAVWV TVRATLANTE  344
      ---- F ----------                 -------- G --------
      *
R15   CWDLSSGHKK WIIQVPILAS VVLNFILFIN IIRVLATKLR ETNAGRCDTR  400
Oko   CWDLSSGNKK WIIQVPILAA IVVNFILFIN IIRVLATKLR ETNAGRCDTR  394
Okh   CWDLSSGNKK WIIQVPILAA IVVNFILFIN IIRVLATKLR ETNAGRCDTR  394
                 --------- H ----------

R15   QQYRKLLRST LVLVPLFGVH YTVFMALPYT EVSGTGWQIQ MHYEMLFNSF  450
Oko   QQYRKLLKST LVLMPLFGVH YIVFMATPYT EVSGILWQVQ MHYEMLFNSF  444
Okh   QQYRKLLKST LVLMPLFGVH YIVFMATPYT EVSGILWQVQ MHYEMLFNSF  444
                 --------- I ----------         ,        ------

R15   QGFFVAIIYC FCNGEVQAEI RKSWSRWTLA LDFKRKARSG SSSYSYGPMV  500
Oko   QGFFVAIIYC FCNGEVQAEI KKSWSRWTLA LDFKRKARSG SSTYSYGPMV  494
Okh   QGFFVAIIYC FCNGEVQAEI KKSWSRWTLA LDFKRKARSG SSTYSYGPMV  494
      -- J ----------

R15   SHTSVTNVGP RAGLSLPLSP RLPP...ATT NGHSQLPGHA KPGAPATETE  547
Oko   SHTSVTNVGP RGGLALSLSP RLAPGAGASA NGHHQLPGYV KHGSISENSL  544
Okh   SHTSVTNVGP RGG....... ....WPCPSA LD                    515

R15   TLPVTMAVPK DDGFLNGSCS GLDEEASGSA RPPPLLQEGW ETVM         591
Oko   PSSGPEPGTK DDGYLNG..S GLYEPMVG.E QPPPLLEEER ETVM         585
```

FIG. 5

With I enzymes: SACI          February 27, 1992 18:30

```
    GGGATCCCGCGGCCCTAGGCGGTGGCGAccGCccgatcgcacccggcctggcg
2   ||||||||||||||||||||||||||||||||||||||||||||||||||||  61
    CCCTAGGGCGCCGGGATCCGCCACCGCTggCGGgcctagcgtgggccgaccgc
                 M  G  T  A  R  I  A  P  G  L  A           - ctcctgctctgctgcccgtgctcagctccgcgtaccgctggtggatgcagatgacgtc
62  ||||||||||||||||||||||||||||||||||||||||||||||||||||||||| 121
    gaggacgagacgacgggcacgagtcgaggcgcatgcgaccacctacgtctactgcag
     L  L  L  C  C  P  V  L  S  S  A  Y  A  L  V  D  A  D  D  V  - atgactaaagaggaacagatcttcctgctgcaccgtgctcaggcccagtgcgaaaacgg
122 ||||||||||||||||||||||||||||||||||||||||||||||||||||||||| 181
    tactgattctcctTgtctagaagacgaccttcacgagtccgggtcacgctttttgcc
     M  T  K  E  E  Q  I  F  L  L  H  R  A  Q  C  E  K  R     - ctcaaggaggtcctgcagaggccagcagccagcataatgaatcagacaaggatggacatct
182 ||||||||||||||||||||||||||||||||||||||||||||||||||||||||| 241
    gagttcctccaggacgtccggtcgtcggtcgtattacctagtctgttccctacctgtaga
     L  K  E  V  L  Q  R  P  A  S  I  M  E  S  D  K  G  W  T  S  - gcgtccacatcaggaagcccaggaaagataaggcatctggaagctctaccctgagtct
242 ||||||||||||||||||||||||||||||||||||||||||||||||||||||||| 301
    cgcaggtgtagtcccttaggtccttctattccgtagaccctttcgagatgggactcaga
     A  S  T  S  G  K  P  R  K  D  K  A  S  G  K  L  Y  P  E  S  -
```

FIG. 6a

```
302 gaggaggacaaggaggaggcacccactggcagcaggaaccgagggcgccctgtctgccgaa    361
    ctcctcctgttcctccgtgggtgacctcgtcgtccttccatggctctccgcgggacagacggcctt   —
     E   E   D   K   E   A   P   T   G   S   -   .   R   G   R   P   C   L   P   E 362 tgggaccacatcctgtgctggccgctggggggccaccaggtgaggtggtggctgtgccctgt    421
    accctggtgtaggacacgacgaccggcgaccccgtggtccactccaccacgacacgggaca   —
     W   D   H   I   L   C   W   P   L   G   A   P   G   E   V   V   A   V   P   C 422 ccggactacatttatgacttcaatcacaaaggccatgcctaccgacgctgtgaccgcaat    481
    ggcctgatgtaaatactgaagttagtgttttccggtacggatggctgcgacactggcgtta   —
     P   D   Y   I   Y   D   F   N   H   K   G   H   A   Y   R   R   C   D   R   N 482 ggcagctgggagctggtgctgggcacaacaggacgtgggccaactacacagcgagtgtgtc    541
    ccgtcgaccctcgaccacgaccacgaccgttgttgtcctgcacccggttgatgtcgctcacacag   —
```

FIG. 6b

```
         G  S  W  E  L  V  P  G  H  N  R  T  W  A  N  Y  S  E  C  V
      aaatttctccaccaacgagactcgtgaacggggaggtgtttgaccgcctgggcatcatttac  601
542   ------------------------------------------------------------
      tttaagagtggttactctgagcacttgccctccacaaactggcgaccccgtactaaatg K  F  L  T  N  E  T  R  E  R  E  V  F  D  R  L  G  M  I  Y
      accgtgggctactccgtgtccctggcgtccctcaccgtagctgtgctcatcctgcctac   661
602   ------------------------------------------------------------
      tggcacccgatgaggcacaggaccgcaggagtggcatcgacacgagtaggaccggatg T  V  G  Y  S  V  S  L  A  S  L  T  V  A  V  L  I  L  A  Y
      tttaggcggctgcactgcacgcgcaactacatccacactgttcctgtccttcatg       721
662   ------------------------------------------------------------
      aaatccgccgacgtgacgtgcgcgttgatgtaggtgtgacaaggacaggaagtac F  R  R  L  H  C  T  R  N  Y  I  H  M  H  L  F  L  S  F  M
      ctgcgcgccgtgagcatcttcgtcaaggacgctgtgctctactctggccacgcttgat   781
722   ------------------------------------------------------------
      gacgcgcggcactcgtagaagcagttcctgcgacacgagatgagaccgcggtgcgaacta

```
782  gaggctgagcgcctcaccgaggagagctgcgcgccatcgcccaggcgcccccgcct  841
     ctccgactcgcggagtggctccctcgacgcggtagcggttccgcggggcggcgga  -
     E   A   E   R   L   T   E   E   E   L   R   A   I   A   Q   A   P   P   P   P 842  gccaccgccgctgccggctacgcggctgtccaggtggctgtgacctgtcttacttc  901
     cggtggcggcgacggccgatgcgcccgacgtcccaccgacactggaagaaggaaatgaag  -
     A   T   A   A   A   G   Y   A   G   C   R   V   A   V   T   F   F   L   Y   F 902  ctggccaccaactactactggattctggtggagggctgtacctgcacagcctcatcttc  961
     gaccggtggttgatgatgacctaagaccaccccccgacatggacgtgttggagtagaag  -
     L   A   T   N   Y   Y   W   I   L   V   E   G   L   Y   L   H   G   L   I   F 962  atggccttcttctcagagaagaagtacctgtgggcttcacagtcttcggctggggtctg  1021
     taccggaagaagagtctcttcttcatgacacaccccgaagtgtcagaagccgaccccagac  -
     M   A   F   F   S   E   K   K   Y   L   W   G   F   T   V   F   G   W   G   L 1022 cccgctgtcttcgtggctgtgtgggtcagtgtcagagctaccctggccaacaccgggtgc  1081
     gggcgacagaagcaccgacacaccccagtcacagtctcgatggaccggttgtggcccacg  -
     P   A   V   F   V   A   V   W   V   S   Y   R   A   T   L   A   N   T   G   C s
                                    a
                                    c
```

FIG. 6d

```
1082  tggacttgagctcccggaacaaaaagtggatcatccaggtgccatcctgcctccatt   1141
      ----------------------------------------------------------
      accctgaactcgaggccctttgttttcacctagcaggtccacggtaggaccggaggtaa

W  D  L  S  G  G  N  K  K  W  I  I  Q  V  P  I  L  A  S  I 1142  gtgctcaacttcatcctcttcatcaatatcgtccggtgctcgccaccaagcagcgggag   1201
      ----------------------------------------------------------
      cacgagttgaagtaggagaagtagttatagcaggccacgagcggtggttcgtcgccctc

V  L  N  F  I  L  F  I  N  I  V  R  V  L  A  T  K  Q  R  E 1202  accaacgccggccggtgtgacacacggcagcagtaccggaagctgctcaaatccacgctg   1261
      ----------------------------------------------------------
      tggttgcggccggccacactgtgtgccgtcgtcatggccttcgacgagttaggtgcgac

T  N  A  G  R  C  D  T  R  Q  Q  Y  R  K  L  L  K  S  T  L 1262  gtgctcatgcccctctttggcgtccactacattgtcttcatggccacaccatacaccgag   1321
      ----------------------------------------------------------
      cacgagtacgggggagaaaccgcaggtgatgtaacagaagtaccggtgtggtatgtggctc

V  L  M  P  L  F  G  V  H  Y  I  V  F  M  A  T  P  Y  T  E 1322  gtctcagggacgctctggcaagtccagatgcactatgagatgctcttcaactccttccag   1381
      ----------------------------------------------------------
      cagagtccctgcgagaccgttcaggtctcatactctacgagaagttgaggaaggtc

```
1382  ggattttttgtcgcaatcatatactgtttctgcaatggcgaggtacaagctgagatcaag  1441
      ||||||||||||||||||||||||||||||||||||||||||||||||||||||||||||
      cctaaaaaacagcgttagtatatgacaaagacgttaccgctccatgttcgactctagttc

G  F  F  V  A  I  I  Y  C  F  C  N  G  E  V  Q  A  E  I  K 1442  aaatcttggagccgctggacactggcactggacttcaagcgaaaggcacgcagcgggagc  1501
      ||||||||||||||||||||||||||||||||||||||||||||||||||||||||||||
      tttagaacctcggacctgtgaccgtgtgacctgaagttcgcttccgagcgtcgccctcg

K  S  W  S  R  W  T  L  A  L  I  F  K  R  K  A  R  S  G  S 1502  agcagctatagctacggcccatggtgtcccacacaagtgtgaccaatgtcggccccgt    1561
      ||||||||||||||||||||||||||||||||||||||||||||||||||||||||||
      tcgtcgatatcgatgccgggtaccacaggtgtgttcacactggttacagccggggca

S  S  Y  S  Y  G  P  M  V  S  H  P  S  V  T  N  V  G  P  R 1562  gtgggactcggcctgccctcagccccgcctactgccactgccaccaacggccac        1621
      ||||||||||||||||||||||||||||||||||||||||||||||||||||||
      cacccctgagccgacgggagtcggggcgatgacggtgacggtggttgccggtg

V  G  L  P  L  S  P  R  L  L  P  T  A  T  T  N  G  H 1622  cctcagctgcctgccatgccaagccaaggaccccagcccctgagaccctcgagaccaca   1681
      ||||||||||||||||||||||||||||||||||||||||||||||||||||||||||
      ggagtcgacggacgtacgttcggttccctgggtcccgggtcggaccctcggagctctggtgt

```
1682  ccacctgttatgctgctcccaaggacgatgggttcctcaacgctcctgctcaggcctg   1741
      ||||||||||||||||||||||||||||||||||||||||||||||||||||||||||
      ggtggacggtaccgaccaggttcctgctacccaaggagttgcgaggacgagtccggac
       P  P  A  M  A  A  P  K  D  D  G  F  L  N  G  S  C  S  G  L 1742  gacgaggaggcctctggcctgagcggccacctgccctgctacaggaagagtgggagaca   1801
      ||||||||||||||||||||||||||||||||||||||||||||||||||||||||||
      ctgctcctccggagaccggactcgccgtgacggacgatgtccttctcaccctctgt
       D  E  E  A  S  F  P  E  R  P  P  A  L  L  Q  E  E  W  E  T 1802  gtcatgtgaccaggcgctggggctgacctgctgacatagtgatggacagatggacca   1861
      ||||||||||||||||||||||||||||||||||||||||||||||||||||||||||
      cagtacactgtccgcgaccccgactgacgactgtatcactactgtctacctggt
       V  M 1862  aaagatggttgaatgatttccactcaggcctgggggccaagagaggaaaaacaggg   1921
      ||||||||||||||||||||||||||||||||||||||||||||||||||||||||||
      tttctaccaccaacttactaaaggtgagtccccggaccccggttctccttttgtccc 1922  gaaaaaagaaaaaagaaaaaaggaaaaaaaaaaaaaaaaaaaaaaaaaaaaaaaaaaaa   1981
      ||||||||||||||||||||||||||||||||||||||||||||||||||||||||||
      cttttttcttttttcttttttcctttttttttttttttttttttttttttttttttttt 1982  aaaaaaaaaaaaaaaaaaaaaaaaaa   2011
      ||||||||||||||||||||||||||
      tttttttttttttttttttttttttt Enzymes that do cut:

SacI
```

FIG. 6g

PARATHYROID HORMONE RECEPTOR

This application is a divisional of application Ser. No. 07/864,465 filed Apr. 6, 1992 now U.S. Pat. No. 5,261,686 which is a continuation of Ser. No. 07/681,702 filed Apr. 5, 1991 now abandoned.

Partial funding of the work described herein was provided by the U.S. Government, which has certain rights to the invention.

BACKGROUND OF THE INVENTION

The invention relates to endocrine receptors.

A crucial step in the expression of hormonal action is the interaction of hormones with receptors on the plasma membrane surface of target cells. The formation of hormone-receptor complexes allows the transduction of extracellular signals into the cell to elicit a variety of biological responses. For example, binding of a hormone such as follicle stimulating hormone (FSH), luteinizing hormone (LH), thyroid stimulating hormone (TSH), and chorionic gonadotropin (CG), to its cell surface receptor induces a conformational change in the receptor, resulting in the association of the receptor with a transductor molecule, the stimulatory guanine nucleotide (GTP) binding protein, a component of which is ($G_s$). This association stimulates adenylate cyclase activity which in turn triggers other cellular processes such as protein phosphorylation, steroid synthesis and secretion, and the modulation of ion flux. Binding of other hormones, including arginine vasopressin (VP), angiotensin II, and norepinephrine, to their cell surface receptors results in the activation of other types of GTP binding proteins components such as ($G_p$), which in turn stimulates the activity of the enzyme phospholipase C. The products of phospholipase C hydrolysis initiate a complex cascade of cellular events, including the mobilization of intracellular calcium and protein phosphorylation.

Parathyroid hormone (PTH) is a major regulator of calcium homeostasis whose principal target cells occur in bone and kidney. Regulation of calcium concentration is necessary for the normal function of the gastrointestinal, skeletal, neurologic, neuromuscular, and cardiovascular systems. PTH synthesis and release are controlled principally by the serum calcium level: a low level stimulates and a high level suppresses both the hormone synthesis and release. PTH, in turn, maintains the serum calcium level by directly or indirectly promoting calcium entry into the blood at three sites of calcium exchange: gut, bone and kidney. PTH contributes to net gastrointestinal absorption of calcium by favoring the renal synthesis of the active form of vitamin D. PTH promotes calcium resorption from bone by inhibiting osteoblasts and, indirectly, by stimulating differentiation of the bone-resorbing cells, osteoclasts. It also mediates at least three main effects on the kidney: stimulation of tubular calcium reabsorption, enhancement of phosphate clearance, and promotion of an increase in the enzyme that completes synthesis of the active form of vitamin D. PTH exerts these effects primarily through receptor-mediated activation of adenylate cyclase, although receptor-mediated activation of phospholipase C by PTH has also been reported (Hruska et al., J. Clin. Invest. 79:230, 1987).

Disruption of calcium homeostasis may produce many clinical disorders (e.g., severe bone disease, anemia, renal impairment, ulcers, myopathy, and neuropathy) and usually results from conditions which produce an alteration in the level of parathyroid hormone. Hypercalcemia is a condition which is characterized by an elevation in the serum calcium level. It is often associated with primary hyperparathyroidism in which an excess of PTH production occurs as a result of a lesion (e.g., adenoma, hyperplasia or carcinoma) of the parathyroid glands. Another type of hypercalcemia, humoral hypercalcemia of malignancy (HHM), is the most common paraneoplastic syndrome. It appears to result in most instances from the production by tumors (e.g., squamous, renal, ovarian or bladder carcinomas) of a novel class of protein hormone which shares amino acid homology with PTH. These PTH-related proteins (PTHrP) appear to mimic certain of the renal and skeletal actions of PTH and are believed to interact with the PTH receptor in these tissues. PTHrP is normally found at low levels in many tissues, including keratinocytes, brain, pituitary, parathyroid, adrenal cortex, medulla, fetal liver, osteoblast-like cells and lactating mammary tissues. In many HHM malignancies, PTHrP is found in the circulatory system at high levels, thereby producing the elevated calcium levels associated with HHM.

SUMMARY OF THE INVENTION

The invention features isolated DNA comprising a DNA sequence encoding a cell receptor, preferably a parathyroid hormone receptor, of a vertebrate animal, which receptor has an amino acid sequence with at least 30% (preferably at least 50%, even more preferably at least 60%, and most preferably at least 75%) identity to the amino acid sequence shown in FIG. 3 (SEQ ID NO.: 3): i.e., when the closest match is made between the two amino acid sequences (using standard methods), at least 30% of the amino acid residues of the former sequence are identical to the amino acid residues of the latter sequence. By "isolated" is meant that the DNA is free of the coding sequences of those genes that, in the naturally-occurring genome of the organism (if any) from which the DNA of the invention is derived, immediately flank the gene encoding the DNA of the invention. The isolated DNA may be single-stranded or double-stranded, and may be genomic DNA, cDNA, recombinant hybrid DNA, or synthetic DNA. It may be identical to a naturally-occurring, cell receptor- (e.g. PTH receptor) encoding DNA sequence, or may differ from such sequence by the deletion, addition, or substitution of one or more nucleotides. Single-stranded DNAs of the invention are generally at least 8 nucleotides long, (preferably at least 18 nucleotides long, and more preferably at least 30 nucleotides long) ranging up to full length of the gene or cDNA; they preferably are detectably labelled for use as hybridization probes, and may be antisense. Preferably, the isolated DNA hybridizes under conditions of high stringency to all or part of the DNA sequence show in FIGS. 1A–1C (SEQ ID NO.:1), FIGS. 2A–2C (SEQ ID NO.:2), FIGS. 3A–3C (SEQ ID NO.:3), or FIGS. 6A–6D (SEQ ID NO.:4). By "high stringency" is meant, for example, conditions such as those described herein below for the isolation of human kidney PTH receptor cDNA (also see Current Protocols in Molecular Biology, John Wiley & Sons, New York, 1989, hereby incorporated by reference). Most preferably, the animal is a mammal (such as an opossum, a rat, or a human), and the DNA sequence encodes substantially all of the amino acid sequence shown in FIGS. 1A–1C (SEQ ID NO.:1), FIGS. 2A–2C (SEQ ID NO.:2), FIGS. 3A–3C (SEQ ID NO.:3) or FIG. 6 (SEQ ID NO.:4); or is encoded by the coding sequence of one of the plasmids deposited with the American Type Culture Collection (ATCC) and designated ATCC Accession No. 68570 or 68571. The DNA of the invention may be incorporated into a vector [which may be provided as a purified preparation (e.g., a vector separated from the mixture of vectors which make up a library)] containing a DNA sequence encoding a cell receptor of the invention (e.g. parathyroid hormone receptor) or fragment of the receptor, and a cell or essentially homogenous population of cells (e.g., prokaryotic cells, or eukaryotic cells such as mammalian cells) which contain the vector (or the isolated DNA described above). By "essentially homogenous" is meant that at least 99% of the cells contain the vector of the invention (or the isolated DNA, as the case may be). Preferably, this vector (e.g., R15B) is capable of directing expression of a parathyroid hormone receptor (for example, in a cell transfected or transformed with the vector).

In another aspect, the invention features a cell receptor, preferably parathyroid hormone receptor, (or an essentially purified preparation thereof) produced by expression of a recombinant DNA molecule encoding the cell receptor. An "essentially purified preparation" is one which is substantially free of the proteins and lipids with which it is naturally associated.

In a related aspect, the invention features a polypeptide which includes a fragment of a naturally-occurring cell receptor of the invention. Preferably, the polypeptide includes a fragment of a naturally-occurring parathyroid hormone receptor which is capable of binding parathyroid hormone or parathyroid hormone-related protein. In preferred embodiments, this fragment is at least six amino acids long, and has a sequence selected from the group including:

(a) Thr Asn Glu Thr Arg Glu Arg Glu Val Phe Asp Arg Leu Gly Met Ile Tyr Thr Val Gly; (SEQ ID NO.: 5)

(b) Tyr Leu Tyr Ser Gly Phe Thr Leu Asp Glu Ala Glu Arg Leu Thr Glu Glu Glu Leu; (SEQ ID NO.: 6)

(c) Val Thr Phe Phe Leu Tyr Phe Leu Ala Thr Asn Tyr Tyr Trp Ile Leu Val Glu Gly; (SEQ ID NO.: 7)

(d) Tyr Xaa Arg Ala Thr Leu Ala Asn Thr Gly Cys Trp Asp Leu Ser Ser Gly His Lys Lys Trp Ile Ile Gln Val Pro; (SEQ. ID NO.: 8)

(e) Pro Tyr Thr Glu Tyr Ser Gly Thr Leu Trp Gln Ile Gln Met His Tyr Glu Met; (SEQ ID NO.: 9)

(f) Asp Asp Val Phe Thr Lys Glu Glu Gln Ile Phe Leu Leu His Arg Ala Gln Ala; (SEQ ID NO.: 10)

(g) Phe Phe Arg Leu His Cys Thr Arg Asn Tyr; (SEQ ID NO.: 11)

(h) Glu Lys Lys Tyr Leu Trp Gly Phe Thr Leu; (SEQ ID NO.: 12)

(i) Val Leu Ala Thr Lys Leu Arg Glu Thr Asn Ala Gly Arg Cys Asp Thr Arg Gln Gln Tyr Arg Lys Leu Leu Lys; or (SEQ ID NO. 13)

(j) a fragment (i.e., a portion at least six residues long, but less than all) or analog of (a)–(i) which is capable of binding parathyroid hormone or parathyroid hormone-related protein [wherein "analog" denotes a peptide having a sequence at least 50% (and preferably at least 70%) identical to the peptide of which it is an analog].

Preferably, the polypeptide of the invention is produced by expression of a recombinant DNA molecule or is synthetic (i.e., assembled by chemical rather than biological means). The invention provides a method for producing such a polypeptide, which method includes providing a cell containing isolated DNA encoding a cell receptor of the invention or receptor fragment and culturing this cell under conditions which permit expression of a polypeptide from the isolated DNA.

The invention also features an antibody (monoclonal or poylclonal), and a purified preparation of an antibody, which is capable of forming an immune complex with a cell receptor of the invention (preferably a parathyroid hormone receptor such as a human PTH receptor) such antibody being generated by using as antigen either (1) a polypeptide that includes a fragment of the cell receptor of the invention, or (2) a cell receptor of the invention which is on the surface of a cell. This antibody is preferably capable of neutralizing (i.e., partially or completely inhibiting) a biological activity of the cell receptor of the invention (i.e., a component of one of the cascades naturally triggered by the receptor when its ligand binds to it). In preferred embodiments, the antibody of the invention is capable of forming an immune complex with parathyroid hormone receptor and is capable of neutralizing a biological activity of the PTH receptor (i.e. adenylate cyclase activation or phospholipase C stimulation)

Also within the invention is a therapeutic composition including, in a pharmaceutically-acceptable carrier, (a) a cell receptor of the invention, (b) a polypeptide containing a fragment of the cell receptor of the invention, or (c) an antibody to a cell receptor of the invention. These therapeutic compositions provide a means for treating various disorders characterized by overstimulation of the cell receptors of the invention by their ligand. In preferred embodiments, the polypeptides of the invention include the PTH receptor, fragments of the PTH receptor and antibodies which form immune complexes with the PTH receptor. These polypeptides and antibodies are useful as diagnostics, for distinguishing those cases of hypercalcemia related to PTH or PTHrP from those which are not.

The nucleic acid probes of the invention enable one of ordinary skill in the art of genetic engineering to identify and clone cell receptor homologs or cell receptors from any species which are related to the cell receptors of the invention, expanding She usefulness of the sequences of the invention.

Other features and advantages of the invention will be apparent from the following description of the preferred embodiments and from the claims.

DETAILED DESCRIPTION

The drawings will first be briefly described.

DRAWINGS

FIG. 1 is a representation of the nucleic acid (SEQ ID NO.: 1) and amino acid (SEQ ID NO.: 18) sequences for the opossum kidney PTHrP receptor clone, OK-H.

FIG. 2 is a representation of the nucleic acid (SEQ ID NO.: 2) and amino acid (SEQ ID NO.: 19) sequences for the opossum kidney PTH/PTHrP receptor clone, OK-O.

FIG. 3 is a representation of the nucleic acid (SEQ ID NO.: 3) and amino acid (SEQ ID NO.: 20) sequences for the rat bone PTH/PTHrP receptor clone, R15B.

FIG. 4 is a comparison of the deduced amino acid sequences of R15B (SEQ ID NO:20) (top line) and OK-O (SEQ ID NO:19) (bottom line) encoded by cDNAs from clones OK-O and R15B (SEQ ID NO:3 and SEQ ID NO:2, respectively).

FIG. 5 is a comparison of the deduced amino acid sequences of OK-O (SEQ ID NO:19), OK-H (SEQ ID NO:18) and R15B (SEQ ID NO:20), lined up according to sequence homology.

FIG 6 is a representation of the nucleic acid (SEQ ID NO.: 4) and amino acid (SEQ ID NO.21:) sequences for the human PTH/PTHrP receptor.

MATERIALS AND METHODS

GENERAL

Figure 7:
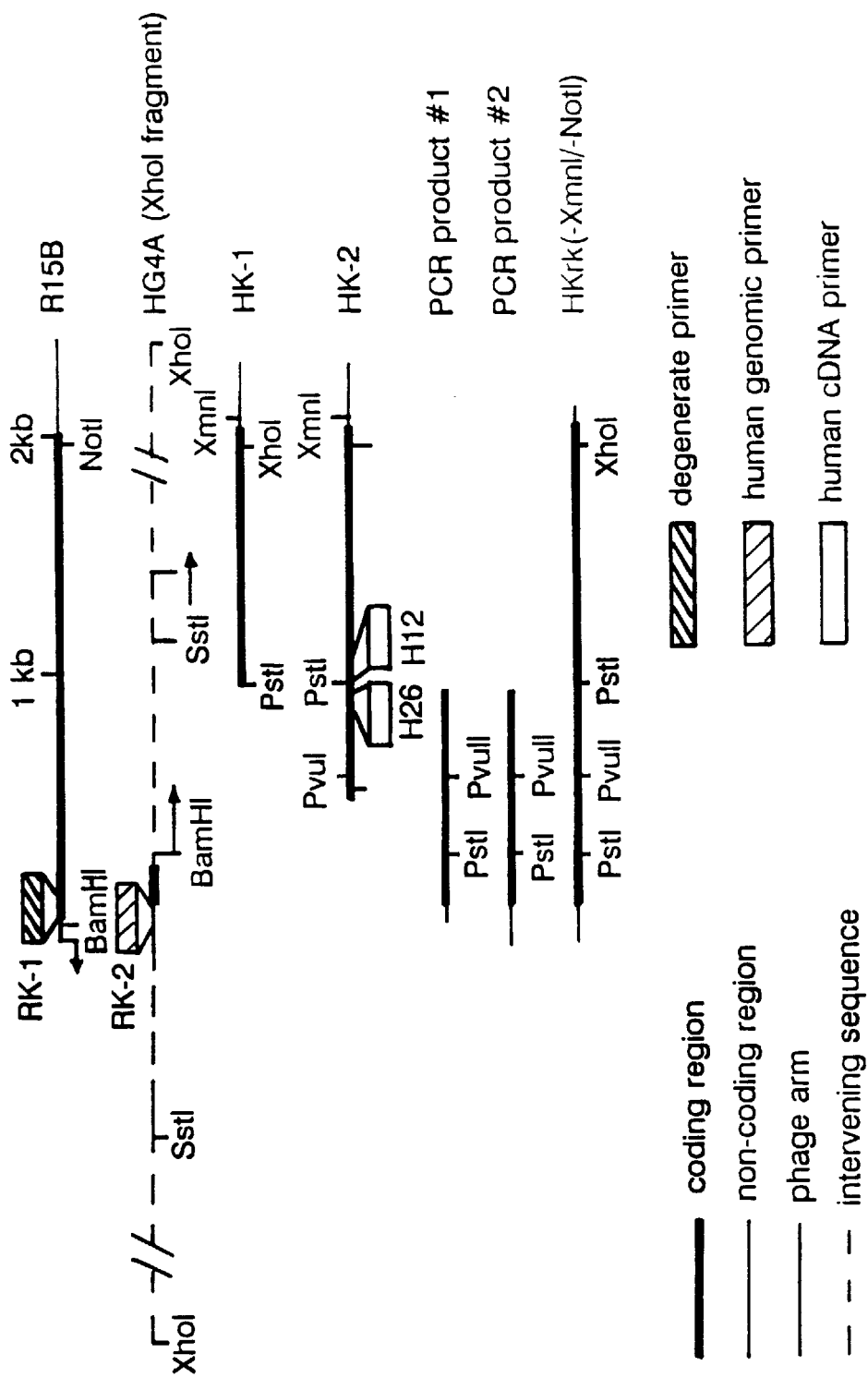
FIG. 7 is a schematic representation of the rat bone PTH/PTHrP receptor cDNA, the human genomic DNA clone HPG1 and two cDNA clones encoding the human PTH/PTHrP receptor.

[Nle$^{8,18}$, Tyr$^{34}$]bPTH(1–34)amide (PTH(1–34)), [Nle$^{8,18}$, Tyr$^{34}$]bPTH(3–34)amide (PTH(3–34)), and [Nle$^{8,18}$, Tyr$^{34}$] bPTH(7–34)amide (PTH(7–34)) were obtained from Bachem Fine Chemicals, Torrance, Calif.; [Tyr$^{36}$]PTHrP (1–36)amide (PTHrP(1–36)) was synthesized as described (Keutman et al., Endocrinology 117:1230, 1985) using an Applied Biosystems Synthesizer 420A. Dulbecco's modified Eagles medium (DMEM), EDTA/trypsin, and gentamycin were from GIBCO (Grand Island, N.Y.); fetal bovine serum (FBS) was from Hiclone Laboratory, Logan, Utah. Total RNA from human kidney was provided by Per Hellman, University Hospital, Uppsala, Sweden. Oligonucleotide primers were synthesized using an Applied Biosystems 380B DNA Synthesizer. Restriction enzymes, Klenow enzyme, T4 polynucleotide Kinase and T4 DNA ligase were from New England Biolabs, Beverly, Mass. Calf alkaline phosphatase was from Boehringer Mannheim, Germany. All other reagents were of highest purity available.

CELLS

Cell lines used include COS cells, OK cells, SaOS-2 cells, CHO cells, AtT20 cells, LLC-PK1 cells, and UMR-106 cells, which are available from a variety of sources including the American Type Culture Collection (Rockland, Md.), Accession Nos. CRL1650, CRL6551, HTB85, CCL61, CCL89, CL101, and CRL1161, respectively. ROS 17/2 and ROS 17/2.8 are available from a number of sources including Dr. Gideon Rodan (Merck Laboratories, West Point, Pa.). MC-3T3 cells are derived from mouse bone cells and are also available from a number of sources including Dr. Chohei Shigeno (Dept. of Biochem. Medicine, Hyoto Univ., Kyoto, Japan).

All cells were grown in a humidified 95% air, 5% $CO_2$ atmosphere and maintained in monolayer culture with Ham's F-12 or DMEM medium (Grand Island Biological Co.), supplemented with 5% or 10% fetal calf serum (M.A. Bioproducts, Walkersville, Md.). The medium was changed every 3 or 4 days, and the cells were subcultured every 2 or 3 weeks by trypsinization using standard methods.

CLONING

Isolation of cDNA clones encoding the rat and opossum PTH/PTHrP receptors: Total RNA was initially isolated from rat osteosarcoma (ROS) cells (ROS 17/2.8) and opossum kidney (OK) cells, by standard methods using guanidium isothiocyanate (Ullrich at al., Science 196: 1313, 1977; Chirgwin et al. Biochemistry 24: 5294, 1979), and centrifugation through cesium chloride (Gilsen et al., Biochemistry 13: 2633, 1974). Poly A+ RNAs (mRNAs) were then recovered after passage of the total RNAs over oligo dT columns (Pharmacia, Piscataway, N.J.) by the method of Aviv and Leder (Proc. Natl. Acad Sci. U.S.A. 69: 14087, 1972). The cDNA library from the ROS 17/2.8 mRNA was prepared from poly A+ RNA using the method of Gubler and Hoffman (Gene (Amst.) 25: 263, 1983). Oligo dT-primed and random-primed cDNAs were synthesized from poly A+ ROS 17/2.8 and OK cell mRNA, respectively (Aviv and Leder, supra). The cDNAs were ligated to BstX1 linkers (Invitrogen, San Diego, Calif.) and size-selected by centrifugation (3 h, 55,000 xg) in a 5–20% potassium acetate gradient. The size-selected cDNA was then inserted into the plasmid vector, pcDNA I (Invitrogen), using the non-self annealing BstXl restriction sites. The resultant plasmid libraries were then used to transform E. coli (MC1061/P3, Invitrogen) containing a larger helper plasmid, p3. The p3 plasmid possesses amber mutations in two genes which code for ampicillin and tetracycline resistance. Using ampicillin and tetracycline selection, only those cells containing both the p3 and a tRNA suppressor gene, which is contained within pcDNA I, were capable of growth. The transformed bacteria were then grown to confluence, and the plasmid DNAs isolated using standard techniques (e.g., see Ausebel et al., Current Protocols in Molecular Biology, John Wiley Sons, New York, 1989). These DNAs were then taken up in a DEAE-dextran solution, and used to transfect African Green Monkey kidney (COS) cells, which had been grown to 75% confluence in "sideflasks" (Nunc, Denmark).

Screening for COS cells containing plasmids capable of expressing functionally-intact ROS or OK cell parathyroid hormone/parathyroid hormone related-protein (PTH/PTHrP) receptor proteins was performed according to Gearing et al. (EMBO J. 8: 3676, 1989), with some minor modifications including DEAE-Dextran transfection in sideflasks. Forty-eight hours after transfection, the cells were tested for binding of $^{125}$I-labeled [Tyr$^{36}$]PTHrp (1–36) amide, using methods previously described (Yamamoto et al., Endocrinology 122: 1208, 1988), with the following exceptions: the time and temperature of the incubation were 2 h and room temperature, respectively. After rinsing, the cells were fixed with 1.25% glutaraldehyde, and rinsed with 1% gelatin. After snapping off the top of the sideflask, the remaining microscope slide was dipped into NTB-2 photographic emulsion (Eastman Kodak, Rochester, N.Y.). After 3–4 days of exposure at 4° C., the slides were developed, fixed, and stained with 0.03% toluene blue. Screening of each slide was performed under a light microscope (Olympus). One pool of plasmid-DNA from ROS cells, and two pools of plasmid-DNA from OK cells, (10,000 independent clones), each gave rise to 3–4 transfected COS cells expressing the PTH/PTHrP receptor. These pools were subsequently subdivided. The subpools were used to transfect COS cells, and single clones were identified that expressed receptor protein capable of binding the radioligand.

Isolation of cDNA and genomic DNA clones encoding the human PTH/PTHrP receptor: A human kidney oligo dT-primed cDNA library (1.7×10$^6$ independent clones) in lambda GT10 and a genomic library of human placental DNA (2.5×10$^6$ independent clones) in EMBL3 (Sp6/T7) (Clontech, Palo Alto, Calif.) were screened by the plaque hybridization technique (Sambrook et al., Molecular Cloning: A Laboratory Manual, 2nd Ed. pp. 108–113, Cold Spring Harbor Laboratory, Cold Spring Harbor, N.Y., 1989) with the $^{32}$P-labelled (random primed labelling kit Boehrinaer Mannheim, Germany) BamHI/NotI 1.8 kb restriction enzyme fragment encoding most of the coding sequence of the rat bone PTH/PTHrp receptor (FIG. 3). The nitrocellulose filters were incubated at 42° C. for 4 hrs in a prehybridization solution containing 50% formamide, 4× saline sodium citrate (SSC; $^1$× SSC: 300 mM NaCl, 30 mM NaCitrate, pH 7.0), 2× Denhardt's solution, 10% Dextran sulphate, 100 μg/ml salmon sperm DNA (final concentration). The hybridizations were carried out in the same solution at 42° C. for 18–24 h. Filters were washed with 2× SSC/0.1% SDS for 30 minutes at room temperature and then with $^1$× SSC/0.1% SDS for 30 minutes at 45° C. The films were exposed at –80° C. for 18–24 h using intensifying screens.

About 1,000,000 clones were screened from each library. Positive clones were plaque-purified and lambda phage DNA was isolated (Sambrook et al., supra). Cloned inserts were removed from phage DNA by digestion with restriction endonucleases HindIII and EcoRI (lambda GT10 library), or with XhoI and SstI (EMBL3 library), and were then subcloned into pcDNAI (Invitrogen, San Diego, Calif.) using the appropriate, dephosphorylated restriction sites. Sequencing of the CsCl$_2$-purified subclones was performed according to Sanger et al. (Biochem 74:5463, 1977) by the dideoxy termination method (Sequenase version 2 sequencing kit, United States Biochemical Corporation, Cleveland, Ohio).

Reverse transcription and polymerase chain reaction (PCR): 3 μg of poly (A)+ RNA from human kidney (Clontech, Palo Alto, Calif.) in 73.5 μl of H$_2$O was incubated at 100° C. for 30 seconds, quenched on ice, and then added to 20 μl of 5× RT buffer (1× RT buffer: 40 mM Tris-HCl, pH 8.2, 40 mM KCl, 6.6 mM MgCl$_2$, 10 mM dithiothreitol, and dNTPs at 0.5 mM each), 2 μl (4 units) RNasin (Promega Biotec, Madison, Wis.), 1 μl (80 pmo/μl) of the human cDNA primer H12 (5'-AGATGAGGCTGTGCAGGT-3'; SEQ ID NO.: 14) and 80 units of avian myeloblastosis virus reverse transcriptase (Life Sciences, St. Petersburg, Fla.). The reaction mixture was incubated for 40 minutes at 42° C. One-tenth of the first strand synthesis reaction mixture was then amplified by PCR in a final volume of 100 μl containing 3 mM MgSO$_4$, 200 μM dNTPs, 2 units of Vent polymerase (New England Biolab, Beverly, Mass.), and 2 μM each of the forward and the reverse primers (PCR conditions: denaturing for 1 min at 94° C., annealing for 1 min at 50° C., and extension at 72° C. for 3 minutes; 40 cycles).

Two independent PCRs were performed using two different forward primers: i) degenerate primer RK-1

(5'-GGAATTCCATGGGAGCGGCCCGGAT-3';
G     CC

SEQ ID NO.: 15) based on the 5' coding end of the two previously cloned PTH/PTHrP receptors (described above), and ii) primer RK-2 (5'-CGGGATCCCGCGGCCCTAGGCGGT-3'; SEQ ID NO.: 16) based on the 5' untranslated region of the human genomic clone HPG1. Both PCR reactions used the reverse primer H26 (5'-AGTATAGCGTCCTTGACGA-3'; SEQ ID NO.: 17) representing nucleotides 713 to 731 of the coding region of the human PTH/PTHrP receptor (FIG. 4). PCR products were blunt-ended using Klenow enzyme and cloned into dephosphorylated pcDNAI cut with EcoRV.

Northern blot analysis: Total RNA was extracted from SaOS-2 cells and from human kidney by the guanidine thiocyanate method (Chirgwin et al., Biochem. 18:5294, 1979). For Northern blot analysis, ~10 μg of total RNA was subjected to electrophoresis on a 1.5%/37% formaldehyde gel and blotted onto nitrocellulose filters (Schleicher and Schuell, Keene, N.H.). The hybridization conditions were the same as those for screening the phage libraries (see above). The filters were washed at a final stringency of 0.5× SSC/0.1% SDS for 30 min at 60° C. and exposed for autoradiography.

Southern blot analysis: Human genomic DNA was prepared using the SDS/proteinase K method (Gross-Bellard et al., Eur. J. Biochem. 36:32, 1973). For Southern analysis, ~10 μg of DNA was digested with SstI, PvuII and XhoI; subjected to electrophoresis on a 0.8% agarose gel; and blotted onto nitrocellulose membranes (Schleicher and Schuell, Keene, N.H.). The hybridization conditions were the same as those for screening the phage libraries (see above). The filters were washed at a final stringency of 0.5× SSC/0.1% SDS for 30 min at 55° C. and exposed for autoradiography.

FUNCTIONAL ASSAYS

Tests to characterize the functional properties of the cloned receptors expressed on COS cells included:

I) binding of PTH and PTHrP fragments and analogues,

II) stimulation of cyclic AMP accumulation by PTH and PTHrP fragments and analogues, III) increase of intracellular free calcium by PTH and PTHrP fragments and analogues, and IV) activation of inositol phosphate metabolism by PTH and PTHrP fragments and analogues. The methodologies are as follows:

Radioreceptor Assay

[Nle$^8$,Nle$^{18}$,Tyr$^{34}$]bPTH-(1–34)amide (NlePTH), and [Tyr$^{36}$]PTHrP(1–36)amide(PTHrP) were iodinated with Na$^{125}$I (carrier free, New England Nuclear, Boston, Mass.) as previously reported (Segre et al., J. Biol. Chem. 254: 6980, 1979), and purified by reverse-phase HPLC. In brief, the labeled peptide was dissolved in 0.1% trifluoracetic acid (TFA), applied to a $C_{18}$ Sep-pak cartridge (Waters Associates, Inc., Milford, Mass.) and eluted with a solution of 60% acetonitrile in 0.1% TFA. After lyophilization, the radioligand then was applied to $C_{18}$-$\mu$Bondapak column (3.9 mm×30 cm. Waters Associates) and eluted over 30 min with a linear gradient of 30–50% acetonitrile-0.1% TFA at a flow rate of 2 ml/min. The radioligand eluted in two peaks; the first peak, which eluted at approximately 38% acetonitrile, was used in these studies because it gave higher total and specific bindings. The specific activity was 500±75 mCi/mg, which corresponds to an average iodine-peptide ratio of 1.

COS-7 cells were grown in 15 cm plates in DMEM, 10% heat-inactivated FBS, 10 mg/L gentamycin until 80–90% confluent. Twenty-four hours after transfection by the DEAE/Dextran method (Sambrook et al., supra), with 1–2 $\mu$g of plasmid DNA, the cells were trypsinized and replated in multiwell plastic dishes (16 or 35 mm diameter, Costar, Cambridge, Mass.) at a cell concentration of 5×10$^4$ cells/cm$^2$). Cell number increased only slightly after transfection. After continuing culture for another 48 h, radiorecepter assays were performed. The culture medium was replaced with buffer containing 50 mM Tris-HCL (pH 7.7), 100 mM NaCl, 2 mM CaCl$_2$, 5 mM KCL, 0.5% heat-inactivated fetal bovine serum (GIBCO), and 5% heat-inactivated horse serum (KC Biological Inc., Lenexa, Kans.) immediately before studies were initiated. Unless otherwise indicated, studies were conducted with cells incubated in this buffer at 15° C. for 4 h with 4×10$^5$ cpm/ml (9.6×10$^{11}$M) of $^{125}$I-labeled NlePTH or PTHrP.

Incubations were terminated by aspirating the buffer, and repeatedly (×3) washing the culture dishes containing the adherent cells with chilled 0.9% NaCl solution, over a 15 sec period. Cell-bound radioactivity was recovered by the sequential addition (×3) of 1N NaOH (200 $\mu$l) to each well. After 30 min at room temperature, the NaOH was transferred to a glass tube. A second and third extraction with 1N NaOH (200 $\mu$l) were combined with the first, and the total radioactivity was counted in a $\gamma$-spectrometer (Packard Instruments, Downers Grove, Ill.). Tracer adherence to culture vessel without cells was negligible (<0.2% of total counts added), if vessels were preincubated with culture medium.

Determinations of cAMP accumulation

Intracellular cAMP accumulation was measured as described previously (Abou-Samra et al., J. Biol. Chem. 262:1129, 1986). Cells in 24-well plates were rinsed with culture medium containing 0.1% BSA and 2 mM IBMX. The cells were then incubated with PTH or PTHrP for 15 min. at 37° C. The supernatant was removed and the cells immediately frozen by placing the whole plate in dry ice powder. Intracellular cAMP was extracted by thawing the cells in 1 ml of 50 mM HCl and analyzed by a specific radioimmunoassay using an anti-cAMP antibody (e.g., Sigma, St. Louis, Mo.). A cAMP analog (2'-O-monosuccinyl-adenosine 3':5'-cyclic monophosphate tyrosyl methyl ester, obtained from Sigma) which was used a tracer for cAMP was iodinated by the chloramine T method. Free iodine was removed by adsorbing the iodinated cAMP analog onto a C18 Sep-pak cartridge (Waters, Milford, Mass.). After washing with dH$_2$O, the iodinated cAMP analog was eluted from the Sep-pak Cartridge with 40% acetonitrille (ACN) and 0.1% trifluoroacetic acid (TFA). The iodinated cAMP analog was lyophilized, reconstituted in 1 ml 0.1% TFA, and injected into a C18 reverse phase HPLC column (Waters). The column was equilibrated with 10% ACN in 0.1% TFA, and eluted with gradient of 10–30% ACN in 0.1% TFA. This allows separation of the mono-iodinated cAMP analog from the non-iodinated cAMP analog. The tracer is stable for up to 4 months when stored at −20° C. The standard used for the assay, adenosine 3':5'-cyclic monophosphate, was purchased from Sigma. Samples (1–10 $\mu$l of HCl extracts) or standards (0.04–100 fmol/tube) were diluted in 50 mM Na-acetate (pH 5.5), and acetylated with 10 $\mu$l of mixture of triethylamine and acetic anhydride (2:1 vol:vol). After acetylation, cAMP antiserum (100 $\mu$l) was added from a stock solution (1:4000) made in PBS (pH 7.4), 5 mM EDTA and 1% normal rabbit serum. The tracer was diluted in PBS (pH 7.4) with 0.1% BSA, and added (20,000 cpm/tube). The assay was incubated at 40° C. overnight. The bound tracer was precipitated by adding 100 $\mu$l of goat anti-rabbit antiserum (1:20 in PBS) and 1 ml of 7% polyethyleneglycol (MW 5000–6000), centrifuging at 2000 rpm for 30 min. at 4° C. The supernatant was removed and the bound radioactivity was counted in a $\gamma$-counter (Micromedic). Standard curves were calculated using the four-parameter RIA program supplied by Micromedic. Typically, the assay sensitivity is 0.1 fmol/tube, and the standard concentration that displaces 50% of tracer is 5 fmol/tube.

In an alternative method for assaying cAMP accumulation, COS cells transfected with PTH/PTHrP receptor cDNA are harvested with a plastic policeman into a solution containing 10 mM Tris-HCl (pH 7.5), 0.2 mM MgCl, 0.5 mM ethyleneglycolbis($\beta$-amino ethyl ether) N,N'-tetra-acetic acid (EGTA) (Sigma) and 1 mM dithiothreitol (Sigma). Cells are homogenated by 20 strokes of tightly-fitting Dounce homogenizer, and centrifuged at 13,000× g for 15 min at 4° C. (Eppendorf, type 5412, Brinkmann Instruments, Inc., Westburg, N.Y.). The pellet Containing the plasma membranes is resuspended in the same buffer by several strokes with a Dounce homogenizer, and further diluted with the same buffer to a protein concentration of approximately 1.2 mg/ml, as determined by the method of Lowry et al. (Lowry et al., J. Biol. Chem 193: 265, 1951). Approximately 30 $\mu$g (25 $\mu$l) membrane are incubated with varying concentrations of hormone or vehicle alone for 10 min at 37° C. (final volume, 100 $\mu$l) in 50 mM Tris-HCl (pH 7.5), 0.8 mM ATP, 4×10$^6$ cpm [$\alpha$-$^{32}$P] ATP (New England Nuclear, Boston, Mass.), 9 mM theophylline, 4.2 mM MgCl$_2$, 26 mM KCl, 0.12% BSA, and an ATP-regenerating system containing 5 mM creatine phosphate (Schwartz/Mann Division, Becton-Dickenson & Co., Orangeburg, N.Y.) and 0.1 mg/ml creatine phosphokinase (Shwartz/Mann). Incubations are initiated by addition of the membrane suspension and terminated by addition of 100 $\mu$l of a solution containing 20 mM cAMP, approximately 50,000 cpm [$^3$H]cAMP, and 80 mM ATP. The reaction mixture is boiled, and the [$^{32}$P]cAMP generated is purified by sequential chromatography on ion-exchange columns (Dowex 50 W-X4, Biorad Lab, Richmond, Calif.) and alumina (Sigma). The [$^{32}$P]cAMP may be counted in a β-scintillation counter (Packard Instrument Co.), with correction for recovery of [$^3$H]cAMP.

Determination of intracellular free calcium

Measurements of intracellular calcium levels in cells transfected with PTH/PTHrP receptor cDNAs were performed using Fura-2 AM (acetomethoxy ester of Fura-2, Molecular Probes Inc., Eugene, Oreg.) loaded cells. Details of the methodology are:

Coverslips plated with COS cells were incubated in Fura-2 AM loading buffer containing, in mM: HEPES (N-[2-Hydroxyethyl]piperazine-N'-[2-ethanesulfonic acid]), 20; CaCl$_2$, 1; KCl 5; NaCl, 145; MgSO$_4$, 0.5; NaHCO$_3$, 25; K$_2$HPO$_4$, 1.4; glucose, 10; and Fura-2 AM 91-(2-5'-carboxyoxazol-2'-yl)-6-aminobenzofuran-5oxy-(2'-amino-5'-methylphenoxy)ethane-N,N,N',N'-tetraaecetic acid acetomethoxy ester), 0.5; at 37° C. at pH7.4, aerated with 95% air and 5% CO$_2$ for 45 minutes. Cells loaded with Fura-2 AM were then washed with a modified Krebs-Heinseleit (KH) buffer containing, in mM: HEPES, 20; CaCl$_2$, 1; KCl, 5; NaCl, 145; MgSO$_4$, 0.5; Na$_2$HPO$_4$, 1; glucose, 5; pH7.4. To check that cleavage of the ester occurred, the excitation spectra after different times of Fura-2 AM incubation were measured. At 5 min. after the start of incubation, the excitation spectrum peaked at approximately 360 nm, reflecting incomplete hydrolysis of Fura-2 AM, whereas beyond 30 min. the excitation spectrum peaked at 345 nM, characteristic of Fura-2.

To measure fluorescence of individual cells, the cover slips were placed in a microscope tissue chamber (Biophysica Technologies, Inc., Maryland). The chamber consisted of a shallow, sloped compartment made of Teflon with a silicone rubber seal. The cover slips served as the bottom of the chamber. A heater/cooler ring was encased in the silicone rubber which sealed the coverslip in place. Temperatures were varied between 22° C. and 37° C. by applying 0–7.4 V to the heater. If the temperature is not specifically stated, the experiment was performed at 37° C. The chamber was mounted on the stage of an inverted microscope (Zeiss IM-35, Thornwood, N.Y.). Fura-2 fluorescence was excited with a 75 watt Xenon arc lamp placed at the focal point of a condenser (Photon Technologies International (PTI) Inc., New Jersey). Grating monochromators, alternated by a rotating chopper in which mirror vanes alternate with transmitting sectors, were used for selecting wavelengths. The monochromator outputs were combined to form a common optical path which exited the source housing through an adjustable iris. The light then passed through quartz lenses and a dichroic mirror through a 100× Nikon Fluor objective. A photon-counting PMT device detection was used to measure the light output. Data analysis was performed using PTI software run on an IBM-compatible AT/286 computer using the MS-DOS operating system. Data was retained and manipulated in a packed binary format.

Intracellular calcium concentrations were calculated according to the formula: $[Ca^{2+}]i=K_d(R-Rmin)/(Rmax-R)B$, where R is the ratio of fluorescence of the cell at 340 and 380 nm; Rmax and Rmin represent the ratios of Fura-2 fluorescence intensity at 340 and 380 nm excitation wavelengths in the presence of a saturating amount of calcium and effectively zero calcium, respectively; B is the ratio of fluorescence of Fura-2 at 380 nm in zero calcium to that in saturating amounts of calcium; and $K_d$ is the dissociation constant of Fura-2 for calcium. To determine Rmax, at the end of an experiment ionomycin was added to the Fura-2 AM loaded cells to equilibrate Ca$^{2+}$ between the extracellular (1 mM) and intracellular environments. To calculate Rmin, 1 mM EGTA was then added to the bathing solution. Different dissociation constants were used at the different temperatures: 224 nM at 34°–37° C. and 135 nM at 24°–27° C.

Determination of inositol phosphate

The level of inositol phosphate metabolism was determined in COS cells transfected with PTH/PTHrP receptors using previously published methods (Bonventre, et al., J. Biol. Chem. 265: 4934, 1990).

RESULTS

Molecular characterization

Two independent clones (OK-H and OK-O), both of which were isolated from the OK cell cDNA library, had lengths of approximately 2 kilobases. The determined nucleotide sequence and predicted amino acid sequence of these clones are shown in FIGS. 1 (SEQ ID NO.:1) and 2 (SEQ ID NO.:2) respectively. The R15B clone isolated from the ROS cell cDNA library had a length of approximately 4 kilobases. The determined nucleotide sequence and predicted amino acid sequence of the rat bone PTH/PTHrP receptor is depicted in FIG. 3 (SEQ ID NO.:3).

The three cDNA clones appear to be full-length by the criteria of having codons encoding methionine residues that are predicted to be the likely candidates as initiator methionines. These methionine codons are followed by amino acid sequences (deduced from the DNA) with properties suggesting that they are "signal-peptide" sequences. All three receptor cDNAs have stop codons at locations that permit these receptors to "fit" a putative seven-membrane spanning model, a model typical for G-protein-linked receptors. Most importantly, all three cloned receptors bind ligands and, when activated, are capable of activating intracellular effectors. These properties suggest that all three of the isolated clones encode full-length cDNAs.

FIG. 4 demonstrates the high degree of homology between the amino acid sequences encoded by the cDNAs from OK-O and ROS 15B. There is an overall 87% homology and a 77.8% amino acid identity between these two receptors. This high level of identity over long stretches of amino acids demonstrates that the amino acid sequence of the PTH receptor is evolutionarily conserved to a high degree. This allows the data from both OK-O and R15B to be extrapolated to other species, including human.

FIG. 5 shows the deduced amino acid sequences of all three cloned cDNAs lined up according to sequence homology. The OK-H sequence is identical to OK-O except in the C-terminus tail, where the OK-O sequence totals 585 amino acids whereas the OK-H sequence stops at 515 amino acids. This difference is attributable to a single nucleotide (G) deleted in the OK-H sequence compared to the OK-O sequence, causing a frame shift and early stop codon in the former. It is not known whether OK-O and OK-H represent the products of two separate genes or of a laboratory artifact.

Some G-protein-coupled receptors are encoded by intronless genes (Kobilka et al., Nature 329:75, 1987); Kobilka et al., J. Biol. Chem. 262:7321, 1987; Heckert et al., Mol. Endocrinol. 6:70, 1992; Kobilka et al., Science 238:650, 1987; Bonner et al., Science 237:527, 1987; Sunahara et al., Nature 347:80, 1990). To isolate a human PTH/PTHrP receptor cDNA, both a human cDNA library and a human genomic library were screened with a probe (BamHI/NotI) representing most of the coding region of the rat bone PTH/PTHrP receptor (FIG. 3). Screening the human kidney cDNA library led to the isolation of the clone HK-1 (FIG. 6) [SEQ ID NO.: 6]. Since one of the two EcoRI cloning sites of lambda GT10 proved to be eliminated as a result of the library construction, the HindIII/EcoRI phage fragment containing the cDNA insert and ~250 bp of the 37 kb (left) lambda arm was subcloned into the corresponding restriction sites in pcDNAI. DNA sequencing revealed that the cloned cDNA contained ~1000 bp of the 3' coding region and ~200 bp of the 3' non-coding region including an A-rich 3' end. The coding region 5' to the XhoI site was subsequently used to re-screen the library and led to the isolation of the clone HK-2 which, after subcloning into pcDNAI, proved to contain ~1400 bp of the coding region. For the third screening of the library, the PvuII/PstI fragment of HK-2 was used; the isolated clone HK-3 proved to be identical to HK-2.

The genomic library screening (~10$^6$ pfu) resulted in the isolation of four independent clones. Comparison of Southern blot analyses of restriction enzyme digests of these clones with that of normal genomic DNA, revealed that one 15 kb genomic clone, HPG1 (also referred to as HG4A), contained a SstI/SstI fragment that had the same size as one hybridizing DNA species from normal human genomic DNA digested with SstI (see below). The hybridizing 2.3 kb SstI/SstI DNA fragment and an ~8 kb XhoI fragment which comprised the SstI/SstI fragment were both subcloned into pcDNAI. Further Southern blot analysis of the SstI/SstI DNA fragment revealed that an ~1000 bp BamHI/SstI fragment encoded a portion of the human PTH/PTHrP receptor which later proved to represent the exon encoding the putative signal peptide and the 5' non-translated region which is interrupted by an ~1000 bp intron (FIG. 7).

To isolate the remaining ~450 nucleotides of the coding region, poly (A)+ RNA from human kidney was reverse transcribed after priming with H12 (FIG. 7). After single strand synthesis, two independent PCRs were performed using two different forward primers: i) a degenerate primer RK-1 based on the 5' coding end of the two previously cloned PTH/PTHrP receptors, OK-O and R15B; and ii) primer RK-2 based on the 5' non-coding region of HPG1. H-26 was used as the reverse primer for both reactions. Southern blot and restriction map analyses confirmed the expected size of the amplified DNA encoding the human PTH/PTHrP receptor. The blunt-ended PCR products encoding the 5' end of the human PTH/PTHrP were cloned into pcDNAI using the dephosphorylated EcoRV sites. Sequence analysis of each PCR clone confirmed their 5' nucleotide difference due to the difference in forward primer sequence, but revealed otherwise identical sequences. Nucleotide sequencing of both strands of the human PTH/PTHrP receptor cDNA revealed an open reading frame encoding a 593-amino acid protein (FIG. 6, SEQ ID NO.:4).

Figure 19:
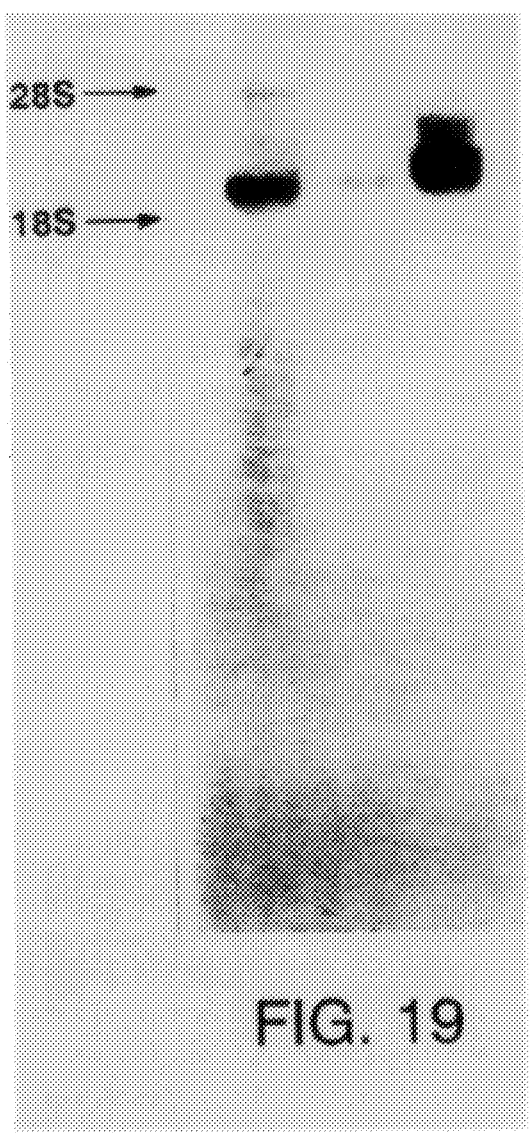
FIG. 19 represents a Northern blot analysis of total RNA (~10 μg/lane) prepared from human kidney (A) and SaOS-2 cells (B). The blot was hybridized with the full length cDNA encoding the human kidney PTH/PTHrP receptor; positions of 28S and 18S ribosomal RNA bands are indicated.
Figure 20:
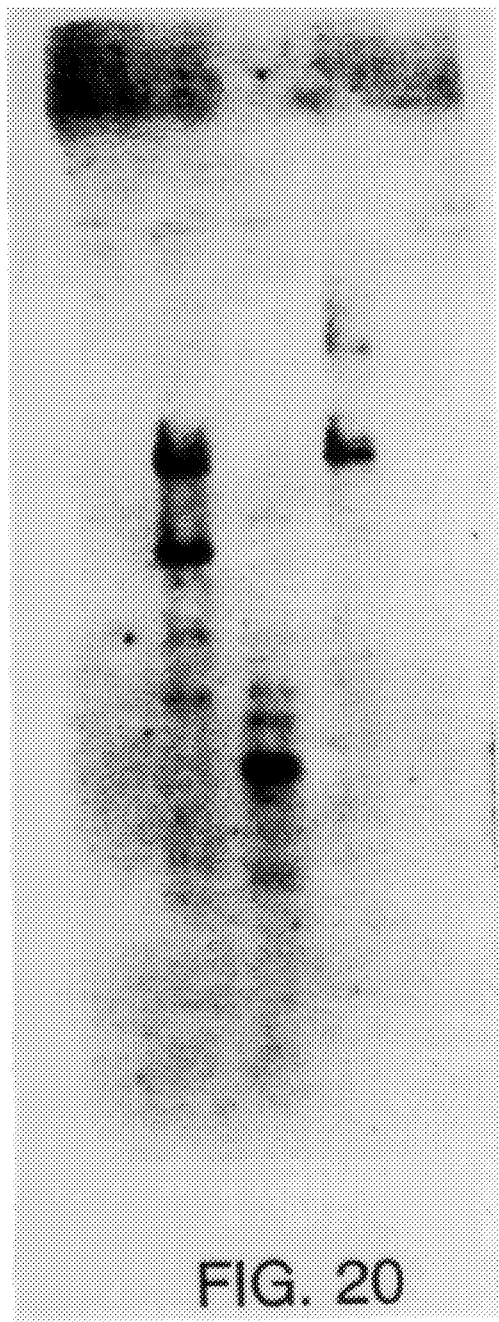
FIG. 20 represents a Southern blot analysis of human genomic DNA digested with SstI, HindIII, and XhoI (~10 μg/lane. The blot was hybridized with the full length cDNA encoding the human kidney PTH/PTHrP receptor.

The full-length human kidney PTH/PTHrP receptor cDNA, HKrk, was constructed using the BamHI/PvuII fragment of PCR clone #2 and HK-2. Using the full-length cDNA encoding the human PTH/PTHrP receptor, Northern blot analysis of total RNA (~10 μg/lane) from human kidney and SaOS-2 cells revealed one major hybridizing DNA species of ~2.5 kb (FIG. 19). The XhoI digest of normal human genomic DNA, when probed with the same full-length cDNA (FIG. 20), revealed one major hybridizing species of about 5.5 kb, and two DNA species of 4 and 8 kb which weakly hybridized. These date suggest that the human PTH/PTHrP receptor is the product of a single gene. This full-length clone was then transiently expressed in COS-7 cells for functional and biological characterization by the methods cited above.

Figure 8:
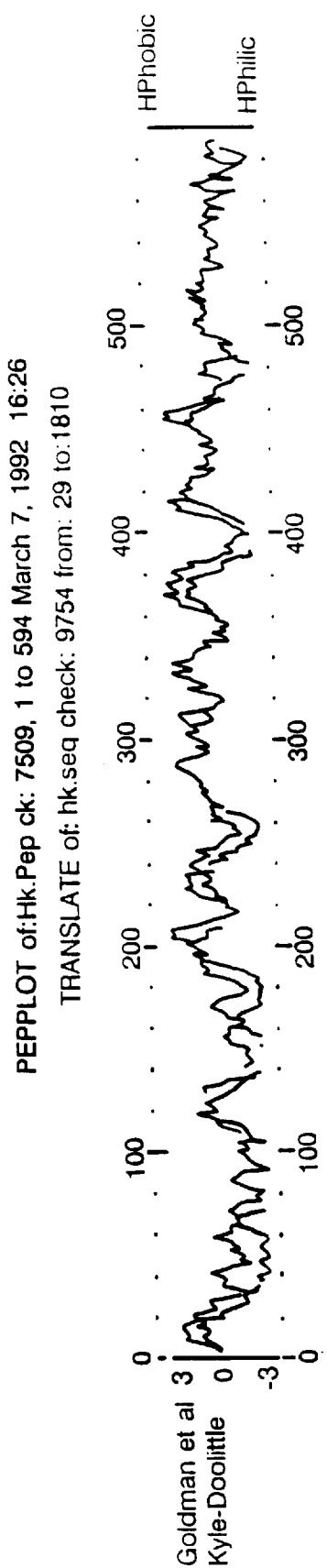
FIG. 8 is a hydrophobicity plot of the deduced amino acid sequence of the human kidney PTH/PTHrP receptor. Pre

Comparison of the human receptor with the opposum kidney PTH/PTHrP receptor and the rate bone PTH/PTHrP receptor, revealed 81% and 91% amino acid sequence identity, respectively, and consequently a very similar hydrophobicity plot (FIG. 8). All extracellular cysteines including the two cysteine residues in the presumed signal peptide are conserved, as are all potential, extracellular N-glycosylation sites. A number of the amino acids which were not identical between the human kidney and rat bone PTH/PTHr receptors were found to be conserved between the human and the opposum receptors. These conserved amino acids include an Arg to Leu at 51, an Arg to Trp at 58, an Arg to His at 262, an Asp to His at 358, an Ile to Thr at 422, and a Thr to Leu at 427.

Biological Characterization

Functional characterization of the biological properties of the opossum and rat PTH/PTHrP receptors was performed in transiently transfected COS cells by a radioreceptor assay technique using both $^{125}$I-PTHrP and $^{125}$I-NlePTH as radioligands, and by bioassays that measure ligand-stimulated cAMP accumulation, increase in intracellular free calcium, and stimulation of inositol phosphate metabolism, by the methods cited above.

Figure 9:
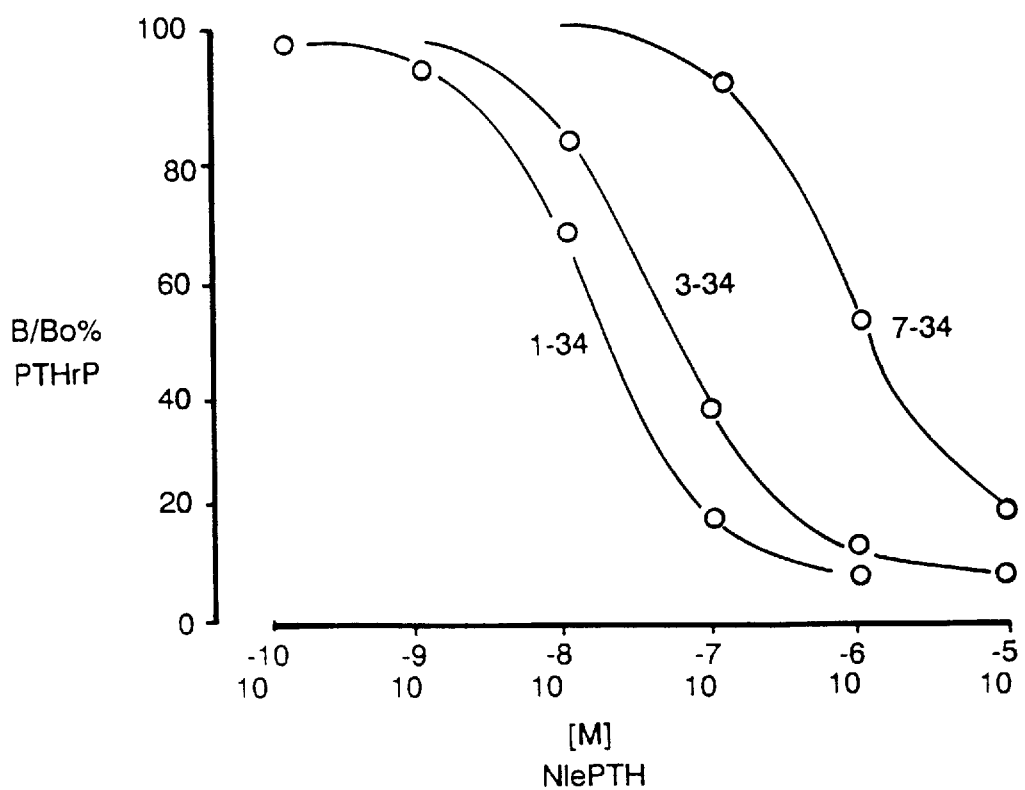
- FIG. 9 is a graph illustrating binding of PTHrP to COS cells transfected with OK-H.

FIG. 9 demonstrates that COS cells expressing OK-H bind $^{125}$I-PTHrP. These data also demonstrate that binding of PTHrP is inhibited when intact PTH (1–34) or PTH anlogues which are shortened at their amino terminus (i.e. the 3–34 and 7–34 analogues, which contain Nle substitutions for methionine at positions 8 and 18 and a tyrosine substitution for phenylalanine at position 34) are used as competitors for binding. Similarly, binding of $^{125}$I-NlePTH to, COS cells expressing OK-H was inhibited when PTHrP or PTHrP fragments were used as competitors. These data indicate that PTH and PTHrP both bind to the receptor encoded by OK-H.

Figure 10:
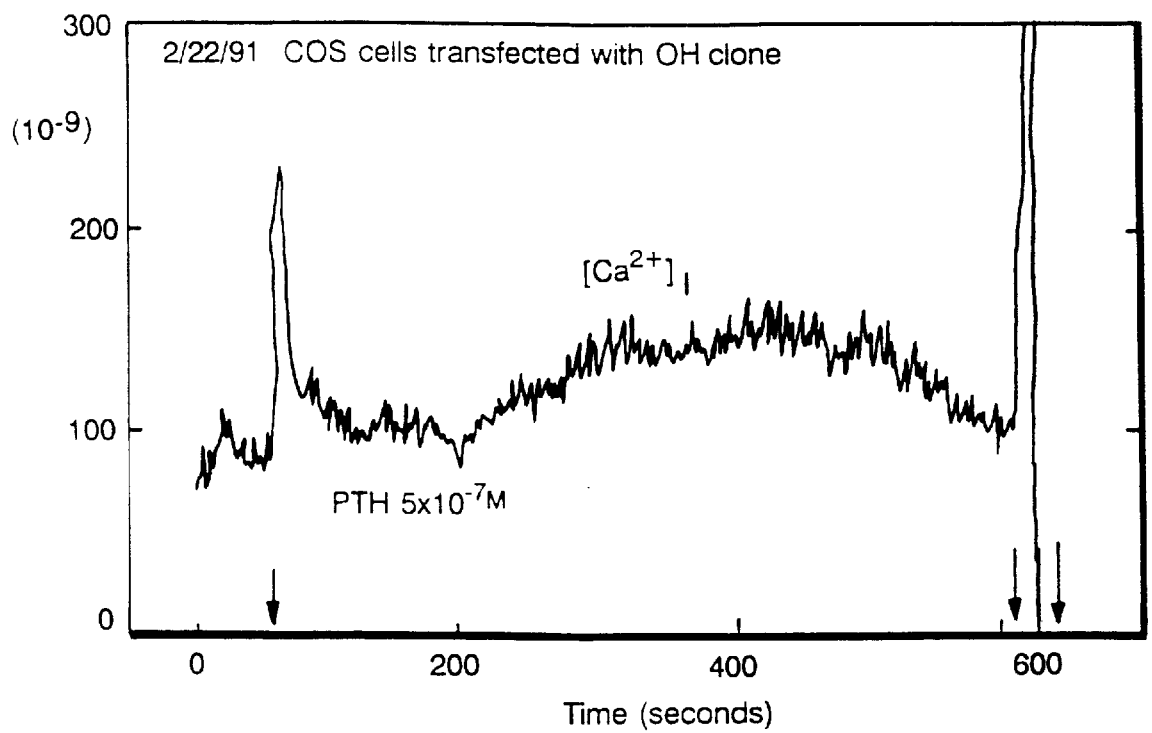
FIG. 10 is a graph illustrating stimulation of intracellular free calcium by NlePTH in COS cells transfected with OK-H.

FIG. 10 demonstrates that COS cells expressing OK-H increase their concentration of intracellular free calcium when exposed to NlePTH, but to a smaller extent (mean=39 nm), or not at all, when compared to COS cells expressing OK-O or R15B receptors (FIG. 12 and FIG. 14) and stimulated with NlePTH. Unlike COS cells expressing OK-O or R15B, COS cells expressing OK-H do not show a detectable increase in metabolism of inositol phosphate when stimulated with NlePTH (FIG. 15).

Figure 11:
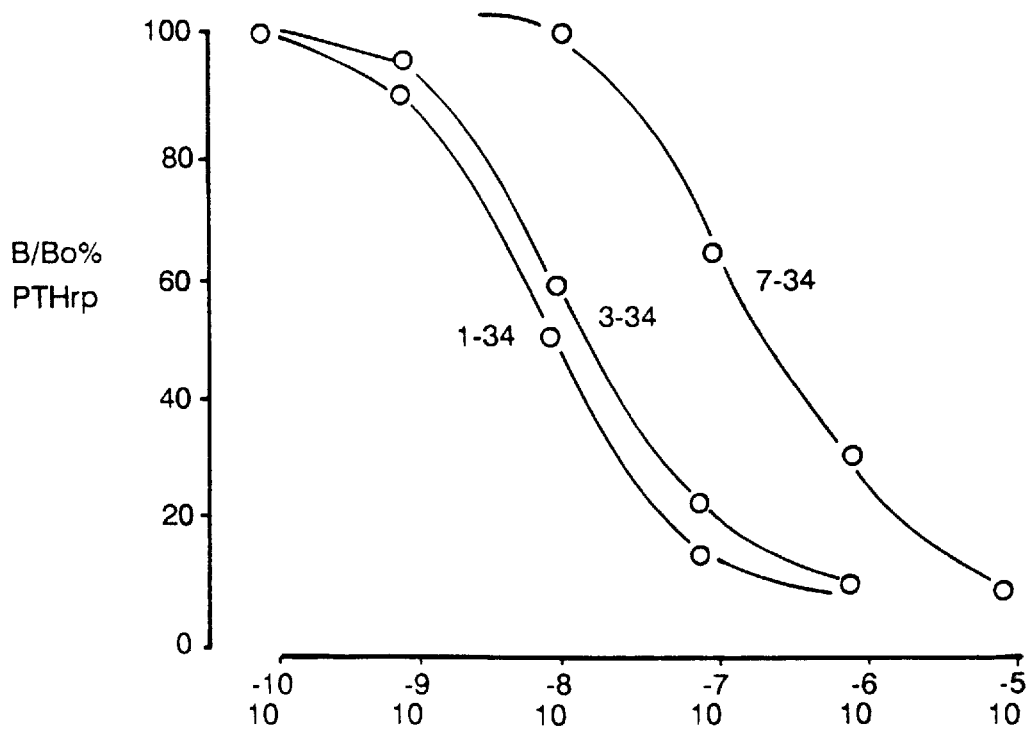
FIG. 11 is a graph illustrating binding of PTHrP to COS cells transfected with OK-O.

FIG. 11 demonstrates that COS cells expressing OK-O bind $^{125}$I-PTHrP. These data also demonstrate that binding of PTHrP is inhibited when intact PTH (1–34) or PTH analogues which are shortened at their amino terminus (i.e. the 3–34 and 7–34 analogues, which contain Nle substitutions for methionine at positions 8 and 18 and a tyrosine substitution for phenylalanine at position 34) are used as competitors for binding. Similarly, binding of $^{125}$I-NlePTH to COS cells expressing OK-H was inhibited when PTHrP or PTHrP fragments were used as competitors. These data indicate that PTH and PTHrP both bind to the receptor encoded by OK-O.

Figure 12:
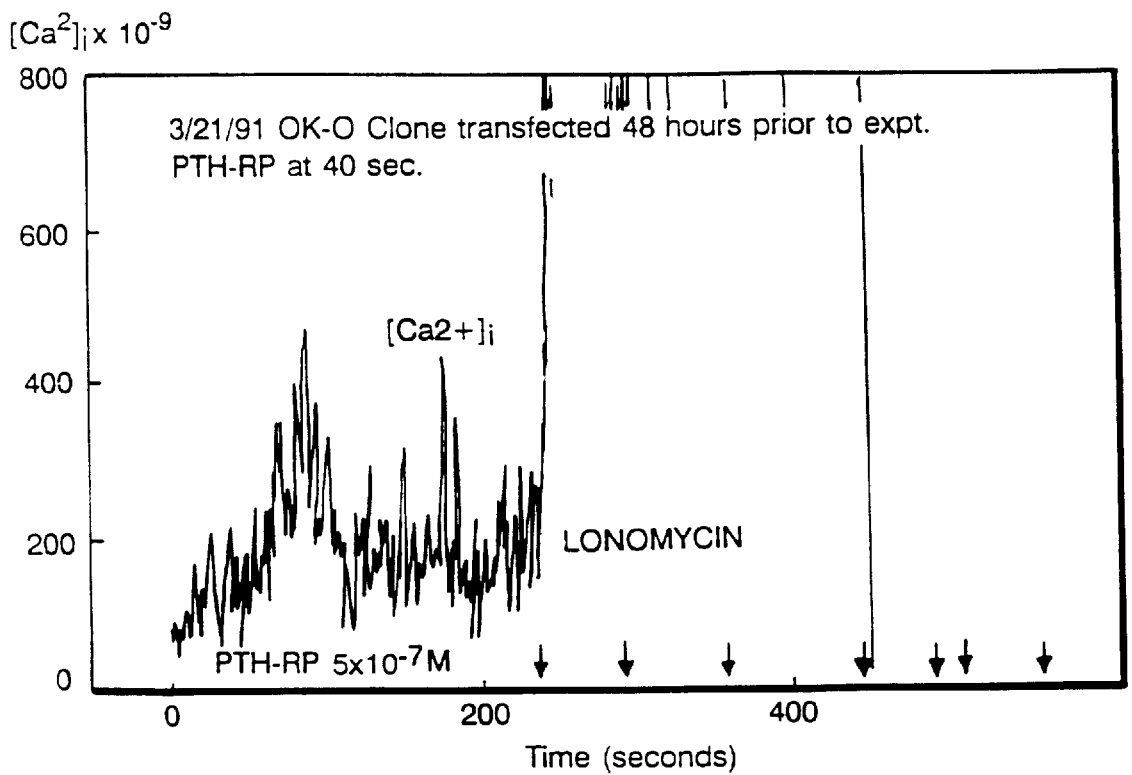
FIG. 12 is a graph illustrating stimulation of intracellular free calcium by NlePTH in COS cells transfected with OK-O.
Figure 15A:
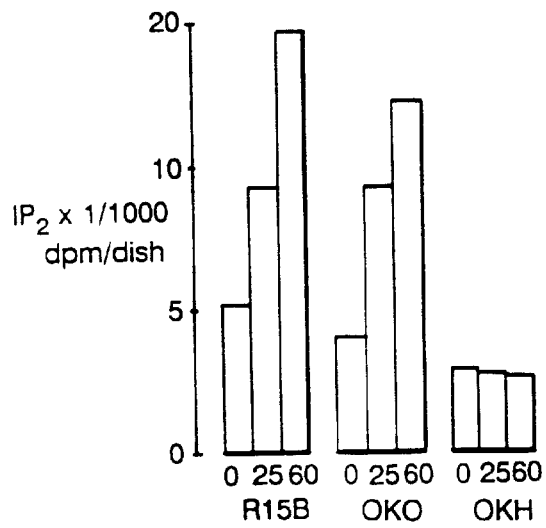
FIG. 15A is a graph illustrating accumulation of inositol bisphosphate ($IP_2$) after NlePTH stimulation of COS cells transfected with OK-H, OK-O, or R15B.
Figure 15B:
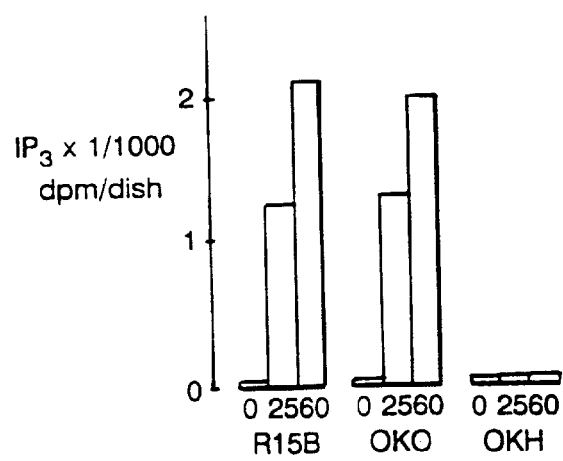
FIG. 15B is a graph illustrating accumulation of inositol triphosphate ($IP_3$) after NlePTH stimulation of COS cells transfected with OK-H, OK-O, or R15B.

FIG. 12 demonstrates that COS cells expressing OK-O increase their concentration of intracellular free calcium and their rate of inositol phosphate metabolism after stimulation with NlePTH and PTHrP (FIG. 15).

Figure 13:
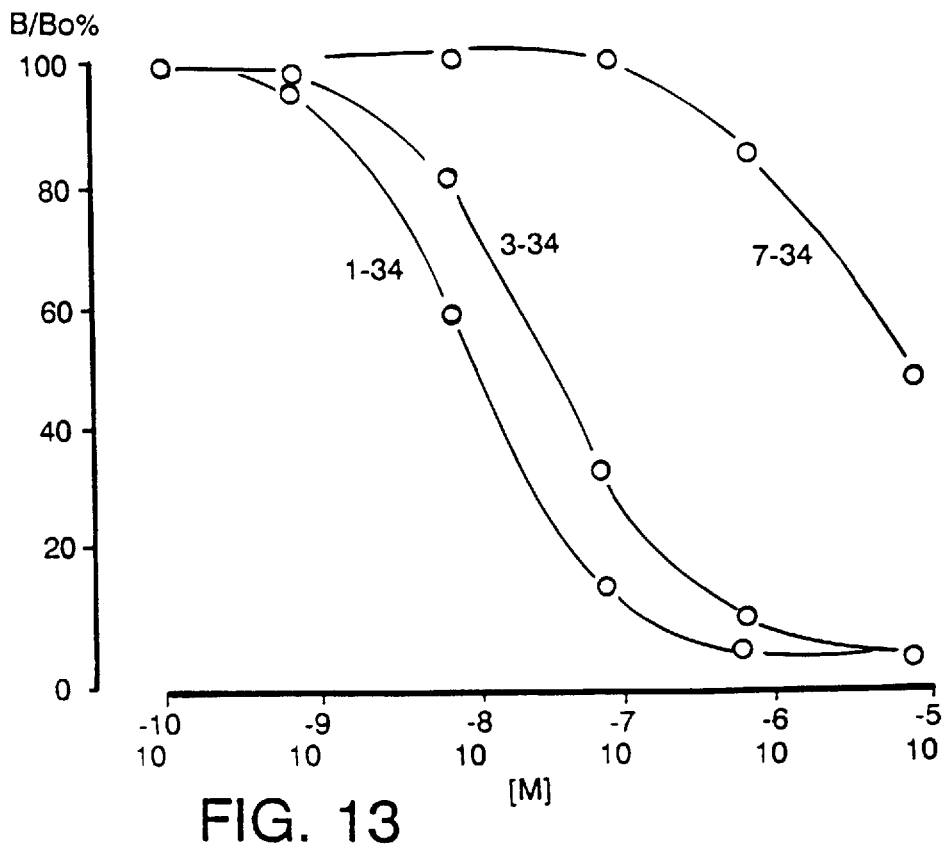
FIG. 13 is a graph illustrating binding of PTHrP to COS cells transfected with R15B.

FIG. 13 demonstrates that COS cells expressing R15B bind $^{125}$I-PTHrP. These data also demonstrate that binding of PTHrP is inhibited when intact PTH (1–34) or PTH anlogues which are shortened at their amino terminus (i.e. the 3–34 and 7–34 analogues, which contain Nle substitutions for methionine at positions 8 and 18 and a tyrosine substitution for phenylalanine at position 34) are used as competitors for binding. Similarly, binding of $^{125}$I-NlePTH to COS cells expressing OK-H was inhibited when PTHrP or PTHrP fragments were used as competitors. These data indicate that PTH and PTHrP both bind to the receptor encoded by R15B.

Figure 14:
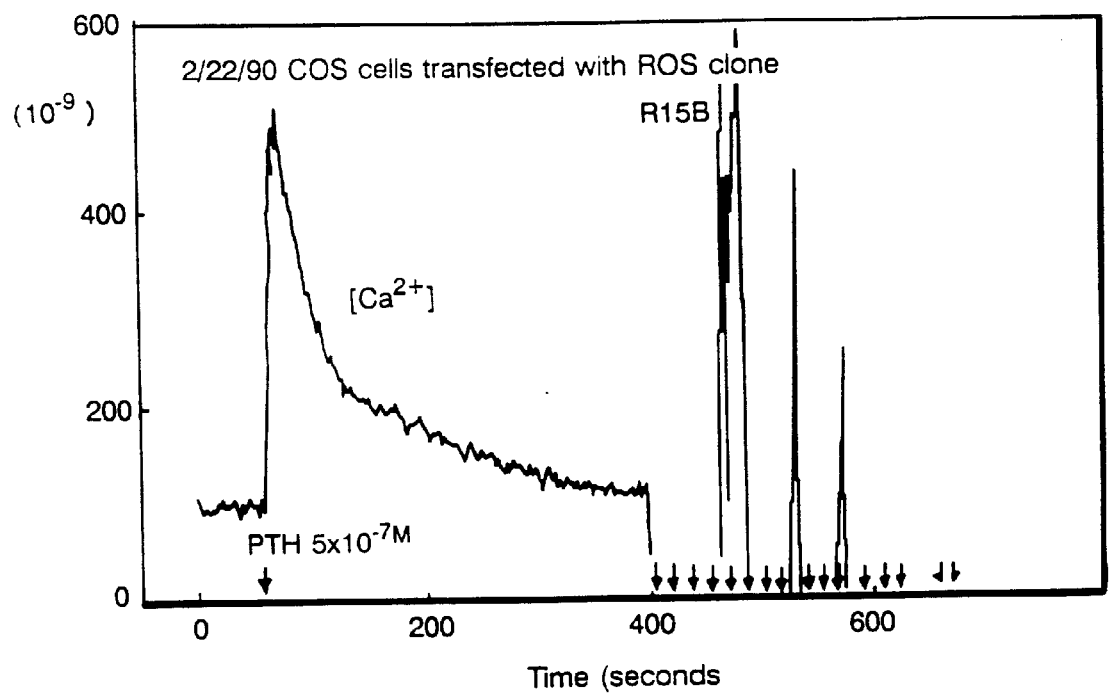
FIG. 14 is a graph illustrating stimulation of intracellular free calcium by NlePTH in COS cells transfected with R15B.

FIG. 14 demonstrates that cos cells expressing R15B increase their concentration of intracellular calcium to an extent similar to stimulated COS cells expressing OK-O.

FIG. 15 demonstrates that COS cells expressing R15B or OK-O increase their rate of phosphatidyl inositol hydrolysis, as evidenced by the rapid increase in inositol trisphosphate ($IP_3$) and inositol bisphosphate ($IP_2$) accumulation after stimulation of the cells with NlePTH or PTHrP. Conversely, COS cells expressing OK-H did not show any detectable increase in inositol trisphosphate and inositol bisphosphate accumulation after stimulation with NlePTH or PTHrP. These data suggest that the PTH receptor encoded by R15B and OK-O is coupled to phospholipase C, presumably through $G_p$. Since the only difference between OK-O and OK-H is in the cytoplasmic C-terminal tail, these data strongly suggest that the C-terminus of the PTH receptor encoded by OK-O and R15B is involved in the activation of phospholipase C.

Figure 16:
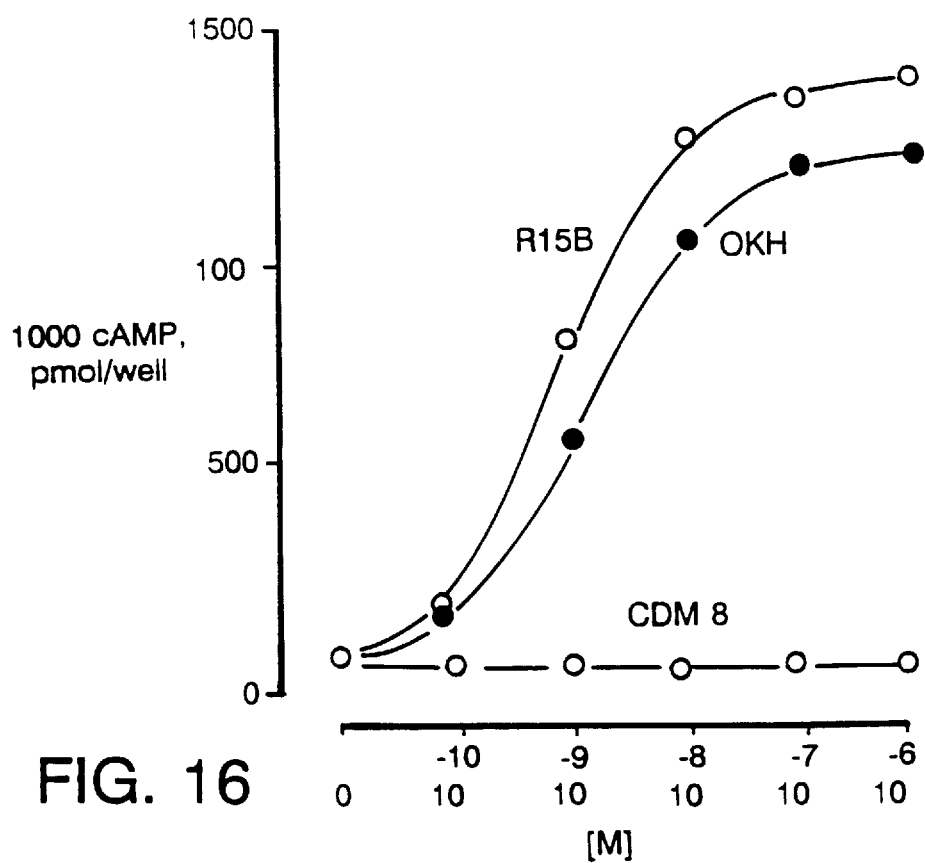
FIG. 16 is a graph illustrating cyclic AMP accumulation in COS cells transfected with CDM-8, OK-H, R15B by NlePTH.
Figure 17A:
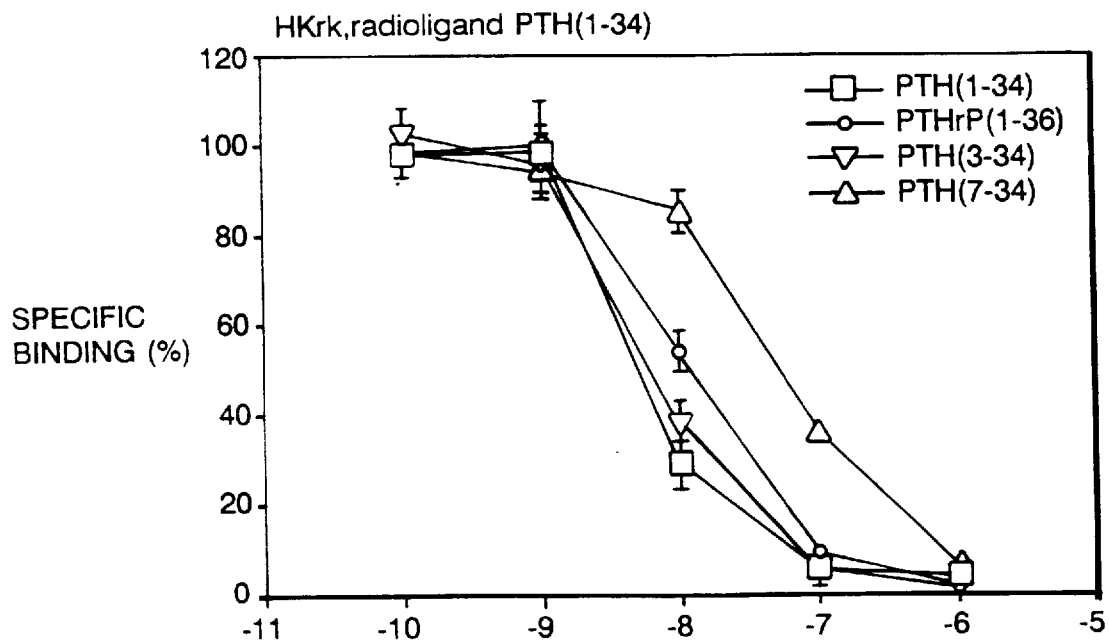
FIG. 17A is a graph illustrating binding of $^{125}$I-labelled PTH(1–34) to COS-7 cells transiently expressing the human kidney PTH/PTHrP receptor; competing ligands included PTH(1–34) (□), PTHrP(1–36) (*), PTH(3–34) (■), PTH(7–34) (+). Data are given as % specific binding and represent the mean±SD of at least three independent experiments.
Figure 17B:
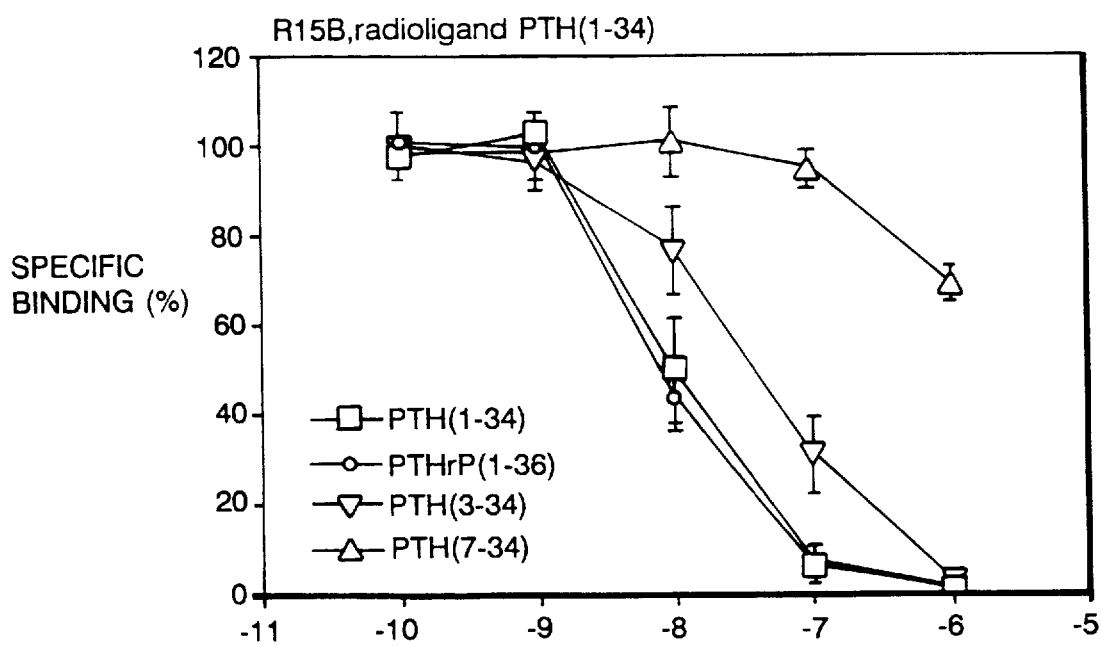
FIG 17B is graph illustrating binding of $^{125}$I-labelled PTH(1–34) to COS7 cells transiently expressing the rat bone PTH/PTHrP receptor, competing ligands included PTH(1–34) (□), PTHrP(1–36) (*), PTH(3–34) (■), PTH(7–34) (+). Data are given as % specific binding and represent the mean±SD of at least three independent experiments.
Figure 17C:
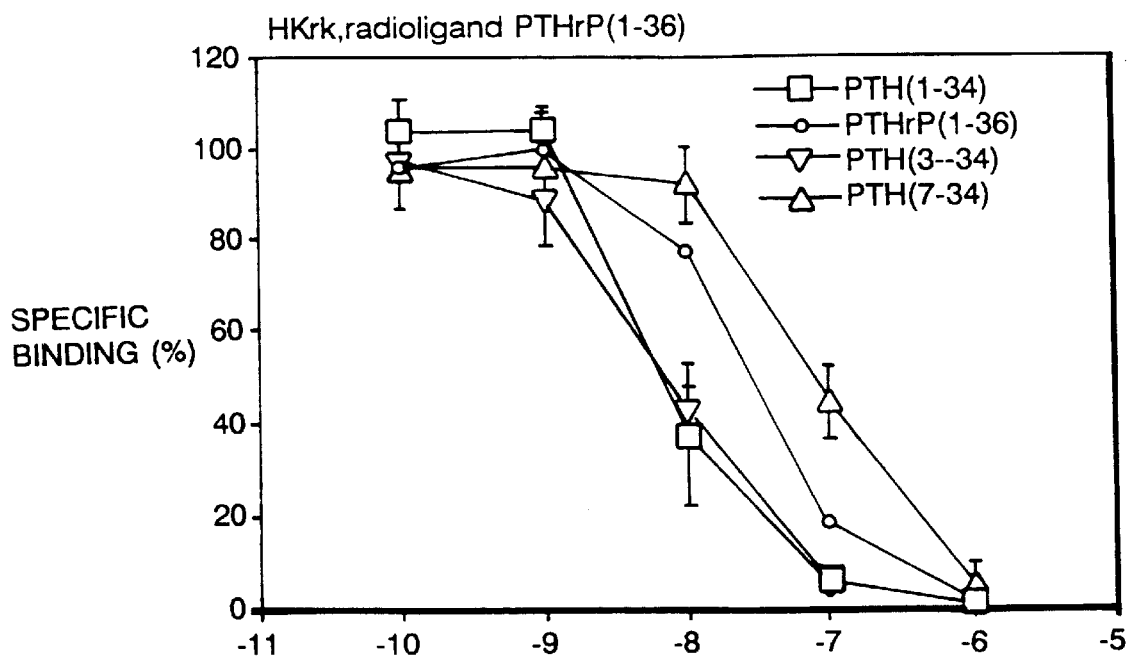
FIG. 17C is a graph illustrating binding of $^{125}$I-labelled PTHrP(1–36) to COS-7 cells transiently expressing with the human kidney PTH/PTHrP receptor; competing ligands included PTH(1–34) (□), PTHrP(1–36) (*), PTH(3–34) (■), PTH(7–34) (+). Data are given as % specific binding and represent the mean±SD of at least three independent experiments.
Figure 17D:
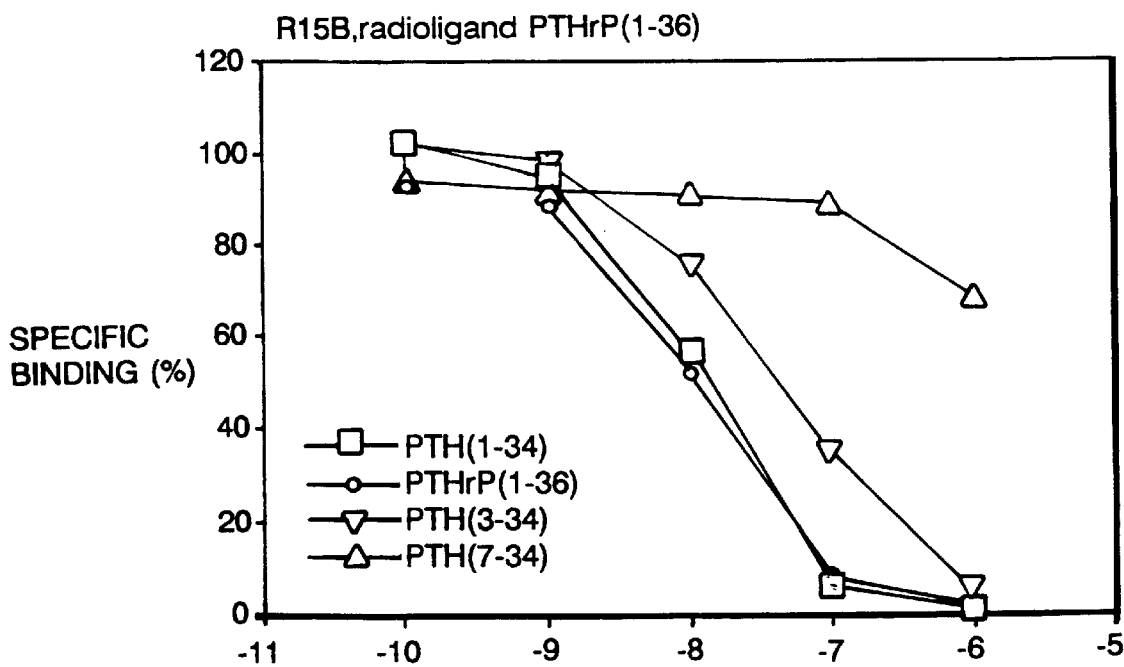
FIG. 17D is a graph illustrating binding of $^{125}$I-labelled PTHrP(1–36) to COS7 cells transiently expressing the rat bone PTH/PTHrP receptor competing ligands included PTH(1–34) (□), PTHrP(1–36) (*), PTH(3–34) (■), PTH(7–34) (+). Data are given as % specific binding and represent the mean±SD of at least three independent experiments.

FIG. 16 demonstrates that COS cells expressing R15B and OK-H increase cAMP accumulation after stimulation with NlePTH. Similar results were obtained in COS cells expressing OK-O. No CAMP stimulation was detected in COS cells transfected with the cDM8 vector alone. These data suggest that PTH receptor coupling to adenylate cyclase does not require the full length C-terminal cytoplasmic tail of the receptor.

These data demonstrate that all three PTH/PTHrP receptors cloned from both OK and ROS cell cDNA libraries bind the amino-terminal ligands of both peptides equivalently. Activation of all these receptors by ligand stimulates adenylate cyclase (as measured by increased intracellular cAMP), presumably through activation of one class of guanine nucleotide binding proteins (G-proteins). G-proteins have a trimeric peptide structure in which one of the subunits, alpha, is distinct, and the other two, beta and gamma, are identical or highly homologous. One of these G-proteins ($G_s$) contains G-alpha-"stimulatory" (G-alpha-s) which is involved in the activation of adenylate cyclase.

Binding of ligand to OK-O and R15B, but not to OK-H, also increases intracellular free calcium and stimulates metabolism of inositol phosphate. These properties strongly suggest that activation of both OK-O and R15B receptors by ligand results in stimulation of a second intracellular effector, phospholipase C. The coupling mechanism between these activated receptors and phospholipase C is likely to be a G-protein which is distinct from $G_s$. In contrast, the properties of the activated OK-H receptor which is truncated at the carboxy terminus, suggest that it may not activate phospholipase C, or that it activates phospholipase C inefficiently.

The biochemical role of the carboxy-terminal tail of the PTH/PTHrP receptor was further investigated by the construction of a carboxy-terminally-truncated rat receptor, R480, by standard PCR technology using R15B as a template and an upstream primer containing a stop codon inserted at position 481. Briefly, the upstream primer was a synthetic oligonucleotide based on nucleotides 1494–1513 of the rat cDNA sequence (see FIG. 3; SEQ ID NO.: 3) to which a stop codon and an XbaI cloning site were added. Thirty PCR cycles were carried out, each cycle consisting of 1 min at 92° C. for denaturation, 1 min at 60° C. for annealing, and 1 min at 72° C. for extension. The product was cut with NsiI and XbaI and purified by gel electrophoresis. R15B was sequentially digested with XbaI and NsiI, and the purified PCR product was then ligated into the XbaI-NsiI cut R15B vector. The resulting plasmid, R480, was amplified in bacteria and sequenced.

R480 encodes 480 amino acids that are identical to those in the 591 amino acids receptor. This truncated cDNA was expressed in COS-7 cells (transient expression) and in CHO cells (stable expression). Both COS-7 and CHO cells expressing the truncated receptor, R480, and the wild type receptor, RB, bind PTH(1–34) with equivalent affinities. When activated, R480 stimulates CAMP accumulation in COS7 and CHO cells as efficiently as does the wild type receptor. In contrast to the wild type receptor, R480 did not mediate any increase in $[Ca^{2+}]i$ when stimulated by PTH in either the COS-7 cells or the CHO cells. These data indicate that the molecular requirements for activation of phospholipase C and adenylate cyclase by PTH/PTHrP receptor are distinct from each other, and point to a major role of the carboxy-terminal tail of the PTH/PTHrP receptor in coupling to phospholipase C but not to adenylate cyclase. Of course, it is also possible that activated PTH/PTHrP receptors may activate additional G-proteins and/or intracelluar effector molecules.

Figure 18:
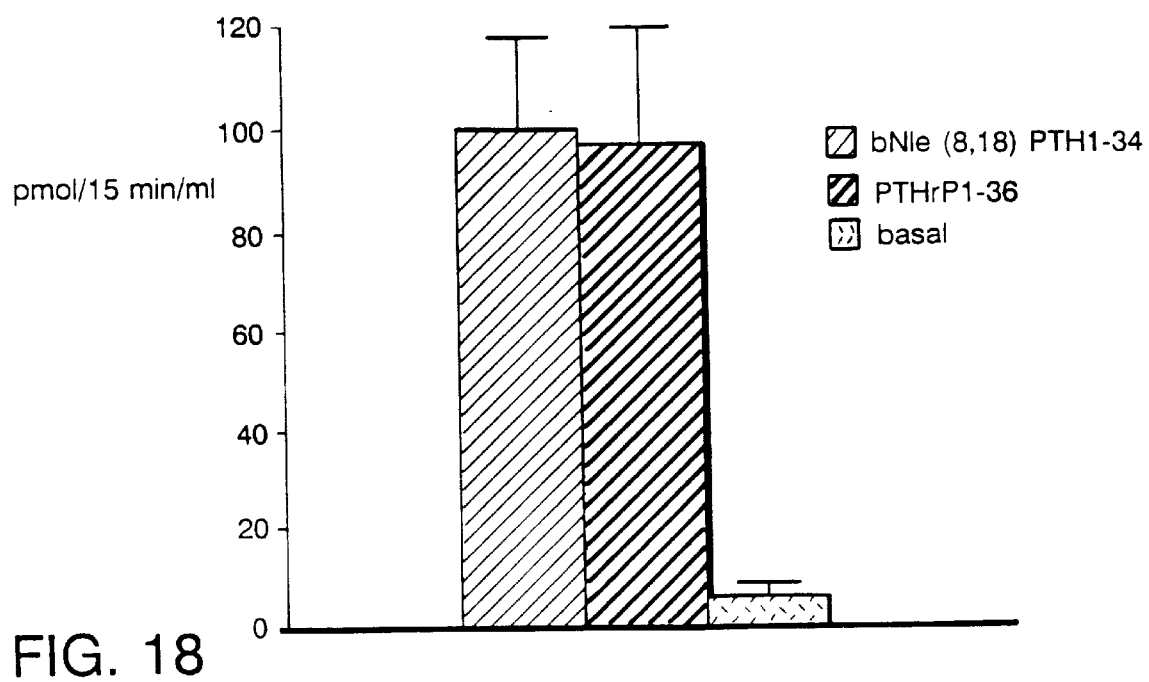
FIG. 18 is a bar graph illustrating stimulated accumulation of intracellular cAMP in COS-7 cells transiently expressing the human kidney receptor. Data show the mean±SD, and are representative of at least three independent experiments.

Analysis of COS-7 cells transfected with the cloned human PTH/PTHrP receptor demonstrated that radiolabelled PTH(1–34) and PTHrP(1–36) (~200,000 cpm) bound to the expressed receptors with similar efficiency (specific binding: 10.1±3.7% and 7.6±6.0%, respectively) to that observed for COS-7 cells expressing R15B (specific binding: 8.1+3.5% and 7.1±4.1%, respectively). The expressed human PTH/PTHrP receptors bound PTH(1–34) with 2-fold higher apparent $K_d$ than did the rat bone PTH/PTHrP receptor: ~5 nM versus ~10 nM (FIG. 17). However, despite their high degree of amino acid homology, the two receptors showed significant differences in affinity for PTH(3–34) and PTH(7–34). PTHrP(1–36) displayed a 2- to 4-fold lower affinity for the human PTH/PTHrP receptor than for the rat receptor (~35 nM for HKrk versus ~10 nM for R15B) which appeared more pronounced when PTHrP(1–36) was used as radioligand. The affinities for PTH(3–34) and PTH(7–34) were 7- and 35-fold higher with the expressed HKrK than with R15B (~7 nM versus ~45 nM for PTH(3–34), respectively; ~60 nM versus ~2000 nM for PTH(7–34), respectively). In COS-7 cells expressing either receptor, both PTH(1–34) and PTHrP(1–36) stimulated the increase in intracellular free calcium and cAMP accumulation to the same extent (FIG. 18).

Relationship of PTH/PTHrP receptors

The amino acid sequence of the human PTH/PTHrP receptor displays a very high degree of conservation compared to the bone PTH/PTHrP receptor from rat, a eutherian mammal, while its sequence identity with the PTH/PTHrP receptor with the opossum, a marsupial mammal, is less marked. Like the opossum kidney and the rat bone receptor, the human kidney receptor induces an increase in both intra-cellular cAMP and intracellular free calcium when challenged with either PTH or PTHrP. Despite the high degree of homology between the human PTH/PTHrP receptor and the opossum and rat homologs, the transiently expressed human receptor has some functional characteristics that are distinct from those of the rat bone receptor. These include a slightly higher affinity for PTH(1–34) and a significantly descreased affinity for PTHrP(1–36). Higher affinities were observed for PTH(3–34) and in particular for PTH(7–34), the affinity of which for the human receptor was about 35-fold higher in comparison to the rat bone receptor. These findings may have significant implications for the future development of PTH/PTHrP analogues, since they predict that species-specific tissues would be the appropriate tissues for testing the potency of antagonists (and agonists) in vitro.

Relationship of PTH/PTHrP receptors to other receptors

The biochemical properties of PTH and PTHrP receptors suggest that they are members of the class of membrane receptor molecules known as G-protein-linked membrane receptors. The structural features of well-characterized G-protein receptors indicate that they all have at least seven regions of several consecutive hydrophobic amino acids, each of which regions is of sufficient length to span the plasma membrane.

One subfamily of G-protein-linked membrane receptors, termed the glycopeptide receptor subfamily, includes receptors that bind and are activated by glycopeptide hormones (thyroid-stimulating hormone, luteinizing hormone, follicle-stimulating hormone, and chorionic gonadotropin). All of these receptors are characterized by (1) extensive putative amino-terminal extracellular domains (greater than 300 amino acids) that are thought to contain some or all of the ligand-binding domains, and (2) considerable amino-acid homology, particularly in the seven putative transmembrane domains. A second subfamily, termed the adrenergic/muscarinic subfamily, includes receptors that are activated by small ligands, such as the catecholoamines, neuromuscular transmitters, and retinol. These receptors are all characterized by relatively short (25–75 amino acids) putative amino-terminal extracellular domains, as well as considerable amino acid homology, particularly in the seven putative transmembrane domains. Activation of these receptors by their ligands appears to involve at least several of the multiple transmembrane domains, and does not appear to involve the amino-terminal portion of the receptors.

Several structural characteristics which can be deduced from the predicted amino acid sequence of the rat PTH/PTHrP receptor (FIG. 3) indicate that the PTH/PTHrP is a G-protein-linked receptor. The amino terminus shows characteristic features of a signal peptide, including a hydrophobic domain and the presence of three consecutive leucine residues. This amino acid stretch of 20–28 amino acids may serve as a leader sequence, similar to the amino terminus preceding the extracellular domains of other glycoprotein receptors. There is also a cluster of seven hydrophobic segments which represent putative membrane-spanning domains (FIG. 19).

The predicted amino acid sequences of the opossum kidney, rat bone and human kidney PTH/PTHrp receptors indicate that they do not fit comfortably into either of these G-protein linked receptor subfamilies. Overall homology of the rat and human PTH/PTHrP receptors with the glycopeptide receptor and adrenergic/muscarinic subfamilies is approximately 10 to 20%, with a somewhat higher degree of homology within the transmembrane domains. The latter is to be expected because of the limited menu of hydrophobic amino acids that could occur in those regions. Twenty percent homology is far less than that found among the receptors generally accepted to be members of each of these subfamilies. Additionally, there are no portions of these sequences that have what could be characterized as intense homology (i.e., exactly matching amino acid sequences), even over limited regions.

Recent comparison with the newly characterized secretin and calcitonin ancestors (Ishihara et al., EMBO J 10:1635, 1991; Lin et al. Science 254:1022, 1991) has revealed between 30 and 40% identity between these receptors and the PTH/PTHrP receptor. Although the PTH/PTHrP receptor is more than 100 amino acids longer than the calcitonin receptor, there is an ~32% identify between the amino acid sequences of the opossum kidney PTH/PTHrP receptor (SEQ ID NO NO.:2) and porcine kidney calcitanin receptor (GenBank accession no. M74420). A stretch of 17 out of 18 amino acids in the putative transmembrane domain VII are identical. Also, two out of four N-linked glycoslyation sites and the position of seven out of eight potentially extracellular cysteines are conserved. Major differences between the two receptors appear to lie in their $NH_2$-terminal and COOH-terminal domains. Comparison of amino acid sequences of the rat secretin receptor (GenBank accession no. X59132) and the human PTH/PTHrP receptor indicates that there is a 43% identity between these two receptors, with a stretch of 21 out of 25 amino acids of the putative transmembrane domain VII being identical. The similarity between the PTH/PTHrP, calcitonin and secretin receptors suggests that they represent a new family of seven transmembrane-spanning G protein-coupled receptors that activate adenylate cyclase. Given the amino acid sequences of these receptors, those skilled in art would be able to compare these sequences for regions of identity which would be useful in the design of nucleic acid probes which could then be used for the identification and isolation of other receptors which would belong to this family.

Deposit of Clones

Under the terms of the Budapest Treaty on the International Recognition of the Deposit of Microorganisms for the Purpose of Patent Procedure, the cDNA expression plasmids R15B, OK-O, and OK-H; the phage HPG1; and a plasmid (termed 8A6) containing part of the human clone have been deposited with the American Type Culture Collection (ATCC), where they bear the respective accession numbers ATCC No. 68571, 68572, 68573, 40998 and 68570. Applicants' assignee, The General Hospital Corporation, represents that the ATCC is a depository affording permanence of the deposits and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. 122. The deposited material will be maintained with all the care necessary to keep it viable and uncontaminated for a period of at least five years after the most recent request for the furnishing of a sample of the deposited plasmid, and in any case, for a period of at least thirty (30) years after the date of deposit or for the enforceable life of the patent, whichever period is longer. Applicants' assignee acknowledges its responsibility to replace the deposits should the depository be unable to furnish a sample when requested due to the condition of the deposit.

POLYPEPTIDES

Polypeptides according to the invention include the opossum and rat and human parathyroid hormone receptors as shown in FIGS. 1–3 and 6, respectively, and any other naturally-occurring receptor which can be produced by methods analogous to those used to clone and express these receptors, or by methods utilizing as a probe all or part of one of the sequences described herein. In addition, any analog or fragment of a PTH receptor capable of binding to a parathyroid hormone or a parathyroid hormone-related protein is within the invention.

Specific receptor analogs of interest include full-length or partial receptor proteins having an amino acid sequence which differs only by conservative amino acid substitutions: for example, substitution of one amino acid for another of the same class (e.g., valine for glycine; arginine for lysine, etc.), or by one or more non-conservative amino-acid substitutions, deletions, or insertions located at positions which do not destroy the receptor's ability to bind to parathyroid hormone or parathyroid hormone-related protein.

Figure 21:
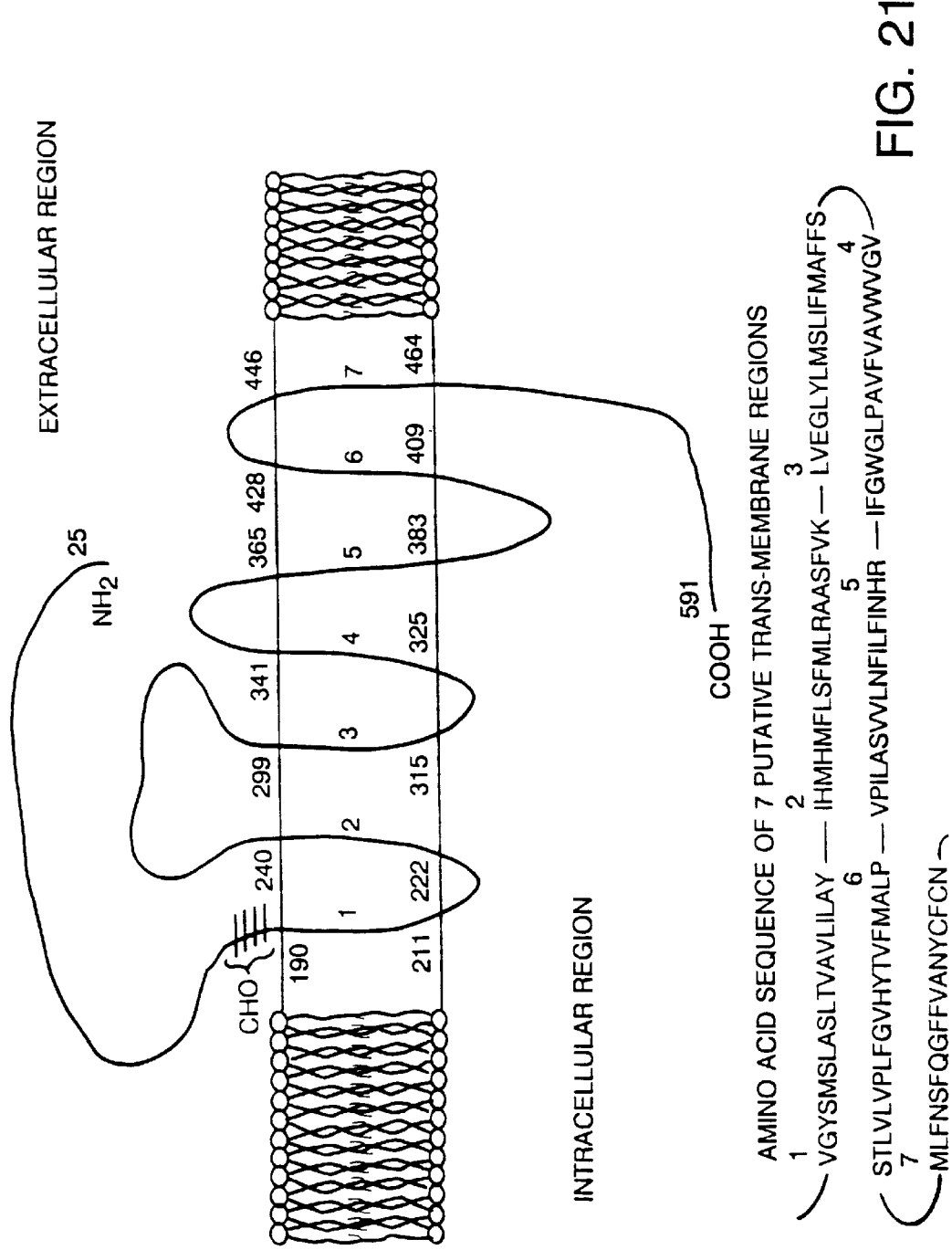
FIG. 21 is a schematic diagram of the proposed arrangement, in a cellular membrane, of PTH/PTHrP rat bone receptor encoded by R15B.

Specific receptor fragments of particular interest include, but are not limited to, portions of the receptor deduced to be extracellular from the primary amino acid sequence, using a hydrophobicity/hydrophilicity calculation such as the Chou-Fasman method (see, e.g., Chou and Fasman, Ann. Rev. Biochem. 47:251, 1978). Hydrophilic domains, particularly ones surrounded by hydrophobic stretches (e.g., transmembrane domains) of at least 10 amino acids, present themselves as strong candidates for extracellular domains. FIG. 21 illustrates a predicted arrangement of extracellular, intracellular, and transmembrane domains of one PTH receptor.

Examples of specific PTH receptor fragments include those with the following amino acid sequences (shown as standard single-letter symbols), derived from the deduced amino acid sequence of the R15B clone: Extracellular domains:

RP-1: Thr Asn Glu Thr Arg Glu Val Phe Asp Arg Leu Gly Met Ile Tyr Thr Val Gly (SEQ ID NO.: 5)

RP-2: Tyr Leu Tyr Ser Gly Phe Thr Leu Asp Glu Ala Glu Arg Leu Thr Glu Glu Glu Leu (SEQ ID NO.: 6)

RP-3: Val Thr Phe Phe Leu Tyr Phe Leu Ala Thr Asn Tyr Tyr Trp Ile Leu Val Glu Gly (SEQ ID NO.: 7)

RP-4: Tyr Xaa Arg Ala Thr Leu Ala Asn Thr Gly Cys Trp Asp Leu Ser Ser Gly His Lys Lys Trp Ile Ile Gln Val Pro (SEQ. ID NO.: 8)

RP-5: Pro Tyr Thr Glu Tyr Ser Gly Thr Leu Trp Gln Ile Gln Met His Tyr Glu Met (SEQ ID NO.: 9)

RP-6: Asp Asp Val Phe Thr Lys Glu Glu Gln Ile Phe Leu Leu His Arg Ala Gln Ala (SEQ ID NO.: 10)

Intracellular domains:

RP-7: Phe Phe Arg Leu His Cys Thr Arg Asn Tyr (SEQ ID NO.: 11)

RP-8: Glu Lys Lys Tyr Leu Trp Gly Phe Thr Leu (SEQ ID NO.: 12)

RP-9: Val Leu Ala Thr Lys Leu Arg Glu Thr Asn Ala Gly Arg Cys Asp Thr Arg Gln Gln Tyr Arg Lys Leu Leu Lys (SEQ ID NO.: 13) These fragments were synthesized and purified by HPLC according to the method of Keutmann et al., (Endocrinology 117: 1230, 1984).

EXPRESSION OF POLYPEPTIDES

Polypeptides according to the invention may be produced by expression from a recombinant nucleic acid having a sequence encoding part or all of a cell receptor of the invention, using any appropriate expression system: e.g., transformation of a suitable host cell (either prokaryotic or eukaryotic) with the recombinant nucleic acid in a suitable expression vehicle (e.g., pcDNAI). The precise host cell used is not critical to the invention; however, in the case wherein the polypeptides of the invention include all or part of the PTH/PTHrP receptor, the following host cells are preferred: COS cells, LLC-PK1 cells, OK cells, AtT20 cells, and CHO cells. The method of transfection and the choice of expression vehicle will depend on the host system selected. Mammalian cell transfection methods are described, e.g., in Ausubel et al. (Current Protocols in Molecular Biology, John Wiley & Sons, New York, 1989); expression vehicles may be chosen from those discussed, e.g., in Cloning Vectors: A Laboratory Manual (P. H. Pouwels et al., 1985, Supp. 1987). Stably transfected cells are produced via integration of receptor DNA into the host cell chromosomes. Suitable DNAs are inserted into pcDNA, pcDNAI-Neo, or another suitable plasmid, and then cells are transfected with this plasmid with or without cotransfection with psV-2-Neo, or psV-2-DHFR by standard electroporation, calcium phosphate, and/or DEAE/Dextran techniques. Selection of transfected cells is performed using progressively increasing levels of G418 (Geneticin, GIBCO), and if necessary, methotrexate.

DNA sequences encoding the polypeptides of the invention can also be expressed in a prokaryotic host cell. DNA encoding a cell receptor or receptor fragment is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification. Prokaryotes most frequently used are various strains of *E. coli*; however, other microbial strains may also be used. Plasmid vectors are used which contain replication origins, selectable markers, and control sequences derived from a species compatible with the microbial host. For example, *E. coli* may be transformed using derivatives of pBR322, a plasmid constructed by Bolivar et al. (Gene 2: 95, 1977) using fragments derived from three naturally-occurring plasmids, two isolated from species of Salmonella, and one isolated from *E. coli*. pBR322 contains genes from ampicillin and tetracycline resistance, and thus provides multiple selectable markers which can be either retained or destroyed in constructing the desired expression vector. Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., Nature 198: 1056, 1977) and the tryptophan (Trp) promoter systems (Goeddel et al., Nucl. Acids Res. 8: 4057, 1980) as well as the lambda-derived $P_L$ promoter and N-gene ribosome binding site (Simatake et al., Nature 292:128, 1981).

The nature of the cell receptor proteins of the invention is such that, upon expression within a cell, it is moved to the cellular membrane and partially through the membrane, so that part of it remains embedded in the membrane, part extends outside the cell, and part remains within the cell. Transformed cells bearing such embedded cell receptors may themselves be employed in the methods of the invention, or the receptor protein may be extracted from the membranes and purified.

Expression of peptide fragments lacking the hydrophobic portions of the protein responsible for anchoring the intact protein in the cellular membrane would not be expected to become embedded in the membrane; whether they remain within the cell or are secreted into the extracellular medium depends upon whether or not a mechanism promoting secretion (e.g., a signal peptide) is included. If secreted, the polypeptides of the invention can be harvested from the medium; if not, the cells must be broken open and the desired polypeptide isolated from the entire contents of the cells. Specific examples of polypeptides which might be expressed include, without limitation:

1) Amino-terminal portion comprising amino acids 1–192, including the putative leader sequence, of the rat bone PTH/PTHrP receptor as shown in FIG. 3.

2) Amino-terminal portion comprising amino acids 27–192, excluding the putative leader sequence, of the rat bone PTH/PTHrP receptor as shown in FIG. 3.

3) The full-length PTH/PTHrP receptor from rat bone, as shown in FIG. 3.
4) RP-1 (as described above).
5) RP-2 (as described above).

The polypeptide of the invention can be readily purified using affinity chromatography. Antibodies to these polypeptides, or the receptor specific ligands, (e.g., the hormones PTH and PTHrP for the PTH/PTHrP receptor) may be covalently coupled to a solid phase support such as Sepharose 4 CNBr-activated sepharose (Pharmacia), and used to separate the polypeptide of the invention from any contaminating substances. Typically 1 mg of ligand or antibody will be incubated with CNBr-activated sepharose at 4° C. for 17–20 h (with shaking). The sepharose is rinsed with 1M Tris HCL (pH8) to block excess active sites. The sepharose-PTH, sepharose-PTHrP, or sepharose-antibody is then incubated with the crude polypeptide in phosphate-buffered saline (pH 7.4) at 4° C. for 2 h (with shaking). The sepharose is then typically packed in a column, thoroughly washed with PBS (typically 10 times the column volume), and eluted with dilute HCl in $H_2O$ (pH 1.85). The eluate may then be concentrated by lyophylization and its purity checked, for example, by reverse phase HPLC.

ANTI-CELL RECEPTOR ANTIBODIES

Cell receptor or receptor fragments of the invention may be used to generate antibodies by any conventional method well known to those skilled in the art, including those which generate polyclonal antibodies and those which generate monoclonal antibodies. For example, the deduced amino acid sequence of the PTH receptor reveals a protein structure that appears to have several transmembrane (i.e., hydrophobic) domains interspersed with presumably extracellular and intracellular regions (see FIG. 21) analogous to those found in other G protein-linked receptors. This information can be used to guide the selection of regions of the receptor protein which would be likely to be exposed on the cell surface, and thus would be presented to antibodies in vivo. A short peptide representing one or more of such regions may be synthesized (e.g., chemically or by recombinant DNA techniques) and used to immunize an animal (e.g., a rabbit or a mouse) to generate polyclonal or monoclonal antibodies. For example, certain of the peptides of the PTH/PTHrP receptor listed above (RP-1, RP-5 and RP-6) have been chemically synthesized using standard techniques and used to generate polyclonal antibodies in rabbits by the following procedure:

A preparation of a given peptide emulsified with complete Freund's Adjuvant is injected intradermally into rabbits. Booster injections are emulsified in or complete adjuvant and injected at monthly intervals.

Antibody titer is assessed using either of two methods. First, serial dilutions of the antiserum in 1% normal rabbit serum are incubated with $^{125}$I-labelled PTH/PTHrP receptor fragment by standard methods (e.g., see Segre et al., supra) for 24 h at 4° C. The bound $^{125}$I-PTH/PTHrP receptor fragments are separated from unbound by addition of 100 μl of second antibody (anti-rabbit IgG, Sigma) diluted 1:20 and 1 ml of 5% polyethylene glycol, followed by centrifugation at 2000 rpm for 30 min. at 4° C. The supernatant is removed and the pellet analyzed for radioactivity in a γ-counter. In the second method, cell lines expressing either native (e.g., ROS 17/2.8, OK, SaOS-02 cells) or recombinant (COS cells or CHO cells transfected with R15B, OK-O or OK-H) PTH/PTHrP receptors are incubated with serially diluted antibody at 4° C., 20° C. or 37° C. for 1–4 h. The cells are rinsed with PBS (×3) and incubated for 2 h at 4° C. with $^{125}$I-labelled (NEN, Dupont) or FITC-labelled (Sigma) second antibodies. After rinsing (×3 with PBS), the cells were either lysed with 0.1M NaOH and counted in γ-counter (if $^{125}$I-labelled second antibody was used) or fixed with 1% paraformaldehyde and examined by fluorescent microscopy (if FITC-labelled second antibody was used).

Another method for producing antibodies utilizes as antigen the intact cell receptor protein of the invention expressed on the surface of cells (e.g., mammalian cells, such as COS cells, transfected with DNA encoding the receptor). Such cells are prepared by standard techniques, e.g., by the DEAE-dextran transfection method, using a vector encoding and capable of directing high-level expression of the cell receptor. Such cells may be used to generate polyclonal or monoclonal antibodies. For example, monoclonal antibodies specific for the PTH/PTHrP receptor may be produced by the following procedure:

Intact COS cells expressing high levels of rat recombinant PTH receptors on the cell surface are injected intraperitoneally (IP) into Balb-c mice (Charles River Laboratories, Willmington, Mass.). The mice are boosted every 4 weeks by IP injection, and are hyper-immunized by an intravenous (IV) booster 3 days before fusion. Spleen cells from the mice are isolated and are fused by standard methods to myeloma cells. Hybridomas are selected in standard hypoxanthine/aminopterin/thymine (HAT) medium, according to standard methods. Hybridomas secreting antibodies which recognize the PTH receptor are initially identified by screening with cell lines which naturally express abundant copies of the PTH-receptor per cell (such as ROS17/2.8 or OK cells), using standard immunological techniques. Those hybridomas which produce antibodies capable of binding to the PTH receptor are cultured and subcloned. Secondary screening with radioreceptor and cAMP stimulation assays can then be performed to further characterize the monoclonal antibodies (see below).

SCREENING FOR PTH RECEPTOR ANTAGONISTS AND AGONISTS

The polypeptides and antibodies of the invention and other compounds may be screened for PTH-competition and for antagonistic or agonistic properties using the assays described herein.

In one example, those antibodies that recognize the PTH receptor on the intact cells are screened for their ability to compete with PTH or PTHrP for binding to a PTH/PTHrP receptor. Cells expressing PTH receptor on the cell surface are incubated with the $^{125}$I-PTH analog, $^{125}$I-NlePTH or $^{125}$I-PTHrP in the presence or absence of the polyclonal or monoclonal antibody to be tested, for 4 h at 15° C. The antibody used may be from crude antiserum, cell medium, or ascites, or in purified form. After incubation, the cells are rinsed with binding buffer (e.g., physiological saline), lysed, and quantitatively analyzed for radioactivity using a gamma-counter. Antibodies that reduce binding of the PTH analog to the PTH receptor are classified as competitive; those which do not are noncompetitive.

Compounds, including antibodies and polypeptides, may be screened for their agonistic or antagonistic properties using the cAMP accumulation, intracellular calcium, and/or inositol phosphate assays described above. Cells expressing PTH receptor on the cell surface are incubated with PTH, PTH-receptor antibody, or a combination of both, for 5–60 minutes at 37° C., in the presence of 2 mM IBMX (3-isobutyl-1-methyl-xanthine, Sigma, St. Louis, Mo.). Cyclic AMP accumulation is measured by specific radio-immunoassay, as described above. A compound that competes with PTH for binding to the PTH receptor, and that inhibits the effect of PTH on cAMP accumulation, is considered a competitive PTH antagonist. Conversely, a compound that does not compete for PTH binding to the PTH receptor, but which still prevents PTH activation of cAMP accumulation (presumably by blocking the receptor activation site) is considered a non-competitive antagonist. A compound that competes with PTH for binding to the PTH receptor, and which stimulates cAMP accumulation in the presence or absence of PTH, is a competitive agonist. A compound that does not compete with PTH for binding to the PTH receptor but which is still capable of stimulating cAMP accumulation in the presence or absence of PTH, or which stimulates a higher accumulation than that observed by PTH alone, would be considered a non-competitive agonist.

USE

The polypeptides, antibodies, and other compounds of the invention are useful for the diagnosis, classification, prognosis, and/or treatment of disorders which may be characterized as related to the interaction between a cell receptor of the invention and its specific ligand. For example, some forms of hypercalcemia and hypocalcemia are related to the interaction between PTH and PTHrP and the PTH/PTHrP receptor(s). Hypercalcemia is an condition in which there is an abnormal elevation in serum calcium level; it is often associated with other diseases, including hyperparathyroidism, osteoporosis, carcinomas of the breast, lung and prostrate, epidermoid cancers of the head and neck of the esophagus, multiple myeloma, and hypernephroma. Hypocalcemia, a condition in which the serum calcium level is abnormally low, may result from a deficiency of effective PTH, e.g., following thyroid surgery.

In a first example, the compounds of the invention are used to manufacture diagnostic agents which are used as diagnostic tools to diagnose hypercalcemia and to distinguish between-hypercalcemic conditions, i.e., to differentiate hypercalcemia mediated by PTH or PTHrP (e.g., hyperparathyroidism and humoral hypercalcemia of malignancy), from hypercalcemia associated with diseases which do not involve these factors (e.g., local osteolytic hypercalcemia mediated by the presence of metastatic tumor cells in direct contact with bone, and certain rare types of malignancy-related hypercalcemias mediated by an increase of humoral factors, such as osteoclast activating factor (interleukin), lymphotoxin, calcitriol, type E prostaglandins, and vitamin D-like sterols).

In one method of diagnosis, serum total and/or ionized calcium levels are measured by standard techniques before and after the administration of the PTH or PTHrP antagonists of the invention. PTH or PTHrP related hypercalcemias would be detectable as a decrease in serum calcium levels following administration of the antagonist of the invention. In contrast, for hypercalcemic conditions mediated by factors other than PTH or PTHrP, the serum calcium levels would remain unchanged even after administration of the antagonist.

Another diagnostic application of the invention permits measurement of the level of PTH or PTHrP in a biological sample in order to diagnose PTH or PTHrP related tumors, e.g., tumors which are associated with humoral hypercalcemia of malignancy, and for monitoring the levels of PTH or PTHrP during cancer therapy. This method involves assaying binding of the recombinant parathyroid hormone receptor of the invention to PTH or PTHrP present in a tissue sample, using the binding assay described herein. The level of binding may be determined directly (e.g., by using radioactively labelled PTH receptor, and assaying the radioactivity bound to endogenous PTH). Alternatively, binding of PTH receptor to the sample (e.g., a tissue section) may be followed by staining of the tissue sections with an antibody specific for the PTH receptor, using standard immunological techniques (Chin et al., Hybridoma 5:339, 1986).

In a third diagnostic approach, one could stably transfect cell lines (by the methods described in Ausubel et al., *Current Protocols in Molecular Biology*, Wiley Publishers, New York, 1987) with a PTH receptor gene linked to an appropriate promoter (e.g., the metallothionine promoter). Alternatively, the PTH/PTHrP receptor could be expressed from a eukaryotic vector, i.e., pcDNAI, and cotransfected with a mutant DHFR gene that will allow further gene amplification via methotrexate selection (Simonsen et al., Proc. Natl. Acad. Sci., 80:2495–2499, 1983). Such high-level expression of the gene produces an immortal cell line which is oversensitive to PTH or PTHrP. Such cells provide a particularly useful tool for detecting serum blood levels of PTH or PTHrP. Such a cell line may be used for diagnosis of conditions involving elevated PTH or PTHrP levels (e.g., those described above) or for conditions involving unusually low levels of PTH or PTHrP (e.g., those described above). Such a cell line is also useful for monitoring the regression or increase of PTH or PTHrP levels during therapy for hypercalcemia or hypocalcemia, respectively.

A patient who is suspected of being hypercalcemic may be treated using the compounds of the invention. Rapid intervention is important because symptoms may appear abruptly and, unless reversed, can be fatal. In one application, serum calcium levels are stabilized by an immediate course of treatment which includes antagonists of PTH or PTHrP. Such antagonists include the compounds of the invention which have been determined (by the assays described herein) to interfere with PTH receptor-mediated cell activation. To administer the antagonist, the appropriate antibody or peptide (is used in the manufacture of a medicament, generally by being formulated in an appropriate carrier such as physiological saline, and administered intravenously, at a dosage that provides adequate competition for PTH or PTHrP binding to the PTH receptor (e.g., a dosage sufficient to lower the serum calcium level to below 10 mg/dl). Typical dosage would be 1 ng to 10 mg of the antibody or peptide per kg body weight per day. Treatment may be repeated as necessary for long term maintenance of acceptable calcium levels (i.e., levels <10.1 mg/dl). This may be necessary for acute treatment of an underlying disease condition triggering hypercalcemia; or it may used, e.g., for chronic treatment of conditions such as osteoporosis.

In another application, the compounds of the invention which have been characterized, according to the methods of the invention, to be agonists are used therapeutically to treat hypocalcemia: e.g., that resulting from the partial or complete surgical removal of the parathyroid glands. Agonists may be formulated in a suitable carrier (e.g., physiological saline) and are preferably administered intravenously in a dosage that causes a rise in serum calcium to an acceptable level (i.e., approximately 8 mg/dl). A useful dosage range would be 1 ng to 10 mg of the agonist per kg body weight per day. Treatment may be repeated as necessary to maintain suitable serum calcium levels; long term treatment may be necessary for patients who have undergone parathyroid gland removal.

The nucleic acids of the invention may also be used therapeutically. Oligonucleotides which are antisense to PTH receptor MRNA (or nucleic acid constructs which express RNA that is antisense to PTH receptor mRNA) may be utilized as an anticancer therapy. This approach is useful, e.g., for hypercalcemias resulting from a genomic rearrangement or amplification which increases the amount or activity of PTH receptor, PTH or PTHrP. The method would involve introduction of the antisense oligonucleotide into the tumor cells in vivo. The antisense strand hybridizes with endogenous PTH receptor mRNA, interfering with translation of the protein, thereby reducing production of PTH receptor in such cells, and reducing PTH/PTHrP-associated neoplastic growth. Methods for antisense design and introduction into host cells are described, for example, in Weinberg et al., U.S. Pat. No. 4,740,463, herein incorporated by reference.

The biochemical characterization of the OK-H, OK-O and R15B PTH/PTHrP receptors of the invention demonstrate that the two transduction pathways now known to be triggered by the interaction of PTH with its receptor are distinct and may be separated. The predicted amino acid sequences of these receptors indicate that OK-H, which does not appear to activate inositol phosphate metabolism to any detectable degree, is 70 amino acids shorter at the carboxy-terminus than OK-O or R15B. By using the sequences of the invention and the information disclosed herein, one could clone and then alter (e.g. by site-directed mutagenesis) PTH/PTHrP receptor genes from any species to generate PTH/PTHrP receptors which do not activate phospholipase C. This could potentially allow the separation of different PTH-mediated actions, including bone resorption and bone formation, and could of great importance for the treatment of various bone disorders such as osteoporosis.

Nucleic acids of the invention which encode a PTH receptor may also be linked to a selected tissue-specific promoter and/or enhancer and the resultant hybrid gene introduced, by standard methods (e.g., as described by Leder et al., U.S. Pat. No. 4,736,866, herein incorporated by reference), into an animal embryo at an early developmental stage (e.g., the fertilized oocyte stage), to produce a transgenic animal which expresses elevated levels of PTH receptor in selected tissues (e.g., the osteo calcin promoter for bone). Such promoters are used to direct tissue-specific expression of the PTH receptor in the transgenic animal. The form of PTH receptor utilized can be one which encodes a PTH receptor similar to that of the animal species used, or it can encode the PTH receptor homolog of a different species. In one particular example, transgenic chickens are engineered to express the PTH receptor from a promoter which directs high-level expression in chicken oviducts. Such an animal is expected to produce eggs with higher calcium content, and thus harder shells.

OTHER EMBODIMENTS

Other embodiments are within the following claims. For example, the nucleic acid of the invention includes genes or cDNAs or RNAs originally isolated from any vertebrate species, including birds or mammals such as marsupials, rodents, or humans. The high degree of homology demonstrated for the PTH receptors from such diverse species as opossum, rat, and human indicates that the methods of isolating PTH receptors disclosed herein will be broadly applicable to the isolation of related cell receptors from a wide variety of species.

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 1862 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 98..1643

( x i ) SEQUENCE DESCRIPTION: SEQ ID NO:1:

```
TGGGCACAGC  CACCCTGTTG  GTAGTCCAGG  GGCCAGCCCA  CTGAGCTGGC  ATATCAGCTG         60

GTGGCCCCGT  TGGACTCGGC  CCTAGGGAAC  GGCGGCG ATG  GGA  GCG  CCC  CGG  ATC      115
                                           Met  Gly  Ala  Pro  Arg  Ile
                                            1                         5

TCG  CAC  AGC  CTT  GCC  TTG  CTC  CTC  TGC  TGC  TCC  GTG  CTC  AGC  TCC  GTC    163
Ser  His  Ser  Leu  Ala  Leu  Leu  Leu  Cys  Cys  Ser  Val  Leu  Ser  Ser  Val
               10                        15                       20

TAC  GCA  CTG  GTG  GAT  GCC  GAT  GAT  GTC  ATA  ACG  AAG  GAG  GAG  CAG  ATC    211
Tyr  Ala  Leu  Val  Asp  Ala  Asp  Asp  Val  Ile  Thr  Lys  Glu  Glu  Gln  Ile
               25                        30                       35

ATT  CTT  CTG  CGC  AAT  GCC  CAG  GCC  CAG  TGT  GAG  CAG  CGC  CTG  AAA  GAG    259
Ile  Leu  Leu  Arg  Asn  Ala  Gln  Ala  Gln  Cys  Glu  Gln  Arg  Leu  Lys  Glu
               40                        45                       50
```

```
GTC CTC AGG GTC CCT GAA CTT GCT GAA TCT GCC AAA GAC TGG ATG TCA      307
Val Leu Arg Val Pro Glu Leu Ala Glu Ser Ala Lys Asp Trp Met Ser
 55              60                  65                  70

AGG TCT GCA AAG ACA AAG AAG GAG AAA CCT GCA GAA AAG CTT TAT CCC      355
Arg Ser Ala Lys Thr Lys Lys Glu Lys Pro Ala Glu Lys Leu Tyr Pro
                 75                  80                  85

CAG GCA GAG GAG TCC AGG GAA GTT TCT GAC AGG AGC CGG CTG CAG GAT      403
Gln Ala Glu Glu Ser Arg Glu Val Ser Asp Arg Ser Arg Leu Gln Asp
                     90                  95                 100

GGC TTC TGC CTA CCT GAG TGG GAC AAC ATT GTG TGC TGG CCT GCT GGA      451
Gly Phe Cys Leu Pro Glu Trp Asp Asn Ile Val Cys Trp Pro Ala Gly
            105                 110                 115

GTG CCC GGC AAG GTG GTG GCC GTG CCC TGC CCC GAC TAC TTC TAC GAC      499
Val Pro Gly Lys Val Val Ala Val Pro Cys Pro Asp Tyr Phe Tyr Asp
    120                 125                 130

TTC AAC CAC AAA GGC CGA GCC TAT CGG CGC TGT GAC AGC AAT GGC AGC      547
Phe Asn His Lys Gly Arg Ala Tyr Arg Arg Cys Asp Ser Asn Gly Ser
135                 140                 145                 150

TGG GAG CTG GTG CCT GGG AAC AAC CGG ACA TGG GCG AAT TAC AGC GAA      595
Trp Glu Leu Val Pro Gly Asn Asn Arg Thr Trp Ala Asn Tyr Ser Glu
                155                 160                 165

TGT GTC AAG TTT CTG ACC AAC GAG ACC CGG GAA CGG GAA GTC TTT GAT      643
Cys Val Lys Phe Leu Thr Asn Glu Thr Arg Glu Arg Glu Val Phe Asp
            170                 175                 180

CGC CTC GGA ATG ATC TAC ACT GTG GGC TAC TCC ATC TCT CTG GGC TCC      691
Arg Leu Gly Met Ile Tyr Thr Val Gly Tyr Ser Ile Ser Leu Gly Ser
    185                 190                 195

CTC ACT GTG GCT GTG CTG ATT CTG GGT TAC TTT AGG AGG TTA CAT TGC      739
Leu Thr Val Ala Val Leu Ile Leu Gly Tyr Phe Arg Arg Leu His Cys
    200                 205                 210

ACC CGA AAC TAC ATT CAC ATG CAT CTC TTC GTG TCC TTT ATG CTC CGG      787
Thr Arg Asn Tyr Ile His Met His Leu Phe Val Ser Phe Met Leu Arg
215                 220                 225                 230

GCT GTA AGC ATC TTC ATC AAG GAT GCT GTG CTC TAC TCG GGG TTC TCC      835
Ala Val Ser Ile Phe Ile Lys Asp Ala Val Leu Tyr Ser Gly Val Ser
            235                 240                 245

ACA GAT GAA ATC GAG CGC ATC ACC GAG GAG GAG CTG AGG GCC TTC ACA      883
Thr Asp Glu Ile Glu Arg Ile Thr Glu Glu Glu Leu Arg Ala Phe Thr
                250                 255                 260

GAG CCT CCC CCT GCT GAC AAG GCG GGT TTT GTG GGC TGC AGA GTG GCG      931
Glu Pro Pro Pro Ala Asp Lys Ala Gly Phe Val Gly Cys Arg Val Ala
            265                 270                 275

GTA ACC GTC TTC CTT TAC TTC CTG ACC ACC AAC TAC TAC TGG ATC CTG      979
Val Thr Val Phe Leu Tyr Phe Leu Thr Thr Asn Tyr Tyr Trp Ile Leu
    280                 285                 290

GTG GAA GGC CTC TAC CTT CAC AGC CTC ATC TTC ATG GCT TTT TCT TCT     1027
Val Glu Gly Leu Tyr Leu His Ser Leu Ile Phe Met Ala Phe Phe Ser
295                 300                 305                 310

GAG AAA AAG TAT CTC TGG GGT TTC ACA TTA TTT GGC TGG GGC CTC CCT     1075
Glu Lys Lys Tyr Leu Trp Gly Phe Thr Leu Phe Gly Trp Gly Leu Pro
            315                 320                 325

GCC GTG TTT GTC GCT GTG TGG GTG ACC GTG AGG GCT ACA CTG GCC AAC     1123
Ala Val Phe Val Ala Val Trp Val Thr Val Arg Ala Thr Leu Ala Asn
        330                 335                 340

ACT GAG TGC TGG GAC CTG AGT TCG GGG AAT AAG AAA TGG ATC ATA CAG     1171
Thr Glu Cys Trp Asp Leu Ser Ser Gly Asn Lys Lys Trp Ile Ile Gln
        345                 350                 355

GTG CCC ATC CTG GCA GCT ATT GTG GTG AAC TTT ATT CTT TTT ATC AAT     1219
Val Pro Ile Leu Ala Ala Ile Val Val Asn Phe Ile Leu Phe Ile Asn
    360                 365                 370
```

| | | | | | | | | | | | | | | | | |
|---|---|---|---|---|---|---|---|---|---|---|---|---|---|---|---|---|
| ATA | ATC | AGA | GTC | CTG | GCT | ACT | AAA | CTC | CGG | GAG | ACC | AAT | GCA | GGG | AGA | 1267 |
| Ile | Ile | Arg | Val | Leu | Ala | Thr | Lys | Leu | Arg | Glu | Thr | Asn | Ala | Gly | Arg | |
| 375 | | | | 380 | | | | | 385 | | | | | 390 | | |
| TGT | GAC | ACG | AGG | CAA | CAG | TAT | AGA | AAG | CTG | CTG | AAG | TCC | ACG | CTA | GTC | 1315 |
| Cys | Asp | Thr | Arg | Gln | Gln | Tyr | Arg | Lys | Leu | Leu | Lys | Ser | Thr | Leu | Val | |
| | | | | 395 | | | | | 400 | | | | | 405 | | |
| CTC | ATG | CCG | CTA | TTT | GGG | GTG | CAC | TAC | ATC | GTC | TTC | ATG | GCC | ACG | CCG | 1363 |
| Leu | Met | Pro | Leu | Phe | Gly | Val | His | Tyr | Ile | Val | Phe | Met | Ala | Thr | Pro | |
| | | | 410 | | | | | 415 | | | | | 420 | | | |
| TAC | ACA | GAA | GTA | TCA | GGG | ATT | CTT | TGG | CAA | GTC | CAA | ATG | CAC | TAT | GAA | 1411 |
| Tyr | Thr | Glu | Val | Ser | Gly | Ile | Leu | Trp | Gln | Val | Gln | Met | His | Tyr | Glu | |
| | | 425 | | | | | 430 | | | | | 435 | | | | |
| ATG | CTC | TTC | AAT | TCA | TTC | CAG | GGA | TTT | TTC | GTT | GCC | ATT | ATA | TAC | TGT | 1459 |
| Met | Leu | Phe | Asn | Ser | Phe | Gln | Gly | Phe | Phe | Val | Ala | Ile | Ile | Tyr | Cys | |
| | | 440 | | | | | 445 | | | | | 450 | | | | |
| TTC | TGC | AAT | GGA | GAG | GTA | CAA | GCA | GAG | ATC | AAG | AAG | TCA | TGG | AGC | CGA | 1507 |
| Phe | Cys | Asn | Gly | Glu | Val | Gln | Ala | Glu | Ile | Lys | Lys | Ser | Trp | Ser | Arg | |
| 455 | | | | | 460 | | | | | 465 | | | | | 470 | |
| TGG | ACC | CTG | GCC | TTG | GAC | TTC | AAG | CGG | AAG | GCC | CGG | AGT | GGC | AGC | AGT | 1555 |
| Trp | Thr | Leu | Ala | Leu | Asp | Phe | Lys | Arg | Lys | Ala | Arg | Ser | Gly | Ser | Ser | |
| | | | | 475 | | | | | 480 | | | | | 485 | | |
| ACC | TAC | AGC | TAT | GGC | CCC | ATG | GTG | TCA | CAT | ACA | AGT | GTC | ACC | AAT | GTG | 1603 |
| Thr | Tyr | Ser | Tyr | Gly | Pro | Met | Val | Ser | His | Thr | Ser | Val | Thr | Asn | Val | |
| | | | 490 | | | | | 495 | | | | | 500 | | | |
| GGA | CCT | CGA | GGG | GGC | TGG | CCT | TGT | CCC | TCA | GCC | CTC | GAC | T | AGCTCCTGGG | | 1653 |
| Gly | Pro | Arg | Gly | Gly | Trp | Pro | Cys | Pro | Ser | Ala | Leu | Asp | | | | |
| | | 505 | | | | | 510 | | | | | 515 | | | | |

GCTGGAGCCA GTGCCAATGG CCATCACCAG TTGCCTGGCT ATGTGAAGCA TGGTTCCATT    1713

TCTGAGAACT CATTGCCTTC ATCTGGCCCA GAGCCTGGCA CCAAAGATGA CGGGTATCTC    1773

AATGGCTCTG GACTTTATGA GCCAATGGTT GGGGAACAGC CCCCTCCACT CCTGGAGGAG    1833

GAGAGAGAGA CAGTCATGTG ACCCATATC    1862

( 2 ) INFORMATION FOR SEQ ID NO:2:

( i ) SEQUENCE CHARACTERISTICS:
        ( A ) LENGTH: 1863 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 98..1853

( x i ) SEQUENCE DESCRIPTION: SEQ ID NO:2:

TGGGCACAGC CACCCTGTTG GTAGTCCAGG GGCCAGCCCA CTGAGCTGGC ATATCAGCTG    60

GTGGCCCCGT TGGACTCGGC CCTAGGGAAC GGCGGCG ATG GGA GCG CCC CGG ATC    115
                                                            Met Gly Ala Pro Arg Ile
                                                                           520

| | | | | | | | | | | | | | | | | |
|---|---|---|---|---|---|---|---|---|---|---|---|---|---|---|---|---|
| TCG | CAC | AGC | CTT | GCC | TTG | CTC | CTC | TGC | TGC | TCC | GTG | CTC | AGC | TCC | GTC | 163 |
| Ser | His | Ser | Leu | Ala | Leu | Leu | Leu | Cys | Cys | Ser | Val | Leu | Ser | Ser | Val | |
| | | | 525 | | | | | 530 | | | | | 535 | | | |
| TAC | GCA | CTG | GTG | GAT | GCC | GAT | GAT | GTC | ATA | ACG | AAG | GAG | GAG | CAG | ATC | 211 |
| Tyr | Ala | Leu | Val | Asp | Ala | Asp | Asp | Val | Ile | Thr | Lys | Glu | Glu | Gln | Ile | |
| | | | 540 | | | | | 545 | | | | | 550 | | | |
| ATT | CTT | CTG | CGC | AAT | GCC | CAG | GCC | CAG | TGT | GAG | CAG | CGC | CTG | AAA | GAG | 259 |
| Ile | Leu | Leu | Arg | Asn | Ala | Gln | Ala | Gln | Cys | Glu | Gln | Arg | Leu | Lys | Glu | |
| | | 555 | | | | | 560 | | | | | 565 | | | | |
| GTC | CTC | AGG | GTC | CCT | GAA | CTT | GCT | GAA | TCT | GCC | AAA | GAC | TGG | ATG | TCA | 307 |
| Val | Leu | Arg | Val | Pro | Glu | Leu | Ala | Glu | Ser | Ala | Lys | Asp | Trp | Met | Ser | |

|  |  |  |  |  |  |  |  |  |  |  |  |  |  |  |  |  |
|---|---|---|---|---|---|---|---|---|---|---|---|---|---|---|---|---|
| 570 | | | | | 575 | | | | | 580 | | | | | 585 | |

```
AGG  TCT  GCA  AAG  ACA  AAG  AAG  GAG  AAA  CCT  GCA  GAA  AAG  CTT  TAT  CCC       355
Arg  Ser  Ala  Lys  Thr  Lys  Lys  Glu  Lys  Pro  Ala  Glu  Lys  Leu  Tyr  Pro
                    590            595                      600

CAG  GCA  GAG  GAG  TCC  AGG  GAA  GTT  TCT  GAC  AGG  AGC  CGG  CTG  CAG  GAT       403
Gln  Ala  Glu  Glu  Ser  Arg  Glu  Val  Ser  Asp  Arg  Ser  Arg  Leu  Gln  Asp
                    605                 610                      615

GGC  TTC  TGC  CTA  CCT  GAG  TGG  GAC  AAC  ATT  GTG  TGC  TGG  CCT  GCT  GGA       451
Gly  Phe  Cys  Leu  Pro  Glu  Trp  Asp  Asn  Ile  Val  Cys  Trp  Pro  Ala  Gly
               620                      625                      630

GTG  CCC  GGC  AAG  GTG  GTG  GCC  GTG  CCC  TGC  CCC  GAC  TAC  TTC  TAC  GAC       499
Val  Pro  Gly  Lys  Val  Val  Ala  Val  Pro  Cys  Pro  Asp  Tyr  Phe  Tyr  Asp
          635                 640                           645

TTC  AAC  CAC  AAA  GGC  CGA  GCC  TAT  CGG  CGC  TGT  GAC  AGC  AAT  GGC  AGC       547
Phe  Asn  His  Lys  Gly  Arg  Ala  Tyr  Arg  Arg  Cys  Asp  Ser  Asn  Gly  Ser
650                      655                 660                           665

TGG  GAG  CTG  GTG  CCT  GGG  AAC  AAC  CGG  ACA  TGG  GCG  AAT  TAC  AGC  GAA       595
Trp  Glu  Leu  Val  Pro  Gly  Asn  Asn  Arg  Thr  Trp  Ala  Asn  Tyr  Ser  Glu
                         670                 675                      680

TGT  GTC  AAG  TTT  CTG  ACC  AAC  GAG  ACC  CGG  GAA  CGG  GAA  GTC  TTT  GAT       643
Cys  Val  Lys  Phe  Leu  Thr  Asn  Glu  Thr  Arg  Glu  Arg  Glu  Val  Phe  Asp
                    685                 690                      695

CGC  CTC  GGA  ATG  ATC  TAC  ACT  GTG  GGC  TAC  TCC  ATC  TCT  CTG  GGC  TCC       691
Arg  Leu  Gly  Met  Ile  Tyr  Thr  Val  Gly  Tyr  Ser  Ile  Ser  Leu  Gly  Ser
               700                      705                 710

CTC  ACT  GTG  GCT  GTG  CTG  ATT  CTG  GGT  TAC  TTT  AGG  AGG  TTA  CAT  TGC       739
Leu  Thr  Val  Ala  Val  Leu  Ile  Leu  Gly  Tyr  Phe  Arg  Arg  Leu  His  Cys
     715                      720                      725

ACC  CGA  AAC  TAC  ATT  CAC  ATG  CAT  CTC  TTC  GTG  TCC  TTT  ATG  CTC  CGG       787
Thr  Arg  Asn  Tyr  Ile  His  Met  His  Leu  Phe  Val  Ser  Phe  Met  Leu  Arg
730                      735                      740                      745

GCT  GTA  AGC  ATC  TTC  ATC  AAG  GAT  GCT  GTG  CTC  TAC  TCG  GGG  GTT  TCC       835
Ala  Val  Ser  Ile  Phe  Ile  Lys  Asp  Ala  Val  Leu  Tyr  Ser  Gly  Val  Ser
                    750                      755                      760

ACA  GAT  GAA  ATC  GAG  CGC  ATC  ACC  GAG  GAG  GAG  CTG  AGG  GCC  TTC  ACA       883
Thr  Asp  Glu  Ile  Glu  Arg  Ile  Thr  Glu  Glu  Glu  Leu  Arg  Ala  Phe  Thr
               765                      770                      775

GAG  CCT  CCC  CCT  GCT  GAC  AAG  GCG  GGT  TTT  GTG  GGC  TGC  AGA  GTG  GCG       931
Glu  Pro  Pro  Pro  Ala  Asp  Lys  Ala  Gly  Phe  Val  Gly  Cys  Arg  Val  Ala
          780                      785                      790

GTA  ACC  GTC  TTC  CTT  TAC  TTC  CTG  ACC  ACC  AAC  TAC  TAC  TGG  ATC  CTG       979
Val  Thr  Val  Phe  Leu  Tyr  Phe  Leu  Thr  Thr  Asn  Tyr  Tyr  Trp  Ile  Leu
     795                      800                      805

GTG  GAA  GGC  CTC  TAC  CTT  CAC  AGC  CTC  ATC  TTC  ATG  GCT  TTT  TTC  TCT      1027
Val  Glu  Gly  Leu  Tyr  Leu  His  Ser  Leu  Ile  Phe  Met  Ala  Phe  Phe  Ser
810                 815                      820                      825

GAG  AAA  AAG  TAT  CTC  TGG  GGT  TTC  ACA  TTA  TTT  GGC  TGG  GGC  CTC  CCT      1075
Glu  Lys  Lys  Tyr  Leu  Trp  Gly  Phe  Thr  Leu  Phe  Gly  Trp  Gly  Leu  Pro
                    830                      835                      840

GCC  GTG  TTT  GTC  GCT  GTG  TGG  GTG  ACC  GTG  AGG  GCT  ACA  CTG  GCC  AAC      1123
Ala  Val  Phe  Val  Ala  Val  Trp  Val  Thr  Val  Arg  Ala  Thr  Leu  Ala  Asn
               845                      850                      855

ACT  GAG  TGC  TGG  GAC  CTG  AGT  TCG  GGG  AAT  AAG  AAA  TGG  ATC  ATA  CAG      1171
Thr  Glu  Cys  Trp  Asp  Leu  Ser  Ser  Gly  Asn  Lys  Lys  Trp  Ile  Ile  Gln
          860                      865                      870

GTG  CCC  ATC  CTG  GCA  GCT  ATT  GTG  GTG  AAC  TTT  ATT  CTT  TTT  ATC  AAT      1219
Val  Pro  Ile  Leu  Ala  Ala  Ile  Val  Val  Asn  Phe  Ile  Leu  Phe  Ile  Asn
     875                      880                      885

ATA  ATC  AGA  GTC  CTG  GCT  ACT  AAA  CTC  CGG  GAG  ACC  AAT  GCA  GGG  AGA      1267
Ile  Ile  Arg  Val  Leu  Ala  Thr  Lys  Leu  Arg  Glu  Thr  Asn  Ala  Gly  Arg
```

```
                     8 9 0                          8 9 5                          9 0 0                          9 0 5
TGT   GAC   ACG   AGG   CAA   CAG   TAT   AGA   AAG   CTG   CTG   AAG   TCC   ACG   CTA   GTC              1 3 1 5
Cys   Asp   Thr   Arg   Gln   Gln   Tyr   Arg   Lys   Leu   Leu   Lys   Ser   Thr   Leu   Val
                  9 1 0                                         9 1 5                           9 2 0

CTC   ATG   CCG   CTA   TTT   GGG   GTG   CAC   TAC   ATC   GTC   TTC   ATG   GCC   ACG   CCG              1 3 6 3
Leu   Met   Pro   Leu   Phe   Gly   Val   His   Tyr   Ile   Val   Phe   Met   Ala   Thr   Pro
                  9 2 5                                         9 3 0                           9 3 5

TAC   ACA   GAA   GTA   TCA   GGG   ATT   CTT   TGG   CAA   GTC   CAA   ATG   CAC   TAT   GAA              1 4 1 1
Tyr   Thr   Glu   Val   Ser   Gly   Ile   Leu   Trp   Gln   Val   Gln   Met   His   Tyr   Glu
                  9 4 0                                         9 4 5                           9 5 0

ATG   CTC   TTC   AAT   TCA   TTC   CAG   GGA   TTT   TTC   GTT   GCC   ATT   ATA   TAC   TGT              1 4 5 9
Met   Leu   Phe   Asn   Ser   Phe   Gln   Gly   Phe   Phe   Val   Ala   Ile   Ile   Tyr   Cys
      9 5 5                                         9 6 0                           9 6 5

TTC   TGC   AAT   GGA   GAG   GTA   CAA   GCA   GAG   ATC   AAG   AAG   TCA   TGG   AGC   CGA              1 5 0 7
Phe   Cys   Asn   Gly   Glu   Val   Gln   Ala   Glu   Ile   Lys   Lys   Ser   Trp   Ser   Arg
9 7 0                                   9 7 5                           9 8 0                   9 8 5

TGG   ACC   CTG   GCC   TTG   GAC   TTC   AAG   CGG   AAG   GCC   CGG   AGT   GGC   AGC   AGT              1 5 5 5
Trp   Thr   Leu   Ala   Leu   Asp   Phe   Lys   Arg   Lys   Ala   Arg   Ser   Gly   Ser   Ser
                              9 9 0                             9 9 5                           1 0 0 0

ACC   TAC   AGC   TAT   GGC   CCC   ATG   GTG   TCA   CAT   ACA   AGT   GTC   ACC   AAT   GTG              1 6 0 3
Thr   Tyr   Ser   Tyr   Gly   Pro   Met   Val   Ser   His   Thr   Ser   Val   Thr   Asn   Val
                        1 0 0 5                             1 0 1 0                     1 0 1 5

GGA   CCT   CGA   GGG   GGG   CTG   GCC   TTG   TCC   CTC   AGC   CCT   CGA   CTA   GCT   CCT              1 6 5 1
Gly   Pro   Arg   Gly   Gly   Leu   Ala   Leu   Ser   Leu   Ser   Pro   Arg   Leu   Ala   Pro
            1 0 2 0                               1 0 2 5                       1 0 3 0

GGG   GCT   GGA   GCC   AGT   GCC   AAT   GGC   CAT   CAC   CAG   TTG   CCT   GGC   TAT   GTG              1 6 9 9
Gly   Ala   Gly   Ala   Ser   Ala   Asn   Gly   His   His   Gln   Leu   Pro   Gly   Tyr   Val
            1 0 3 5                               1 0 4 0                       1 0 4 5

AAG   CAT   GGT   TCC   ATT   TCT   GAG   AAC   TCA   TTG   CCT   TCA   TCT   GGC   CCA   GAG              1 7 4 7
Lys   His   Gly   Ser   Ile   Ser   Glu   Asn   Ser   Leu   Pro   Ser   Ser   Gly   Pro   Glu
1 0 5 0                                 1 0 5 5                         1 0 6 0                 1 0 6 5

CCT   GGC   ACC   AAA   GAT   GAC   GGG   TAT   CTC   AAT   GGC   TCT   GGA   CTT   TAT   GAG              1 7 9 5
Pro   Gly   Thr   Lys   Asp   Asp   Gly   Tyr   Leu   Asn   Gly   Ser   Gly   Leu   Tyr   Glu
                        1 0 7 0                             1 0 7 5                     1 0 8 0

CCA   ATG   GTT   GGG   GAA   CAG   CCC   CCT   CCA   CTC   CTG   GAG   GAG   GAG   AGA   GAG              1 8 4 3
Pro   Met   Val   Gly   Glu   Gln   Pro   Pro   Pro   Leu   Leu   Glu   Glu   Glu   Arg   Glu
                        1 0 8 5                             1 0 9 0                     1 0 9 5

ACA   GTC   ATG         T   GACCCATATC                                                                    1 8 6 3
Thr   Val   Met
            1 1 0 0
```

( 2 ) INFORMATION FOR SEQ ID NO:3:

( i ) SEQUENCE CHARACTERISTICS:
        ( A ) LENGTH: 2051 base pairs
        ( B ) TYPE: nucleic acid
        ( C ) STRANDEDNESS: single
        ( D ) TOPOLOGY: linear ( i x ) FEATURE:
        ( A ) NAME/KEY: CDS
        ( B ) LOCATION: 73..1846

( x i ) SEQUENCE DESCRIPTION: SEQ ID NO:3:

```
GGCGGGGGCC   GCGGCGGCGA   GCTCGGAGGC   CGGCGGCGGC   TGCCCCGAGG   GACGCGGCCC              6 0

TAGGCGGTGG   CG   ATG   GGG   GCC   GCC   CGG   ATC   GCA   CCC   AGC   CTG   GCG   CTC              1 0 8
                Met   Gly   Ala   Ala   Arg   Ile   Ala   Pro   Ser   Leu   Ala   Leu
                                  5 9 0                                     5 9 5

CTA   CTC   TGC   TGC   CCA   GTG   CTC   AGC   TCC   GCA   TAT   GCG   CTG   GTG   GAT   GCG              1 5 6
Leu   Leu   Cys   Cys   Pro   Val   Leu   Ser   Ser   Ala   Tyr   Ala   Leu   Val   Asp   Ala
            6 0 0                                   6 0 5                           6 1 0

GAC   GAT   GTC   TTT   ACC   AAA   GAG   GAA   CAG   ATT   TTC   CTG   CTG   CAC   CGT   GCC              2 0 4
```

-continued

| | | | | | | | | | | | | | | | |
|---|---|---|---|---|---|---|---|---|---|---|---|---|---|---|---|
| Asp | Asp | Val | Phe | Thr | Lys | Glu | Glu | Gln | Ile | Phe | Leu | Leu | His | Arg | Ala |
| | 615 | | | | 620 | | | | | 625 | | | | | |

| CAG | GCG | CAA | TGT | GAC | AAG | CTG | CTC | AAG | GAA | GTT | CTG | CAC | ACA | GCA | GCC | 252 |
|---|---|---|---|---|---|---|---|---|---|---|---|---|---|---|---|---|
| Gln | Ala | Gln | Cys | Asp | Lys | Leu | Leu | Lys | Glu | Val | Leu | His | Thr | Ala | Ala | |
| 630 | | | | 635 | | | | | 640 | | | | | | 645 | |

| AAC | ATA | ATG | GAG | TCA | GAC | AAG | GGC | TGG | ACA | CCA | GCA | TCT | ACG | TCA | GGG | 300 |
|---|---|---|---|---|---|---|---|---|---|---|---|---|---|---|---|---|
| Asn | Ile | Met | Glu | Ser | Asp | Lys | Gly | Trp | Thr | Pro | Ala | Ser | Thr | Ser | Gly | |
| | | | | 650 | | | | | 655 | | | | | | 660 | |

| AAG | CCC | AGG | AAA | GAG | AAG | GCA | TCG | GGA | AAG | TTC | TAC | CCT | GAG | TCT | AAA | 348 |
|---|---|---|---|---|---|---|---|---|---|---|---|---|---|---|---|---|
| Lys | Pro | Arg | Lys | Glu | Lys | Ala | Ser | Gly | Lys | Phe | Tyr | Pro | Glu | Ser | Lys | |
| | | | 665 | | | | | 670 | | | | | 675 | | | |

| GAG | AAC | AAG | GAC | GTG | CCC | ACC | GGC | AGC | AGG | CGC | AGA | GGG | CGT | CCC | TGT | 396 |
|---|---|---|---|---|---|---|---|---|---|---|---|---|---|---|---|---|
| Glu | Asn | Lys | Asp | Val | Pro | Thr | Gly | Ser | Arg | Arg | Arg | Gly | Arg | Pro | Cys | |
| | | 680 | | | | | 685 | | | | | 690 | | | | |

| CTG | CCC | GAG | TGG | GAC | AAC | ATC | GTT | TGC | TGG | CCA | TTA | GGG | GCA | CCA | GGT | 444 |
|---|---|---|---|---|---|---|---|---|---|---|---|---|---|---|---|---|
| Leu | Pro | Glu | Trp | Asp | Asn | Ile | Val | Cys | Trp | Pro | Leu | Gly | Ala | Pro | Gly | |
| | | 695 | | | | | 700 | | | | | 705 | | | | |

| GAA | GTG | GTG | GCA | GTA | CCT | TGT | CCC | GAT | TAC | ATT | TAT | GAC | TTC | AAT | CAC | 492 |
|---|---|---|---|---|---|---|---|---|---|---|---|---|---|---|---|---|
| Glu | Val | Val | Ala | Val | Pro | Cys | Pro | Asp | Tyr | Ile | Tyr | Asp | Phe | Asn | His | |
| 710 | | | | | 715 | | | | | 720 | | | | | 725 | |

| AAA | GGC | CAT | GCC | TAC | AGA | CGC | TGT | GAC | CGC | AAT | GGC | AGC | TGG | GAG | GTG | 540 |
|---|---|---|---|---|---|---|---|---|---|---|---|---|---|---|---|---|
| Lys | Gly | His | Ala | Tyr | Arg | Arg | Cys | Asp | Arg | Asn | Gly | Ser | Trp | Glu | Val | |
| | | | | 730 | | | | | 735 | | | | | | 740 | |

| GTT | CCA | GGG | CAC | AAC | CGG | ACG | TGG | GCC | AAC | TAC | AGC | GAG | TGC | CTC | AAG | 588 |
|---|---|---|---|---|---|---|---|---|---|---|---|---|---|---|---|---|
| Val | Pro | Gly | His | Asn | Arg | Thr | Trp | Ala | Asn | Tyr | Ser | Glu | Cys | Leu | Lys | |
| | | | 745 | | | | | 750 | | | | | 755 | | | |

| TTC | ATG | ACC | AAT | GAG | ACG | CGG | GAA | CGG | GAG | GTA | TTT | GAC | CGC | CTA | GGC | 636 |
|---|---|---|---|---|---|---|---|---|---|---|---|---|---|---|---|---|
| Phe | Met | Thr | Asn | Glu | Thr | Arg | Glu | Arg | Glu | Val | Phe | Asp | Arg | Leu | Gly | |
| | | 760 | | | | | 765 | | | | | 770 | | | | |

| ATG | ATC | TAC | ACC | GTG | GGA | TAC | TCC | ATG | TCT | CTC | GCC | TCC | CTC | ACG | GTG | 684 |
|---|---|---|---|---|---|---|---|---|---|---|---|---|---|---|---|---|
| Met | Ile | Tyr | Thr | Val | Gly | Tyr | Ser | Met | Ser | Leu | Ala | Ser | Leu | Thr | Val | |
| | 775 | | | | | 780 | | | | | 785 | | | | | |

| GCT | GTG | CTC | ATC | CTG | GCC | TAT | TTT | AGG | CGG | CTG | CAC | TGC | ACG | CGC | AAC | 732 |
|---|---|---|---|---|---|---|---|---|---|---|---|---|---|---|---|---|
| Ala | Val | Leu | Ile | Leu | Ala | Tyr | Phe | Arg | Arg | Leu | His | Cys | Thr | Arg | Asn | |
| 790 | | | | | 795 | | | | | 800 | | | | | 805 | |

| TAC | ATC | CAC | ATG | CAC | ATG | TTC | CTG | TCG | TTT | ATG | CTG | CGC | GCC | GCG | AGC | 780 |
|---|---|---|---|---|---|---|---|---|---|---|---|---|---|---|---|---|
| Tyr | Ile | His | Met | His | Met | Phe | Leu | Ser | Phe | Met | Leu | Arg | Ala | Ala | Ser | |
| | | | | 810 | | | | | 815 | | | | | | 820 | |

| ATC | TTC | GTG | AAG | GAC | GCT | GTG | CTC | TAC | TCT | GGC | TTC | ACG | CTG | GAT | GAG | 828 |
|---|---|---|---|---|---|---|---|---|---|---|---|---|---|---|---|---|
| Ile | Phe | Val | Lys | Asp | Ala | Val | Leu | Tyr | Ser | Gly | Phe | Thr | Leu | Asp | Glu | |
| | | | 825 | | | | | 830 | | | | | 835 | | | |

| GCC | GAG | CGC | CTC | ACA | GAG | GAA | GAG | TTG | CAC | ATC | ATC | GCG | CAG | GTG | CCA | 876 |
|---|---|---|---|---|---|---|---|---|---|---|---|---|---|---|---|---|
| Ala | Glu | Arg | Leu | Thr | Glu | Glu | Glu | Leu | His | Ile | Ile | Ala | Gln | Val | Pro | |
| | | 840 | | | | | 845 | | | | | 850 | | | | |

| CCT | CCG | CCG | GCC | GCT | GCC | GCC | GTA | GGC | TAC | GCT | GGC | TGC | CGC | GTG | GCG | 924 |
|---|---|---|---|---|---|---|---|---|---|---|---|---|---|---|---|---|
| Pro | Pro | Pro | Ala | Ala | Ala | Ala | Val | Gly | Tyr | Ala | Gly | Cys | Arg | Val | Ala | |
| 855 | | | | | 860 | | | | | 865 | | | | | | |

| GTG | ACC | TTC | TTC | CTC | TAC | TTC | CTG | GCT | ACC | AAC | TAC | TAC | TGG | ATT | CTG | 972 |
|---|---|---|---|---|---|---|---|---|---|---|---|---|---|---|---|---|
| Val | Thr | Phe | Phe | Leu | Tyr | Phe | Leu | Ala | Thr | Asn | Tyr | Tyr | Trp | Ile | Leu | |
| 870 | | | | | 875 | | | | | 880 | | | | | 885 | |

| GTG | GAG | GGG | CTG | TAC | TTG | CAC | AGC | CTC | ATC | TTC | ATG | GCC | TTT | TTC | TCA | 1020 |
|---|---|---|---|---|---|---|---|---|---|---|---|---|---|---|---|---|
| Val | Glu | Gly | Leu | Tyr | Leu | His | Ser | Leu | Ile | Phe | Met | Ala | Phe | Phe | Ser | |
| | | | | 890 | | | | | 895 | | | | | 900 | | |

| GAG | AAG | AAG | TAC | CTG | TGG | GGC | TTC | ACC | ATC | TTT | GGC | TGG | GGT | CTA | CCG | 1068 |
|---|---|---|---|---|---|---|---|---|---|---|---|---|---|---|---|---|
| Glu | Lys | Lys | Tyr | Leu | Trp | Gly | Phe | Thr | Ile | Phe | Gly | Trp | Gly | Leu | Pro | |
| | | | 905 | | | | | 910 | | | | | 915 | | | |

| GCT | GTC | TTC | GTG | GCT | GTG | TGG | GTC | GGT | GTC | AGA | GCA | ACC | TTG | GCC | AAC | 1116 |
|---|---|---|---|---|---|---|---|---|---|---|---|---|---|---|---|---|
| Ala | Val | Phe | Val | Ala | Val | Trp | Val | Gly | Val | Arg | Ala | Thr | Leu | Ala | Asn | |
| | | 920 | | | | | 925 | | | | | 930 | | | | |

| ACT | GGG | TGC | TGG | GAT | CTG | AGC | TCC | GGG | CAC | AAG | AAG | TGG | ATC | ATC | CAG | 1164 |

|   |   |   |   |   |   |   |   |   |   |   |   |   |   |   |   |
|---|---|---|---|---|---|---|---|---|---|---|---|---|---|---|---|
| Thr | Gly | Cys | Trp | Asp | Leu | Ser | Ser | Gly | His | Lys | Lys | Trp | Ile | Ile | Gln |
|  | 935 |  |  |  | 940 |  |  |  | 945 |  |  |  |  |  |  |

| GTG | CCC | ATC | CTG | GCA | TCT | GTT | GTG | CTC | AAC | TTC | ATC | CTT | TTT | ATC | AAC | 1212 |
|---|---|---|---|---|---|---|---|---|---|---|---|---|---|---|---|---|
| Val | Pro | Ile | Leu | Ala | Ser | Val | Val | Leu | Asn | Phe | Ile | Leu | Phe | Ile | Asn |  |
| 950 |  |  |  |  | 955 |  |  |  | 960 |  |  |  |  |  | 965 |  |

| ATC | ATC | CGG | GTG | CTT | GCC | ACT | AAG | CTT | CGG | GAG | ACC | AAT | GCG | GGC | CGG | 1260 |
|---|---|---|---|---|---|---|---|---|---|---|---|---|---|---|---|---|
| Ile | Ile | Arg | Val | Leu | Ala | Thr | Lys | Leu | Arg | Glu | Thr | Asn | Ala | Gly | Arg |  |
|  |  |  |  | 970 |  |  |  |  | 975 |  |  |  |  | 980 |  |  |

| TGT | GAC | ACC | AGG | CAG | CAG | TAC | CGG | AAG | CTG | CTC | AGG | TCC | ACG | TTG | GTG | 1308 |
|---|---|---|---|---|---|---|---|---|---|---|---|---|---|---|---|---|
| Cys | Asp | Thr | Arg | Gln | Gln | Tyr | Arg | Lys | Leu | Leu | Arg | Ser | Thr | Leu | Val |  |
|  |  |  | 985 |  |  |  |  | 990 |  |  |  | 995 |  |  |  |  |

| CTC | GTG | CCG | CTC | TTT | GGT | GTC | CAC | TAC | ACC | GTC | TTC | ATG | GCC | TTG | CCG | 1356 |
|---|---|---|---|---|---|---|---|---|---|---|---|---|---|---|---|---|
| Leu | Val | Pro | Leu | Phe | Gly | Val | His | Tyr | Thr | Val | Phe | Met | Ala | Leu | Pro |  |
|  |  | 1000 |  |  |  |  | 1005 |  |  |  |  | 1010 |  |  |  |  |

| TAC | ACC | GAG | GTC | TCA | GGG | ACA | TTG | TGG | CAG | ATC | CAG | ATG | CAT | TAT | GAG | 1404 |
|---|---|---|---|---|---|---|---|---|---|---|---|---|---|---|---|---|
| Tyr | Thr | Glu | Val | Ser | Gly | Thr | Leu | Trp | Gln | Ile | Gln | Met | His | Tyr | Glu |  |
| 1015 |  |  |  |  |  | 1020 |  |  |  |  | 1025 |  |  |  |  |  |

| ATG | CTC | TTC | AAC | TCC | TTC | CAG | GGA | TTT | TTT | GTT | GCC | ATC | ATA | TAC | TGT | 1452 |
|---|---|---|---|---|---|---|---|---|---|---|---|---|---|---|---|---|
| Met | Leu | Phe | Asn | Ser | Phe | Gln | Gly | Phe | Phe | Val | Ala | Ile | Ile | Tyr | Cys |  |
| 1030 |  |  |  |  | 1035 |  |  |  |  | 1040 |  |  |  |  | 1045 |  |

| TTC | TGC | AAT | GGT | GAG | GTG | CAG | GCA | GAG | ATT | AGG | AAG | TCA | TGG | AGC | CGC | 1500 |
|---|---|---|---|---|---|---|---|---|---|---|---|---|---|---|---|---|
| Phe | Cys | Asn | Gly | Glu | Val | Gln | Ala | Glu | Ile | Arg | Lys | Ser | Trp | Ser | Arg |  |
|  |  |  |  | 1050 |  |  |  |  | 1055 |  |  |  |  | 1060 |  |  |

| TGG | ACA | CTG | GCG | TTG | GAC | TTC | AAG | CGC | AAA | GCA | CGA | AGT | GGG | AGT | AGC | 1548 |
|---|---|---|---|---|---|---|---|---|---|---|---|---|---|---|---|---|
| Trp | Thr | Leu | Ala | Leu | Asp | Phe | Lys | Arg | Lys | Ala | Arg | Ser | Gly | Ser | Ser |  |
|  |  |  |  | 1065 |  |  |  |  | 1070 |  |  |  |  | 1075 |  |  |

| AGC | TAC | AGC | TAT | GGC | CCA | ATG | GTG | TCT | CAC | ACG | AGT | GTG | ACC | AAT | GTG | 1596 |
|---|---|---|---|---|---|---|---|---|---|---|---|---|---|---|---|---|
| Ser | Tyr | Ser | Tyr | Gly | Pro | Met | Val | Ser | His | Thr | Ser | Val | Thr | Asn | Val |  |
|  |  |  | 1080 |  |  |  |  | 1085 |  |  |  |  | 1090 |  |  |  |

| GGC | CCC | CGT | GCA | GGA | CTC | AGC | CTC | CCC | CTC | AGC | CCC | CGC | CTG | CCT | CCT | 1644 |
|---|---|---|---|---|---|---|---|---|---|---|---|---|---|---|---|---|
| Gly | Pro | Arg | Ala | Gly | Leu | Ser | Leu | Pro | Leu | Ser | Pro | Arg | Leu | Pro | Pro |  |
|  |  | 1095 |  |  |  |  | 1100 |  |  |  |  | 1105 |  |  |  |  |

| GCC | ACT | ACC | AAT | GGC | CAC | TCC | CAG | CTG | CCT | GGC | CAT | GCC | AAG | CCA | GGG | 1692 |
|---|---|---|---|---|---|---|---|---|---|---|---|---|---|---|---|---|
| Ala | Thr | Thr | Asn | Gly | His | Ser | Gln | Leu | Pro | Gly | His | Ala | Lys | Pro | Gly |  |
| 1110 |  |  |  |  | 1115 |  |  |  |  | 1120 |  |  |  |  | 1125 |  |

| GCT | CCA | GCC | ACT | GAG | ACT | GAA | ACC | CTA | CCA | GTC | ACT | ATG | GCG | GTT | CCC | 1740 |
|---|---|---|---|---|---|---|---|---|---|---|---|---|---|---|---|---|
| Ala | Pro | Ala | Thr | Glu | Thr | Glu | Thr | Leu | Pro | Val | Thr | Met | Ala | Val | Pro |  |
|  |  |  |  | 1130 |  |  |  |  | 1135 |  |  |  |  | 1140 |  |  |

| AAG | GAC | GAT | GGA | TTC | CTT | AAC | GGC | TCC | TGC | TCA | GGC | CTG | GAT | GAG | GAG | 1788 |
|---|---|---|---|---|---|---|---|---|---|---|---|---|---|---|---|---|
| Lys | Asp | Asp | Gly | Phe | Leu | Asn | Gly | Ser | Cys | Ser | Gly | Leu | Asp | Glu | Glu |  |
|  |  |  |  | 1145 |  |  |  |  | 1150 |  |  |  |  | 1155 |  |  |

| GCC | TCC | GGG | TCT | GCG | CGG | CCG | CCT | CCA | TTG | TTG | CAG | GAA | GGA | TGG | GAA | 1836 |
|---|---|---|---|---|---|---|---|---|---|---|---|---|---|---|---|---|
| Ala | Ser | Gly | Ser | Ala | Arg | Pro | Pro | Pro | Leu | Leu | Gln | Glu | Gly | Trp | Glu |  |
|  |  |  | 1160 |  |  |  |  | 1165 |  |  |  |  | 1170 |  |  |  |

| ACA | GTC | ATG | T | GACTGGGCAC | TAGGGGCTA | GACTGCTGGC | CTGGGCACAT | 1886 |
|---|---|---|---|---|---|---|---|---|
| Thr | Val | Met |  |  |  |  |  |  |
|  | 1175 |  |  |  |  |  |  |  |

| GGACAGATGG | ACCAAGAAGC | CAGTGTTTGG | CTGGTTGTCT | ATTCGGGATC | TGGACCAGGA | 1946 |
|---|---|---|---|---|---|---|
| AGATAACAAA | AGGAAAATGG | AAGTGGACGA | AGCAGAGAAG | AAGGAAGAGG | TTTTGCAGGA | 2006 |
| ATTAAATATG | TTTCCTCAGT | TGGATGATGA | GGACACAAGG | AAGGC |  | 2051 |

( 2 ) INFORMATION FOR SEQ ID NO:4:

( i ) SEQUENCE CHARACTERISTICS:
        ( A ) LENGTH: 2010 base pairs
        ( B ) TYPE: nucleic acid
        ( C ) STRANDEDNESS: single
        ( D ) TOPOLOGY: linear ( i x ) FEATURE:
        ( A ) NAME/KEY: CDS

5,886,148

39

40

-continued ( B ) LOCATION: 28..1807

( x i ) SEQUENCE DESCRIPTION: SEQ ID NO:4:

```
GGGATCCCGC GGCCCTAGGC GGTGGCG ATG GGG ACC GCC CGG ATC GCA CCC        51
                                Met Gly Thr Ala Arg Ile Ala Pro
                                                            595

GGC CTG GCG CTC CTG CTC TGC TGC CCC GTG CTC AGC TCC GCG TAC GCG      99
Gly Leu Ala Leu Leu Leu Cys Cys Pro Val Leu Ser Ser Ala Tyr Ala
600                 605                 610                 615

CTG GTG GAT GCA GAT GAC GTC ATG ACT AAA GAG GAA CAG ATC TTC CTG     147
Leu Val Asp Ala Asp Asp Val Met Thr Lys Glu Glu Gln Ile Phe Leu
                620                 625                 630

CTG CAC CGT GCT CAG GCC CAG TGC GAA AAA CGG CTC AAG GAG GTC CTG     195
Leu His Arg Ala Gln Ala Gln Cys Glu Lys Arg Leu Lys Glu Val Leu
            635                 640                 645

CAG AGG CCA GCC AGC ATA ATG GAA TCA GAC AAG GGA TGG ACA TCT GCG     243
Gln Arg Pro Ala Ser Ile Met Glu Ser Asp Lys Gly Trp Thr Ser Ala
        650                 655                 660

TCC ACA TCA GGG AAG CCC AGG AAA GAT AAG GCA TCT GGG AAG CTC TAC     291
Ser Thr Ser Gly Lys Pro Arg Lys Asp Lys Ala Ser Gly Lys Leu Tyr
    665                 670                 675

CCT GAG TCT GAG GAG GAC AAG GAG GCA CCC ACT GGC AGC AGG TAC CGA     339
Pro Glu Ser Glu Glu Asp Lys Glu Ala Pro Thr Gly Ser Arg Tyr Arg
680                 685                 690                 695

GGG CGC CCC TGT CTG CCG GAA TGG GAC CAC ATC CTG TGC TGG CCG CTG     387
Gly Arg Pro Cys Leu Pro Glu Trp Asp His Ile Leu Cys Trp Pro Leu
                700                 705                 710

GGG GCA CCA GGT GAG GTG GTG GCT GTG CCC TGT CCG GAC TAC ATT TAT     435
Gly Ala Pro Gly Glu Val Val Ala Val Pro Cys Pro Asp Tyr Ile Tyr
            715                 720                 725

GAC TTC AAT CAC AAA GGC CAT GCC TAC CGA CGC TGT GAC CGC AAT GGC     483
Asp Phe Asn His Lys Gly His Ala Tyr Arg Arg Cys Asp Arg Asn Gly
        730                 735                 740

AGC TGG GAG CTG GTG CCT GGG CAC AAC AGG ACG TGG GCC AAC TAC AGC     531
Ser Trp Glu Leu Val Pro Gly His Asn Arg Thr Trp Ala Asn Tyr Ser
    745                 750                 755

GAG TGT GTC AAA TTT CTC ACC AAT GAG ACT CGT GAA CGG GAG GTG TTT     579
Glu Cys Val Lys Phe Leu Thr Asn Glu Thr Arg Glu Arg Glu Val Phe
760                 765                 770                 775

GAC CGC CTG GGC ATG ATT TAC ACC GTG GGC TAC TCC GTG TCC CTG GCG     627
Asp Arg Leu Gly Met Ile Tyr Thr Val Gly Tyr Ser Val Ser Leu Ala
                780                 785                 790

TCC CTC ACC GTA GCT GTG CTC ATC CTG GCC TAC TTT AGG CGG CTG CAC     675
Ser Leu Thr Val Ala Val Leu Ile Leu Ala Tyr Phe Arg Arg Leu His
            795                 800                 805

TGC ACG CGC AAC TAC ATC CAC ATG CAC CTG TTC CTG TCC TTC ATG CTG     723
Cys Thr Arg Asn Tyr Ile His Met His Leu Phe Leu Ser Phe Met Leu
        810                 815                 820

CGC GCC GTG AGC ATC TTC GTC AAG GAC GCT GTG CTC TAC TCT GGC GCC     771
Arg Ala Val Ser Ile Phe Val Lys Asp Ala Val Leu Tyr Ser Gly Ala
    825                 830                 835

ACG CTT GAT GAG GCT GAG CGC CTC ACC GAG GAG GAG CTG CGC GCC ATC     819
Thr Leu Asp Glu Ala Glu Arg Leu Thr Glu Glu Glu Leu Arg Ala Ile
840                 845                 850                 855

GCC CAG GCG CCC CCG CCG CCT GCC ACC GCC GCT GCC GGC TAC GCG GGC     867
Ala Gln Ala Pro Pro Pro Pro Ala Thr Ala Ala Ala Gly Tyr Ala Gly
                860                 865                 870

TGC AGG GTG GCT GTG ACC TTC TTC CTT TAC TTC CTG GCC ACC AAC TAC     915
Cys Arg Val Ala Val Thr Phe Phe Leu Tyr Phe Leu Ala Thr Asn Tyr
            875                 880                 885
```

| | | | | | | | | | | | | | | | | |
|---|---|---|---|---|---|---|---|---|---|---|---|---|---|---|---|---|
| TAC | TGG | ATT | CTG | GTG | GAG | GGG | CTG | TAC | CTG | CAC | AGC | CTC | ATC | TTC | ATG | 963 |
| Tyr | Trp | Ile | Leu | Val | Glu | Gly | Leu | Tyr | Leu | His | Ser | Leu | Ile | Phe | Met | |
| | | 890 | | | | | 895 | | | | 900 | | | | | |
| GCC | TTC | TTC | TCA | GAG | AAG | AAG | TAC | CTG | TGG | GGC | TTC | ACA | GTC | TTC | GGC | 1011 |
| Ala | Phe | Phe | Ser | Glu | Lys | Lys | Tyr | Leu | Trp | Gly | Phe | Thr | Val | Phe | Gly | |
| 905 | | | | | 910 | | | | | 915 | | | | | | |
| TGG | GGT | CTG | CCC | GCT | GTC | TTC | GTG | GCT | GTG | TGG | GTC | AGT | GTC | AGA | GCT | 1059 |
| Trp | Gly | Leu | Pro | Ala | Val | Phe | Val | Ala | Val | Trp | Val | Ser | Val | Arg | Ala | |
| 920 | | | | | 925 | | | | | 930 | | | | | 935 | |
| ACC | CTG | GCC | AAC | ACC | GGG | TGC | TGG | GAC | TTG | AGC | TCC | GGG | AAC | AAA | AAG | 1107 |
| Thr | Leu | Ala | Asn | Thr | Gly | Cys | Trp | Asp | Leu | Ser | Ser | Gly | Asn | Lys | Lys | |
| | | | | 940 | | | | | 945 | | | | | 950 | | |
| TGG | ATC | ATC | CAG | GTG | CCC | ATC | CTG | GCC | TCC | ATT | GTG | CTC | AAC | TTC | ATC | 1155 |
| Trp | Ile | Ile | Gln | Val | Pro | Ile | Leu | Ala | Ser | Ile | Val | Leu | Asn | Phe | Ile | |
| | | | 955 | | | | | 960 | | | | | 965 | | | |
| CTC | TTC | ATC | AAT | ATC | GTC | CGG | GTG | CTC | GCC | ACC | AAG | CAG | CGG | GAG | ACC | 1203 |
| Leu | Phe | Ile | Asn | Ile | Val | Arg | Val | Leu | Ala | Thr | Lys | Gln | Arg | Glu | Thr | |
| | | 970 | | | | | 975 | | | | | 980 | | | | |
| AAC | GCC | GGC | CGG | TGT | GAC | ACA | CGG | CAG | CAG | TAC | CGG | AAG | CTG | CTC | AAA | 1251 |
| Asn | Ala | Gly | Arg | Cys | Asp | Thr | Arg | Gln | Gln | Tyr | Arg | Lys | Leu | Leu | Lys | |
| | 985 | | | | | 990 | | | | | 995 | | | | | |
| TCC | ACG | CTG | GTG | CTC | ATG | CCC | CTC | TTT | GGC | GTC | CAC | TAC | ATT | GTC | TTC | 1299 |
| Ser | Thr | Leu | Val | Leu | Met | Pro | Leu | Phe | Gly | Val | His | Tyr | Ile | Val | Phe | |
| 1000 | | | | | 1005 | | | | | 1010 | | | | | 1015 | |
| ATG | GCC | ACA | CCA | TAC | ACC | GAG | GTC | TCA | GGG | ACG | CTC | TGG | CAA | GTC | CAG | 1347 |
| Met | Ala | Thr | Pro | Tyr | Thr | Glu | Val | Ser | Gly | Thr | Leu | Trp | Gln | Val | Gln | |
| | | | | 1020 | | | | | 1025 | | | | | 1030 | | |
| ATG | CAC | TAT | GAG | ATG | CTC | TTC | AAC | TCC | TTC | CAG | GGA | TTT | TTT | GTC | GCA | 1395 |
| Met | His | Tyr | Glu | Met | Leu | Phe | Asn | Ser | Phe | Gln | Gly | Phe | Phe | Val | Ala | |
| | | | | 1035 | | | | | 1040 | | | | | 1045 | | |
| ATC | ATA | TAC | TGT | TTC | TGC | AAT | GGC | GAG | GTA | CAA | GCT | GAG | ATC | AAG | AAA | 1443 |
| Ile | Ile | Tyr | Cys | Phe | Cys | Asn | Gly | Glu | Val | Gln | Ala | Glu | Ile | Lys | Lys | |
| | | | 1050 | | | | | 1055 | | | | | 1060 | | | |
| TCT | TGG | AGC | CGC | TGG | ACA | CTG | GCA | CTG | GAC | TTC | AAG | CGA | AAG | GCA | CGC | 1491 |
| Ser | Trp | Ser | Arg | Trp | Thr | Leu | Ala | Leu | Asp | Phe | Lys | Arg | Lys | Ala | Arg | |
| | 1065 | | | | | 1070 | | | | | 1075 | | | | | |
| AGC | GGG | AGC | AGC | AGC | TAT | AGC | TAC | GGC | CCC | ATG | GTG | TCC | CAC | ACA | AGT | 1539 |
| Ser | Gly | Ser | Ser | Ser | Tyr | Ser | Tyr | Gly | Pro | Met | Val | Ser | His | Thr | Ser | |
| 1080 | | | | | 1085 | | | | | 1090 | | | | | 1095 | |
| GTG | ACC | AAT | GTC | GGC | CCC | CGT | GTG | GGA | CTC | GGC | CTG | CCC | CTC | AGC | CCC | 1587 |
| Val | Thr | Asn | Val | Gly | Pro | Arg | Val | Gly | Leu | Gly | Leu | Pro | Leu | Ser | Pro | |
| | | | | 1100 | | | | | 1105 | | | | | 1110 | | |
| CGC | CTA | CTG | CCC | ACT | GCC | ACC | ACC | AAC | GGC | CAC | CCT | CAG | CTG | CCT | GGC | 1635 |
| Arg | Leu | Leu | Pro | Thr | Ala | Thr | Thr | Asn | Gly | His | Pro | Gln | Leu | Pro | Gly | |
| | | | 1115 | | | | | 1120 | | | | | 1125 | | | |
| CAT | GCC | AAG | CCA | GGG | ACC | CCA | GCC | CTG | GAG | ACC | CTG | GAG | ACC | ACA | CCA | 1683 |
| His | Ala | Lys | Pro | Gly | Thr | Pro | Ala | Leu | Glu | Thr | Leu | Glu | Thr | Thr | Pro | |
| | | 1130 | | | | | 1135 | | | | | 1140 | | | | |
| CCT | GCC | ATG | GCT | GCT | CCC | AAG | GAC | GAT | GGG | TTC | CTC | AAC | GGC | TCC | TGC | 1731 |
| Pro | Ala | Met | Ala | Ala | Pro | Lys | Asp | Asp | Gly | Phe | Leu | Asn | Gly | Ser | Cys | |
| | | 1145 | | | | | 1150 | | | | | 1155 | | | | |
| TCA | GGC | CTG | GAC | GAG | GAG | GCC | TCT | GGG | CCT | GAG | CGG | CCA | CCT | GCC | CTG | 1779 |
| Ser | Gly | Leu | Asp | Glu | Glu | Ala | Ser | Gly | Pro | Glu | Arg | Pro | Pro | Ala | Leu | |
| 1160 | | | | | 1165 | | | | | 1170 | | | | | 1175 | |
| CTA | CAG | GAA | GAG | TGG | GAG | ACA | GTC | ATG | T GACCAGGCGC TGGGGGCTGG | | | | | | | 1827 |
| Leu | Gln | Glu | Glu | Trp | Glu | Thr | Val | Met | | | | | | | | |
| | | | | 1180 | | | | | | | | | | | | |

ACCTGCTGAC ATAGTGGATG GACAGATGGA CCAAAAGATG GGTGGTTGAA TGATTTCCCA 1887

CTCAGGGCCT GGGGCCAAGA GGAAAAAACA GGGGAAAAAA GAAAAAAAAA AGAAAAAAGG 1947

```
AAAAAAAAA AAAAAAAAA AAAAAAAAA AAAAAAAAA AAAAAAAAA AAAAAAAAA    2007

AAA                                                             2010
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:5:

```
Thr Asn Glu Thr Arg Glu Arg Glu Val Phe Asp Arg Leu Gly Met Ile
1               5                   10                  15
Tyr Thr Val Gly
            20
```

( 2 ) INFORMATION FOR SEQ ID NO:6:

( i ) SEQUENCE CHARACTERISTICS:
        ( A ) LENGTH: 19 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:6:

```
Tyr Leu Tyr Ser Gly Phe Thr Leu Asp Glu Ala Glu Arg Leu Thr Glu
1               5                   10                  15
Glu Glu Leu
```

( 2 ) INFORMATION FOR SEQ ID NO:7:

( i ) SEQUENCE CHARACTERISTICS:
        ( A ) LENGTH: 19 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:7:

```
Val Thr Phe Phe Leu Tyr Phe Leu Ala Thr Asn Tyr Tyr Trp Ile Leu
1               5                   10                  15
Val Glu Gly
```

( 2 ) INFORMATION FOR SEQ ID NO:8:

( i ) SEQUENCE CHARACTERISTICS:
        ( A ) LENGTH: 26 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:8:

```
Tyr Xaa Arg Ala Thr Leu Ala Asn Thr Gly Cys Trp Asp Leu Ser Ser
1               5                   10                  15
Gly His Lys Lys Trp Ile Ile Gln Val Pro
            20                  25
```

( 2 ) INFORMATION FOR SEQ ID NO:9:

( i ) SEQUENCE CHARACTERISTICS:
: ( A ) LENGTH: 18 amino acids
: ( B ) TYPE: amino acid
: ( C ) STRANDEDNESS: Not Relevant
: ( D ) TOPOLOGY: linear ( i i ) MOLECULE TYPE: peptide ( x i ) SEQUENCE DESCRIPTION: SEQ ID NO:9:

```
Pro Tyr Thr Glu Tyr Ser Gly Thr Leu Trp Gln Ile Gln Met His Tyr
1               5                   10                  15
Glu Met
```

( 2 ) INFORMATION FOR SEQ ID NO:10:

( i ) SEQUENCE CHARACTERISTICS:
: ( A ) LENGTH: 18 amino acids
: ( B ) TYPE: amino acid
: ( C ) STRANDEDNESS: Not Relevant
: ( D ) TOPOLOGY: linear ( i i ) MOLECULE TYPE: peptide ( x i ) SEQUENCE DESCRIPTION: SEQ ID NO:10:

```
Asp Asp Val Phe Thr Lys Glu Glu Gln Ile Phe Leu Leu His Arg Ala
1               5                   10                  15
Gln Ala
```

( 2 ) INFORMATION FOR SEQ ID NO:11:

( i ) SEQUENCE CHARACTERISTICS:
: ( A ) LENGTH: 10 amino acids
: ( B ) TYPE: amino acid
: ( C ) STRANDEDNESS: Not Relevant
: ( D ) TOPOLOGY: linear ( i i ) MOLECULE TYPE: peptide ( x i ) SEQUENCE DESCRIPTION: SEQ ID NO:11:

```
Phe Phe Arg Leu His Cys Thr Arg Asn Tyr
1               5                   10
```

( 2 ) INFORMATION FOR SEQ ID NO:12:

( i ) SEQUENCE CHARACTERISTICS:
: ( A ) LENGTH: 10 amino acids
: ( B ) TYPE: amino acid
: ( C ) STRANDEDNESS: Not Relevant
: ( D ) TOPOLOGY: linear ( i i ) MOLECULE TYPE: peptide ( x i ) SEQUENCE DESCRIPTION: SEQ ID NO:12:

```
Glu Lys Lys Tyr Leu Trp Gly Phe Thr Leu
1               5                   10
```

( 2 ) INFORMATION FOR SEQ ID NO:13:

( i ) SEQUENCE CHARACTERISTICS:
: ( A ) LENGTH: 25 amino acids
: ( B ) TYPE: amino acid
: ( C ) STRANDEDNESS: Not Relevant
: ( D ) TOPOLOGY: linear ( i i ) MOLECULE TYPE: peptide ( x i ) SEQUENCE DESCRIPTION: SEQ ID NO:13:

```
Val Leu Ala Thr Lys Leu Arg Glu Thr Asn Ala Gly Arg Cys Asp Thr
```

|       | 1                 | 5             | 10              | 15          |
|-------|-------------------|---------------|-----------------|-------------|
|       | Arg Gln Gln Tyr Arg Lys Leu Leu Lys |   |   |   |
|       |                   | 20            | 25              |             |

( 2 ) INFORMATION FOR SEQ ID NO:14:

( i ) SEQUENCE CHARACTERISTICS:
    ( A ) LENGTH: 18 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:14:

AGATGAGGCT GTGCAGGT             18

( 2 ) INFORMATION FOR SEQ ID NO:15:

( i ) SEQUENCE CHARACTERISTICS:
    ( A ) LENGTH: 25 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:15:

GGAATTCCAT GGGAGCGGCC CGGAT             25

( 2 ) INFORMATION FOR SEQ ID NO:16:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:16:

CGGGATCCCG CGGCCCTAGG CGGT             24

( 2 ) INFORMATION FOR SEQ ID NO:17:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:17:

AGTATAGCGT CCTTGACGA             19

( 2 ) INFORMATION FOR SEQ ID NO:18:

( i ) SEQUENCE CHARACTERISTICS:
    ( A ) LENGTH: 515 amino acids
    ( B ) TYPE: amino acid
    ( D ) TOPOLOGY: linear ( i i ) MOLECULE TYPE: protein ( x i ) SEQUENCE DESCRIPTION: SEQ ID NO:18:

Met Gly Ala Pro Arg Ile Ser His Ser Leu Ala Leu Leu Cys Cys
 1               5                  10                  15

Ser Val Leu Ser Ser Val Tyr Ala Leu Val Asp Ala Asp Val Ile
                20                  25                  30

Thr Lys Glu Glu Gln Ile Ile Leu Leu Arg Asn Ala Gln Ala Gln Cys
            35                  40                  45

Glu Gln Arg Leu Lys Glu Val Leu Arg Val Pro Glu Leu Ala Glu Ser
        50                  55                  60

-continued

| | | | | | | | | | | | | | | | |
|---|---|---|---|---|---|---|---|---|---|---|---|---|---|---|---|
| Ala | Lys | Asp | Trp | Met | Ser | Arg | Ser | Ala | Lys | Thr | Lys | Lys | Glu | Lys | Pro |
| 65 | | | | | 70 | | | | | 75 | | | | | 80 |
| Ala | Glu | Lys | Leu | Tyr | Pro | Gln | Ala | Glu | Glu | Ser | Arg | Glu | Val | Ser | Asp |
| | | | | 85 | | | | | 90 | | | | | 95 | |
| Arg | Ser | Arg | Leu | Gln | Asp | Gly | Phe | Cys | Leu | Pro | Glu | Trp | Asp | Asn | Ile |
| | | | | 100 | | | | | 105 | | | | | 110 | |
| Val | Cys | Trp | Pro | Ala | Gly | Val | Pro | Gly | Lys | Val | Val | Ala | Val | Pro | Cys |
| | | 115 | | | | | 120 | | | | | 125 | | | |
| Pro | Asp | Tyr | Phe | Tyr | Asp | Phe | Asn | His | Lys | Gly | Arg | Ala | Tyr | Arg | Arg |
| | 130 | | | | | 135 | | | | | 140 | | | | |
| Cys | Asp | Ser | Asn | Gly | Ser | Trp | Glu | Leu | Val | Pro | Gly | Asn | Asn | Arg | Thr |
| 145 | | | | | 150 | | | | | 155 | | | | | 160 |
| Trp | Ala | Asn | Tyr | Ser | Glu | Cys | Val | Lys | Phe | Leu | Thr | Asn | Glu | Thr | Arg |
| | | | | 165 | | | | | 170 | | | | | 175 | |
| Glu | Arg | Glu | Val | Phe | Asp | Arg | Leu | Gly | Met | Ile | Tyr | Thr | Val | Gly | Tyr |
| | | | | 180 | | | | | 185 | | | | | 190 | |
| Ser | Ile | Ser | Leu | Gly | Ser | Leu | Thr | Val | Ala | Val | Leu | Ile | Leu | Gly | Tyr |
| | | | | 195 | | | | | 200 | | | | | 205 | |
| Phe | Arg | Arg | Leu | His | Cys | Thr | Arg | Asn | Tyr | Ile | His | Met | His | Leu | Phe |
| | 210 | | | | | 215 | | | | | 220 | | | | |
| Val | Ser | Phe | Met | Leu | Arg | Ala | Val | Ser | Ile | Phe | Ile | Lys | Asp | Ala | Val |
| 225 | | | | | 230 | | | | | 235 | | | | | 240 |
| Leu | Tyr | Ser | Gly | Val | Ser | Thr | Asp | Glu | Ile | Glu | Arg | Ile | Thr | Glu | Glu |
| | | | | 245 | | | | | 250 | | | | | 255 | |
| Glu | Leu | Arg | Ala | Phe | Thr | Glu | Pro | Pro | Ala | Asp | Lys | Ala | Gly | Phe |
| | | | 260 | | | | | 265 | | | | | 270 | | |
| Val | Gly | Cys | Arg | Val | Ala | Val | Thr | Val | Phe | Leu | Tyr | Phe | Leu | Thr | Thr |
| | | 275 | | | | | 280 | | | | | 285 | | | |
| Asn | Tyr | Tyr | Trp | Ile | Leu | Val | Glu | Gly | Leu | Tyr | Leu | His | Ser | Leu | Ile |
| | | 290 | | | | | 295 | | | | | 300 | | | |
| Phe | Met | Ala | Phe | Phe | Ser | Glu | Lys | Lys | Tyr | Leu | Trp | Gly | Phe | Thr | Leu |
| 305 | | | | | 310 | | | | | 315 | | | | | 320 |
| Phe | Gly | Trp | Gly | Leu | Pro | Ala | Val | Phe | Val | Ala | Val | Trp | Val | Thr | Val |
| | | | | 325 | | | | | 330 | | | | | 335 | |
| Arg | Ala | Thr | Leu | Ala | Asn | Thr | Glu | Cys | Trp | Asp | Leu | Ser | Ser | Gly | Asn |
| | | | 340 | | | | | 345 | | | | | 350 | | |
| Lys | Lys | Trp | Ile | Ile | Gln | Val | Pro | Ile | Leu | Ala | Ala | Ile | Val | Val | Asn |
| | | 355 | | | | | 360 | | | | | 365 | | | |
| Phe | Ile | Leu | Phe | Ile | Asn | Ile | Ile | Arg | Val | Leu | Ala | Thr | Lys | Leu | Arg |
| | 370 | | | | | 375 | | | | | 380 | | | | |
| Glu | Thr | Asn | Ala | Gly | Arg | Cys | Asp | Thr | Arg | Gln | Gln | Tyr | Arg | Lys | Leu |
| 385 | | | | | 390 | | | | | 395 | | | | | 400 |
| Leu | Lys | Ser | Thr | Leu | Val | Leu | Met | Pro | Leu | Phe | Gly | Val | His | Tyr | Ile |
| | | | | 405 | | | | | 410 | | | | | 415 | |
| Val | Phe | Met | Ala | Thr | Pro | Tyr | Thr | Glu | Val | Ser | Gly | Ile | Leu | Trp | Gln |
| | | | 420 | | | | | 425 | | | | | 430 | | |
| Val | Gln | Met | His | Tyr | Glu | Met | Leu | Phe | Asn | Ser | Phe | Gln | Gly | Phe | Phe |
| | | | 435 | | | | 440 | | | | | 445 | | | |
| Val | Ala | Ile | Ile | Tyr | Cys | Phe | Cys | Asn | Gly | Glu | Val | Gln | Ala | Glu | Ile |
| | 450 | | | | | 455 | | | | | 460 | | | | |
| Lys | Lys | Ser | Trp | Ser | Arg | Trp | Thr | Leu | Ala | Leu | Asp | Phe | Lys | Arg | Lys |
| 465 | | | | | 470 | | | | | 475 | | | | | 480 |
| Ala | Arg | Ser | Gly | Ser | Ser | Thr | Tyr | Ser | Tyr | Gly | Pro | Met | Val | Ser | His |

|  |  |  |  |  |  |  |  |  |  |  |  |  |  |  |
|---|---|---|---|---|---|---|---|---|---|---|---|---|---|---|
|  |  |  | 485 |  |  |  |  | 490 |  |  |  |  | 495 |  |
| Thr | Ser | Val | Thr | Asn | Val | Gly | Pro | Arg | Gly | Gly | Trp | Pro | Cys | Pro | Ser |
|  |  |  | 500 |  |  |  |  | 505 |  |  |  |  | 510 |  |  |
| Ala | Leu | Asp |  |  |  |  |  |  |  |  |  |  |  |  |  |
|  |  | 515 |  |  |  |  |  |  |  |  |  |  |  |  |  |

( 2 ) INFORMATION FOR SEQ ID NO:19:

( i ) SEQUENCE CHARACTERISTICS:
        ( A ) LENGTH: 585 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| Met | Gly | Ala | Pro | Arg | Ile | Ser | His | Ser | Leu | Ala | Leu | Leu | Leu | Cys | Cys |
|---|---|---|---|---|---|---|---|---|---|---|---|---|---|---|---|
| 1 |  |  |  | 5 |  |  |  |  | 10 |  |  |  |  | 15 |  |
| Ser | Val | Leu | Ser | Ser | Val | Tyr | Ala | Leu | Val | Asp | Ala | Asp | Val | Ile |  |
|  |  |  | 20 |  |  |  |  | 25 |  |  |  |  | 30 |  |  |
| Thr | Lys | Glu | Glu | Gln | Ile | Ile | Leu | Leu | Arg | Asn | Ala | Gln | Ala | Gln | Cys |
|  |  |  | 35 |  |  |  |  | 40 |  |  |  |  | 45 |  |  |
| Glu | Gln | Arg | Leu | Lys | Glu | Val | Leu | Arg | Val | Pro | Glu | Leu | Ala | Glu | Ser |
|  |  | 50 |  |  |  |  | 55 |  |  |  |  | 60 |  |  |  |
| Ala | Lys | Asp | Trp | Met | Ser | Arg | Ser | Ala | Lys | Thr | Lys | Lys | Glu | Lys | Pro |
| 65 |  |  |  |  | 70 |  |  |  |  | 75 |  |  |  |  | 80 |
| Ala | Glu | Lys | Leu | Tyr | Pro | Gln | Ala | Glu | Glu | Ser | Arg | Glu | Val | Ser | Asp |
|  |  |  |  | 85 |  |  |  |  | 90 |  |  |  |  | 95 |  |
| Arg | Ser | Arg | Leu | Gln | Asp | Gly | Phe | Cys | Leu | Pro | Glu | Trp | Asp | Asn | Ile |
|  |  |  | 100 |  |  |  |  | 105 |  |  |  |  | 110 |  |  |
| Val | Cys | Trp | Pro | Ala | Gly | Val | Pro | Gly | Lys | Val | Val | Ala | Val | Pro | Cys |
|  |  |  | 115 |  |  |  |  | 120 |  |  |  |  | 125 |  |  |
| Pro | Asp | Tyr | Phe | Tyr | Asp | Phe | Asn | His | Lys | Gly | Arg | Ala | Tyr | Arg | Arg |
|  |  | 130 |  |  |  |  | 135 |  |  |  |  | 140 |  |  |  |
| Cys | Asp | Ser | Asn | Gly | Ser | Trp | Glu | Leu | Val | Pro | Gly | Asn | Asn | Arg | Thr |
| 145 |  |  |  |  | 150 |  |  |  |  | 155 |  |  |  |  | 160 |
| Trp | Ala | Asn | Tyr | Ser | Glu | Cys | Val | Lys | Phe | Leu | Thr | Asn | Glu | Thr | Arg |
|  |  |  |  | 165 |  |  |  |  | 170 |  |  |  |  | 175 |  |
| Glu | Arg | Glu | Val | Phe | Asp | Arg | Leu | Gly | Met | Ile | Tyr | Thr | Val | Gly | Tyr |
|  |  |  | 180 |  |  |  |  | 185 |  |  |  |  | 190 |  |  |
| Ser | Ile | Ser | Leu | Gly | Ser | Leu | Thr | Val | Ala | Val | Leu | Ile | Leu | Gly | Tyr |
|  |  |  | 195 |  |  |  |  | 200 |  |  |  |  | 205 |  |  |
| Phe | Arg | Arg | Leu | His | Cys | Thr | Arg | Asn | Tyr | Ile | His | Met | His | Leu | Phe |
|  |  | 210 |  |  |  |  | 215 |  |  |  |  | 220 |  |  |  |
| Val | Ser | Phe | Met | Leu | Arg | Ala | Val | Ser | Ile | Phe | Ile | Lys | Asp | Ala | Val |
| 225 |  |  |  |  | 230 |  |  |  |  | 235 |  |  |  |  | 240 |
| Leu | Tyr | Ser | Gly | Val | Ser | Thr | Asp | Glu | Ile | Glu | Arg | Ile | Thr | Glu | Glu |
|  |  |  |  | 245 |  |  |  |  | 250 |  |  |  |  | 255 |  |
| Glu | Leu | Arg | Ala | Phe | Thr | Glu | Pro | Pro | Pro | Ala | Asp | Lys | Ala | Gly | Phe |
|  |  |  | 260 |  |  |  |  | 265 |  |  |  |  | 270 |  |  |
| Val | Gly | Cys | Arg | Val | Ala | Val | Thr | Val | Phe | Leu | Tyr | Phe | Leu | Thr | Thr |
|  |  | 275 |  |  |  |  | 280 |  |  |  |  | 285 |  |  |  |
| Asn | Tyr | Tyr | Trp | Ile | Leu | Val | Glu | Gly | Leu | Tyr | Leu | His | Ser | Leu | Ile |
|  |  | 290 |  |  |  |  | 295 |  |  |  |  | 300 |  |  |  |
| Phe | Met | Ala | Phe | Phe | Ser | Glu | Lys | Lys | Tyr | Leu | Trp | Gly | Phe | Thr | Leu |
| 305 |  |  |  |  | 310 |  |  |  |  | 315 |  |  |  |  | 320 |

Phe Gly Trp Gly Leu Pro Ala Val Phe Val Ala Val Trp Val Thr Val
              325             330              335

Arg Ala Thr Leu Ala Asn Thr Glu Cys Trp Asp Leu Ser Ser Gly Asn
              340             345              350

Lys Lys Trp Ile Ile Gln Val Pro Ile Leu Ala Ala Ile Val Val Asn
              355             360              365

Phe Ile Leu Phe Ile Asn Ile Ile Arg Val Leu Ala Thr Lys Leu Arg
370             375              380

Glu Thr Asn Ala Gly Arg Cys Asp Thr Arg Gln Gln Tyr Arg Lys Leu
385             390              395              400

Leu Lys Ser Thr Leu Val Leu Met Pro Leu Phe Gly Val His Tyr Ile
              405             410              415

Val Phe Met Ala Thr Pro Tyr Thr Glu Val Ser Gly Ile Leu Trp Gln
              420             425              430

Val Gln Met His Tyr Glu Met Leu Phe Asn Ser Phe Gln Gly Phe Phe
              435             440              445

Val Ala Ile Ile Tyr Cys Phe Cys Asn Gly Glu Val Gln Ala Glu Ile
              450             455              460

Lys Lys Ser Trp Ser Arg Trp Thr Leu Ala Leu Asp Phe Lys Arg Lys
465             470              475              480

Ala Arg Ser Gly Ser Ser Thr Tyr Ser Tyr Gly Pro Met Val Ser His
              485             490              495

Thr Ser Val Thr Asn Val Gly Pro Arg Gly Gly Leu Ala Leu Ser Leu
              500             505              510

Ser Pro Arg Leu Ala Pro Gly Ala Gly Ala Ser Ala Asn Gly His His
              515             520              525

Gln Leu Pro Gly Tyr Val Lys His Gly Ser Ile Ser Glu Asn Ser Leu
              530             535              540

Pro Ser Ser Gly Pro Glu Pro Gly Thr Lys Asp Asp Gly Tyr Leu Asn
545             550              555              560

Gly Ser Gly Leu Tyr Glu Pro Met Val Gly Glu Gln Pro Pro Pro Leu
              565             570              575

Leu Glu Glu Glu Arg Glu Thr Val Met
              580             585

( 2 ) INFORMATION FOR SEQ ID NO:20:

( i ) SEQUENCE CHARACTERISTICS:
        ( A ) LENGTH: 591 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

Met Gly Ala Ala Arg Ile Ala Pro Ser Leu Ala Leu Leu Leu Cys Cys
1               5                10               15

Pro Val Leu Ser Ser Ala Tyr Ala Leu Val Asp Ala Asp Asp Val Phe
              20              25               30

Thr Lys Glu Glu Gln Ile Phe Leu Leu His Arg Ala Gln Ala Gln Cys
              35              40               45

Asp Lys Leu Leu Lys Glu Val Leu His Thr Ala Ala Asn Ile Met Glu
              50              55               60

Ser Asp Lys Gly Trp Thr Pro Ala Ser Thr Ser Gly Lys Pro Arg Lys
65              70              75               80

Glu Lys Ala Ser Gly Lys Phe Tyr Pro Glu Ser Lys Glu Asn Lys Asp
              85              90               95

```
Val Pro Thr Gly Ser Arg Arg Arg Gly Arg Pro Cys Leu Pro Glu Trp
                100                 105                 110

Asp Asn Ile Val Cys Trp Pro Leu Gly Ala Pro Gly Glu Val Val Ala
            115                 120                 125

Val Pro Cys Pro Asp Tyr Ile Tyr Asp Phe Asn His Lys Gly His Ala
        130                 135                 140

Tyr Arg Arg Cys Asp Arg Asn Gly Ser Trp Glu Val Val Pro Gly His
145                 150                 155                 160

Asn Arg Thr Trp Ala Asn Tyr Ser Glu Cys Leu Lys Phe Met Thr Asn
                165                 170                 175

Glu Thr Arg Glu Arg Glu Val Phe Asp Arg Leu Gly Met Ile Tyr Thr
            180                 185                 190

Val Gly Tyr Ser Met Ser Leu Ala Ser Leu Thr Val Ala Val Leu Ile
        195                 200                 205

Leu Ala Tyr Phe Arg Arg Leu His Cys Thr Arg Asn Tyr Ile His Met
    210                 215                 220

His Met Phe Leu Ser Phe Met Leu Arg Ala Ala Ser Ile Phe Val Lys
225                 230                 235                 240

Asp Ala Val Leu Tyr Ser Gly Phe Thr Leu Asp Glu Ala Glu Arg Leu
                245                 250                 255

Thr Glu Glu Glu Leu His Ile Ile Ala Gln Val Pro Pro Pro Pro Ala
            260                 265                 270

Ala Ala Ala Val Gly Tyr Ala Gly Cys Arg Val Ala Val Thr Phe Phe
        275                 280                 285

Leu Tyr Phe Leu Ala Thr Asn Tyr Tyr Trp Ile Leu Val Glu Gly Leu
    290                 295                 300

Tyr Leu His Ser Leu Ile Phe Met Ala Phe Phe Ser Glu Lys Lys Tyr
305                 310                 315                 320

Leu Trp Gly Phe Thr Ile Phe Gly Trp Gly Leu Pro Ala Val Phe Val
                325                 330                 335

Ala Val Trp Val Gly Val Arg Ala Thr Leu Ala Asn Thr Gly Cys Trp
            340                 345                 350

Asp Leu Ser Ser Gly His Lys Lys Trp Ile Ile Gln Val Pro Ile Leu
        355                 360                 365

Ala Ser Val Val Leu Asn Phe Ile Leu Phe Ile Asn Ile Ile Arg Val
    370                 375                 380

Leu Ala Thr Lys Leu Arg Glu Thr Asn Ala Gly Arg Cys Asp Thr Arg
385                 390                 395                 400

Gln Gln Tyr Arg Lys Leu Leu Arg Ser Thr Leu Val Leu Val Pro Leu
                405                 410                 415

Phe Gly Val His Tyr Thr Val Phe Met Ala Leu Pro Tyr Thr Glu Val
            420                 425                 430

Ser Gly Thr Leu Trp Gln Ile Gln Met His Tyr Glu Met Leu Phe Asn
        435                 440                 445

Ser Phe Gln Gly Phe Phe Val Ala Ile Ile Tyr Cys Phe Cys Asn Gly
    450                 455                 460

Glu Val Gln Ala Glu Ile Arg Lys Ser Trp Ser Arg Trp Thr Leu Ala
465                 470                 475                 480

Leu Asp Phe Lys Arg Lys Ala Arg Ser Gly Ser Ser Ser Tyr Ser Tyr
                485                 490                 495

Gly Pro Met Val Ser His Thr Ser Val Thr Asn Val Gly Pro Arg Ala
            500                 505                 510

Gly Leu Ser Leu Pro Leu Ser Pro Arg Leu Pro Pro Ala Thr Thr Asn
```

|         | 515 |     |     |     |     | 520 |     |     |     |     | 525 |     |     |
|---------|-----|-----|-----|-----|-----|-----|-----|-----|-----|-----|-----|-----|-----|

Gly His Ser Gln Leu Pro Gly His Ala Lys Pro Gly Ala Pro Ala Thr
    530                         535                        540

Glu Thr Glu Thr Leu Pro Val Thr Met Ala Val Pro Lys Asp Asp Gly
545                       550                     555                  560

Phe Leu Asn Gly Ser Cys Ser Gly Leu Asp Glu Glu Ala Ser Gly Ser
                565                     570                  575

Ala Arg Pro Pro Pro Leu Leu Gln Glu Gly Trp Glu Thr Val Met
              580                  585                  590

( 2 ) INFORMATION FOR SEQ ID NO:21:

( i ) SEQUENCE CHARACTERISTICS:
        ( A ) LENGTH: 593 amino acids
        ( B ) TYPE: amino acid
        ( D ) TOPOLOGY: linear ( i i ) MOLECULE TYPE: protein ( x i ) SEQUENCE DESCRIPTION: SEQ ID NO:21:

Met Gly Thr Ala Arg Ile Ala Pro Gly Leu Ala Leu Leu Leu Cys Cys
 1                5                  10                15

Pro Val Leu Ser Ser Ala Tyr Ala Leu Val Asp Ala Asp Val Met
         20                 25                  30

Thr Lys Glu Glu Gln Ile Phe Leu Leu His Arg Ala Gln Ala Gln Cys
         35                40                45

Glu Lys Arg Leu Lys Glu Val Leu Gln Arg Pro Ala Ser Ile Met Glu
    50                  55                60

Ser Asp Lys Gly Trp Thr Ser Ala Ser Thr Ser Gly Lys Pro Arg Lys
65                  70                75                80

Asp Lys Ala Ser Gly Lys Leu Tyr Pro Glu Ser Glu Glu Asp Lys Glu
              85                  90                95

Ala Pro Thr Gly Ser Arg Tyr Arg Gly Arg Pro Cys Leu Pro Glu Trp
         100               105                110

Asp His Ile Leu Cys Trp Pro Leu Gly Ala Pro Gly Glu Val Val Ala
     115                120                125

Val Pro Cys Pro Asp Tyr Ile Tyr Asp Phe Asn His Lys Gly His Ala
130                   135                140

Tyr Arg Arg Cys Asp Arg Asn Gly Ser Trp Glu Leu Val Pro Gly His
145                  150                155              160

Asn Arg Thr Trp Ala Asn Tyr Ser Glu Cys Val Lys Phe Leu Thr Asn
              165                 170              175

Glu Thr Arg Glu Arg Glu Val Phe Asp Arg Leu Gly Met Ile Tyr Thr
            180               185                190

Val Gly Tyr Ser Val Ser Leu Ala Ser Leu Thr Val Ala Val Leu Ile
        195               200                205

Leu Ala Tyr Phe Arg Arg Leu His Cys Thr Arg Asn Tyr Ile His Met
    210                215                220

His Leu Phe Leu Ser Phe Met Leu Arg Ala Val Ser Ile Phe Val Lys
225                  230                235              240

Asp Ala Val Leu Tyr Ser Gly Ala Thr Leu Asp Glu Ala Glu Arg Leu
              245                 250              255

Thr Glu Glu Glu Leu Arg Ala Ile Ala Gln Ala Pro Pro Pro Pro Ala
            260               265                270

Thr Ala Ala Ala Gly Tyr Ala Gly Cys Arg Val Ala Val Thr Phe Phe
     275                280                285

-continued

| Leu | Tyr 290 | Phe | Leu | Ala | Thr | Asn 295 | Tyr | Tyr | Trp | Ile | Leu 300 | Val | Glu | Gly | Leu |
|---|---|---|---|---|---|---|---|---|---|---|---|---|---|---|---|
| Tyr 305 | Leu | His | Ser | Leu | Ile 310 | Phe | Met | Ala | Phe | Phe 315 | Ser | Glu | Lys | Lys | Tyr 320 |
| Leu | Trp | Gly | Phe | Thr 325 | Val | Phe | Gly | Trp | Gly 330 | Leu | Pro | Ala | Val | Phe 335 | Val |
| Ala | Val | Trp | Val 340 | Ser | Val | Arg | Ala | Thr 345 | Leu | Ala | Asn | Thr | Gly 350 | Cys | Trp |
| Asp | Leu | Ser 355 | Ser | Gly | Asn | Lys | Lys 360 | Trp | Ile | Ile | Gln | Val 365 | Pro | Ile | Leu |
| Ala | Ser 370 | Ile | Val | Leu | Asn | Phe 375 | Ile | Leu | Phe | Ile | Asn 380 | Ile | Val | Arg | Val |
| Leu 385 | Ala | Thr | Lys | Gln | Arg 390 | Glu | Thr | Asn | Ala | Gly 395 | Arg | Cys | Asp | Thr | Arg 400 |
| Gln | Gln | Tyr | Arg | Lys 405 | Leu | Leu | Lys | Ser | Thr 410 | Leu | Val | Leu | Met | Pro 415 | Leu |
| Phe | Gly | Val | His 420 | Tyr | Ile | Val | Phe | Met 425 | Ala | Thr | Pro | Tyr | Thr 430 | Glu | Val |
| Ser | Gly | Thr 435 | Leu | Trp | Gln | Val | Gln 440 | Met | His | Tyr | Glu | Met 445 | Leu | Phe | Asn |
| Ser | Phe 450 | Gln | Gly | Phe | Phe | Val 455 | Ala | Ile | Ile | Tyr | Cys 460 | Phe | Cys | Asn | Gly |
| Glu 465 | Val | Gln | Ala | Glu | Ile 470 | Lys | Lys | Ser | Trp | Ser 475 | Arg | Trp | Thr | Leu | Ala 480 |
| Leu | Asp | Phe | Lys | Arg 485 | Lys | Ala | Arg | Ser | Gly 490 | Ser | Ser | Ser | Tyr | Ser 495 | Tyr |
| Gly | Pro | Met | Val 500 | Ser | His | Thr | Ser | Val 505 | Thr | Asn | Val | Gly | Pro 510 | Arg | Val |
| Gly | Leu | Gly 515 | Leu | Pro | Leu | Ser | Pro 520 | Arg | Leu | Leu | Pro | Thr 525 | Ala | Thr | Thr |
| Asn | Gly 530 | His | Pro | Gln | Leu | Pro 535 | Gly | His | Ala | Lys | Pro 540 | Gly | Thr | Pro | Ala |
| Leu 545 | Glu | Thr | Leu | Glu | Thr 550 | Thr | Pro | Pro | Ala | Met 555 | Ala | Ala | Pro | Lys | Asp 560 |
| Asp | Gly | Phe | Leu | Asn 565 | Gly | Ser | Cys | Ser | Gly 570 | Leu | Asp | Glu | Glu | Ala 575 | Ser |
| Gly | Pro | Glu | Arg 580 | Pro | Pro | Ala | Leu | Leu 585 | Gln | Glu | Glu | Trp | Glu 590 | Thr | Val |
| Met | | | | | | | | | | | | | | | |

What is claimed is:

1. An essentially purified preparation of a polypeptide comprising the amino acid sequence of a naturally-occurring mammalian parathyroid hormone receptor, said receptor having an amino acid sequence with at least 75% identity to the amino acid sequence of SEQ ID NO: 20.

2. A polypeptide consisting of at least six amino acids, and less than the complete amino acid sequence, of the human parathyroid hormone receptor represented by SEQ ID NO: 21, wherein said polypeptide binds parathyroid hormone or parathyroid hormone-related protein and comprises an amino acid sequence selected from the group consisting of:
   (a) (SEQ ID NO:5),
   (b) (SEQ ID NO:6),
   (c) (SEQ ID NO:7),
   (d) (SEQ ID NO:8),
   (e) (SEQ ID NO:9),
   (f) (SEQ ID NO:10),
   (g) (SEQ ID NO:11),
   (h) (SEQ ID NO:12),
   (i) (SEQ ID NO:13), and
   (j) a fragment of any one of (a)–(i).

3. The polypeptide of claim 2, wherein said polypeptide comprises an amino acid sequence selected from the group consisting of:
   (a) (SEQ ID NO:5),
   (b) (SEQ ID NO:6),
   (c) (SEQ ID NO:7),
   (d) (SEQ ID NO:8),
   (e) (SEQ ID NO:9),
   (f) (SEQ ID NO:10), (g) (SEQ ID NO:11),
(h) (SEQ ID NO:12), and
(i) (SEQ ID NO:13).

4. The preparation of claim 1, wherein the receptor is a human parathyroid hormone receptor encoded by SEQ ID NO:21.

5. The preparation of claim 1, wherein the receptor is an opossum or rat parathyroid hormone receptor encoded by SEQ ID NO:18, SEQ ID NO:19, or SEQ ID NO:20.

6. A composition comprising (a) a polypeptide having the amino acid sequence of a naturally-occurring mammalian parathyroid hormone receptor, and (b) a pharmaceutically-acceptable carrier, wherein said composition is substantially free from proteins and lipids with which said receptor is naturally associated.

7. The composition of claim 6, wherein the receptor is a human parathyroid hormone receptor.

8. A composition comprising (a) the polypeptide of claim 1, and (b) a pharmaceutically-acceptable carrier.

9. A composition comprising (a) the polypeptide of claim 3, and (b) a pharmaceutically-acceptable carrier.

10. The preparation of claim 1, wherein the polypeptide was produced upon expression of a recombinant DNA molecule encoding the receptor.

11. The preparation of claim 10, wherein the antisense strand of the recombinant DNA molecule hybridizes under under conditions of high stringency to a hybridization probe consisting of an 18-nucleotide portion of a sequence selected from the group consisting of SEQ ID NO:1, SEQ ID NO:2, SEQ ID NO:3, and SEQ ID NO:4.

12. The preparation of claim 10, wherein the antisense strand of the recombinant DNA molecule hybridizes under conditions of high stringency to a hybridization probe consisting of a 30-nucleotide portion of a sequence selected from the group consisting of SEQ ID NO:1, SEQ ID NO:2, SEQ ID NO:3, and SEQ ID NO:4.

* * * * *